United States Patent
Miranda et al.

(10) Patent No.: US 6,221,383 B1
(45) Date of Patent: *Apr. 24, 2001

(54) SOLUBILITY PARAMETER BASED DRUG DELIVERY SYSTEM AND METHOD FOR ALTERING DRUG SATURATION CONCENTRATION

(75) Inventors: Jesus Miranda; Steven Sablotsky, both of Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/318,121

(22) Filed: May 25, 1999

Related U.S. Application Data

(60) Division of application No. 08/907,906, filed on Aug. 11, 1997, which is a continuation-in-part of application No. 08/178,558, filed on Jan. 7, 1994, now Pat. No. 5,656,286.

(51) Int. Cl.$^7$ ........................................ A61F 13/02
(52) U.S. Cl. ........................................ 424/449; 424/448
(58) Field of Search ........................................ 424/448, 449

(56) References Cited

U.S. PATENT DOCUMENTS

| | | | |
|---|---|---|---|
| 3,969,308 | 7/1976 | Penneck | 260/37 SB |
| 3,972,995 | 8/1976 | Tsuk et al. | 424/28 |
| 4,291,015 | 9/1981 | Keith et al. | 424/28 |

(List continued on next page.)

FOREIGN PATENT DOCUMENTS

| | | |
|---|---|---|
| 2027053 | 4/1991 | (CA) . |
| 0-201-828 | 11/1986 | (EP) . |
| 208395 | 1/1987 | (EP) . |
| 0-272-045 | 6/1988 | (EP) . |
| 0-343-807 | 11/1989 | (EP) . |
| 0 371 496 | 6/1990 | (EP) . |
| 0-416-842 | 3/1991 | (EP) . |
| 0529123 | 3/1993 | (EP) . |
| 2 105 990 | 4/1983 | (GB) . |
| 54-89017 | 7/1979 | (JP) . |
| 58-225010 | 12/1983 | (JP) . |
| WO 91/05529 | 5/1991 | (WO) . |
| WO 93/08795 | 5/1993 | (WO) . |
| WO 97/11689 | 4/1997 | (WO) . |

OTHER PUBLICATIONS

Sloan, K.B. et al., "Use of Solubility Parameters of Drug and Vehicle to Predict Flux Through Skin", The Journal of Investigative Dermatology, vol. 87 (No. 2) pp. 244–252 (Aug. 1996).

(List continued on next page.)

*Primary Examiner*—Shelley A. Dodson
*Assistant Examiner*—Michael A. Williamson
(74) *Attorney, Agent, or Firm*—Foley & Lardner

(57) ABSTRACT

A blend of at least two polymers, or at least one polymer and a soluble polyvinylpyrrolidone, in combination with a drug provides a pressure-sensitive adhesive composition for a transdermal drug delivery system in which the drug is delivered from the pressure-sensitive adhesive composition and through dermis when the pressure-sensitive adhesive composition is in contact with human skin. According to the invention, soluble polyvinylpyrrolidone can be used to prevent crystallization of the drug, without affecting the rate of drug delivery from the pressure-sensitive adhesive composition.

4 Claims, 19 Drawing Sheets

U.S. PATENT DOCUMENTS

| | | | |
|---|---|---|---|
| 4,292,301 | 9/1981 | Keith et al. | 424/28 |
| 4,390,520 | 6/1983 | Nagai et al. | 424/28 |
| 4,438,139 | 3/1984 | Keith et al. | 424/28 |
| 4,542,013 | 9/1985 | Keith | 424/28 |
| 4,585,452 | 4/1986 | Sablotsky | 604/896 |
| 4,593,053 | 6/1986 | Jevne et al. | 523/111 |
| 4,668,232 | 5/1987 | Cordes et al. | 64/897 |
| 4,690,683 | 9/1987 | Chien et al. | 604/896 |
| 4,693,887 | 9/1987 | Shah | 424/19 |
| 4,696,821 | 9/1987 | Belsole | 424/448 |
| 4,699,146 | 10/1987 | Sieverding | 128/640 |
| 4,750,482 | 6/1988 | Sieverding | 128/156 |
| 4,769,013 | 9/1988 | Lorenz et al. | 604/265 |
| 4,814,168 | 3/1989 | Sablotsky et al. | 424/78 |
| 4,845,081 | 7/1989 | Sloan | 514/232.2 |
| 4,883,669 | 11/1989 | Chien et al. | 424/448 |
| 4,906,169 | 3/1990 | Chien et al. | 424/448 |
| 4,911,916 | 3/1990 | Cleary | 424/449 |
| 4,931,281 | 6/1990 | Kim et al. | 424/448 |
| 4,987,893 | 1/1991 | Salamone et al. | 128/156 |
| 4,994,267 | 2/1991 | Sablotsky | 424/78 |
| 5,032,403 | 7/1991 | Sinnreich | 424/448 |
| 5,059,189 | 10/1991 | Cilento et al. | 604/307 |
| 5,071,656 | 12/1991 | Lee et al. | 424/448 |
| 5,122,543 | 6/1992 | Khanna | 514/772.5 |
| 5,128,138 | 7/1992 | Blank | 424/449 |
| 5,141,750 | 8/1992 | Lee et al. | 424/448 |
| 5,151,271 | 9/1992 | Otsuka et al. | 424/443 |
| 5,154,922 | 10/1992 | Govil et al. | 424/448 |
| 5,230,896 | 7/1993 | Yeh et al. | 424/443 |
| 5,230,898 | 7/1993 | Horstmann et al. | 424/449 |
| 5,232,702 | 8/1993 | Pfister et al. | 424/448 |
| 5,232,703 | 8/1993 | Blank | 424/449 |
| 5,252,334 | 10/1993 | Chiang et al. | 424/448 |
| 5,260,064 | 11/1993 | Nakagawa et al. | 424/448 |
| 5,262,165 | 11/1993 | Govil et al. | 424/448 |
| 5,393,529 | 2/1995 | Hoffman et al. | 424/448 |
| 5,676,968 | 10/1997 | Lipp et al. . | |

OTHER PUBLICATIONS

Yu et al., "Transdermal Dual–Controlled Delivery of Testosterone and Estradiol: (1) Impact of System Design," Drug Devel, Indust. Pharm. 17(14): 1883–1904 (1991).

Ziller et al., "Control of Crystal Growth in Drug Suspensions," Pharm. Ind. 52(8):1017–1022 (1990).

Kuhnert–Brandstätter et al., "Kristalisationsvorgänge in Suspensionen von Steroidhormonen," Sci. Pharm. 35(4):287–297 (1967).

English translation of Japanese patent application No. 2–48859, filed Feb. 27, 1990.

English translation of European Patent Application No. 0–201–828 (1986).

"The Merck Index, An Encyclopedia of Chemicals, Drugs, And Biologicals," (Budavari et al., eds.) pp. 391–392, ($11^{th}$ Ed. Merck & Co. 1989).

Farley, D. "Estrogens," FDA Consumer (page numbers unknown) (Nov. 1990).

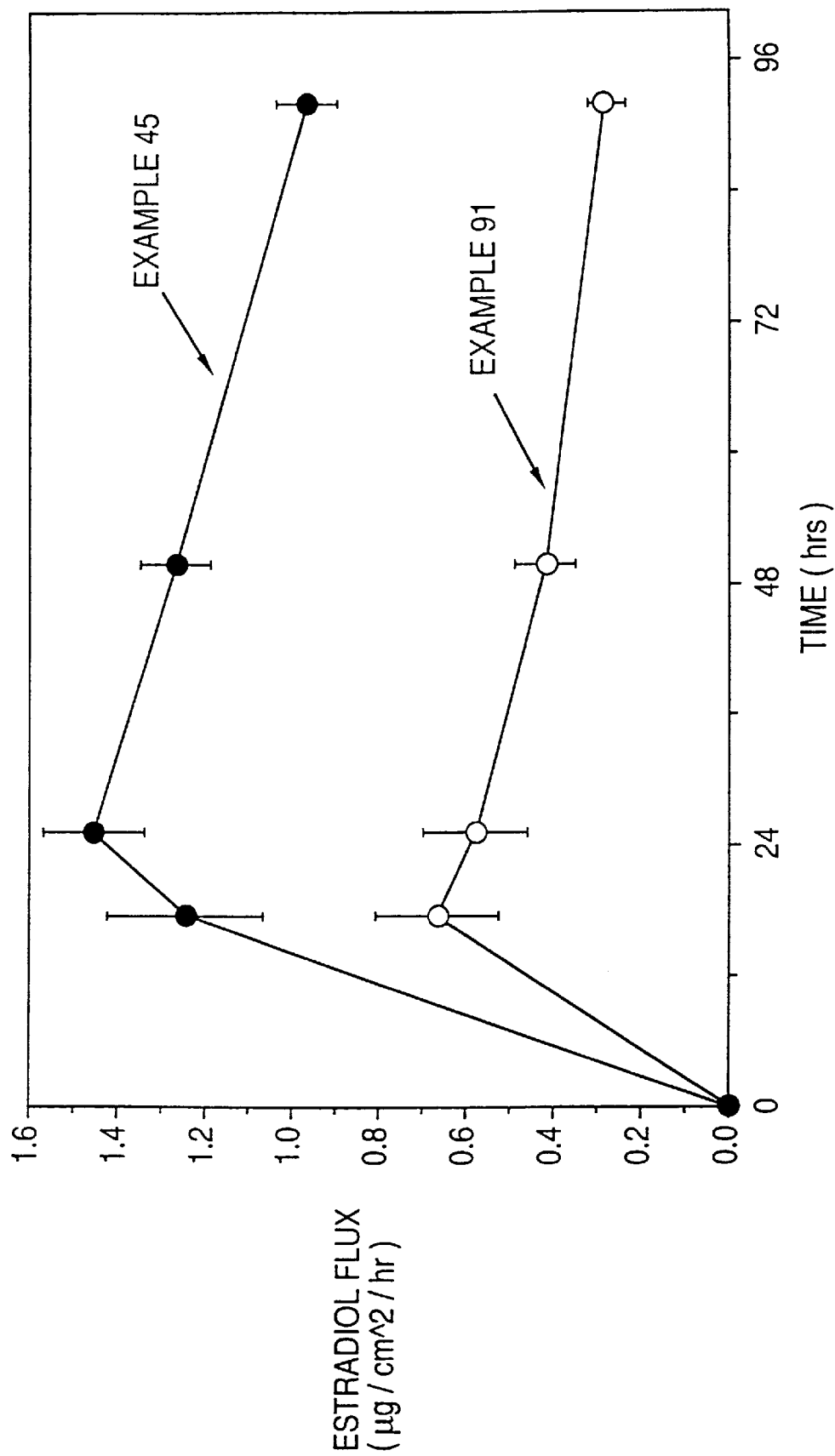

SOLUBILITY PARAMETER BASED DRUG DELIVERY SYSTEM AND METHOD FOR ALTERING DRUG SATURATION CONCENTRATION

CROSS-REFERENCE TO RELATED APPLICATION

This application is a divisional application of Ser. No. 08/907,906 filed Aug. 11, 1997 which is a continuation of Ser. No. 08/178,558 filed Jan. 7, 1994, now U.S. Pat. No. 5,656,286 granted Aug. 12, 1997.

BACKGROUND OF THE INVENTION

This invention relates generally to transdermal drug delivery systems, and more particularly, to a transdermal drug delivery composition wherein a blend of polymers is utilized to affect the rate of drug delivery from the composition. More specifically, a plurality of polymers including a soluble polyvinylpyrrolidone having differing solubility parameters, preferably immiscible with each other, adjusts the solubility of the drug in a polymeric adhesive system formed by the blend, affects the maximum concentration of the drug in the system, and modulates the delivery of the drug from the composition and through the dermis.

The use of a transdermal composition, for example a pressure-sensitive adhesive containing a medicament, namely, a drug, as a means of controlling drug delivery through the skin at essentially a constant rate, is well known. Such known delivery systems involve incorporation of a medicament into a carrier such as a polymeric matrix and/or a pressure-sensitive adhesive formulation. The pressure-sensitive adhesive must adhere effectively to the skin and permit migration of the medicament from the carrier through the skin and into the bloodstream of the patient.

Drug concentration in a monolithic transdermal delivery system can vary widely depending on the drug and polymers used. For example, certain drugs are effective in low doses and therefore the transdermal formulation may involve low concentrations, illustratively 5% or less by weight of the medicament in an adhesive. Other drugs, such as nitroglycerin, require large doses to be effective and the transdermal formulation therefore may involve high drug concentrations, approximately between 5 to 40% or more by weight in an adhesive. Low concentrations of medicament typically do not critically affect the adhesion, tack, and shear resistance properties of the adhesive. However, low drug concentrations in the adhesive can result in difficulties in achieving an acceptable delivery rate of the medicament. High concentrations, on the other hand, frequently affect the adhesion properties of the adhesives. The deleterious effects are particularly exacerbated by drugs which also act as plasticizers or solvents for the polymeric adhesive (e.g., nitroglycerin in polyacrylates).

There is a need in the art for an adhesive composition for transdermal drug delivery systems which can selectably incorporate low concentrations of drug and deliver same at an adequate and controlled rate or incorporate high concentrations of drugs while retaining good physical adhesive properties.

In transdermal drug delivery systems, the presence of crystals (drugs and/or additives) is generally undesirable. If the drug is present in crystalline form, it is not available for release from the system, and therefore not available for delivery. Moreover, although drug crystals can first dissolve and then release from the system, such a process is usually rate-limiting and tends to reduce delivery.

Crystal size and distribution thus become important parameters which must be controlled in order to control delivery. These parameters are, however, usually difficult to control. Failure to control crystal size and distribution can result in products whose appearance suggests that the manufacturing process by which they are produced is not under control. More importantly, the presence of large crystals, particularly in excessive amounts, can be detrimental to adhesive-type transdermals. Crystals on the surface of the adhesive system can result in loss of tack. Furthermore, surface crystals can come into direct contact with the skin, and could cause skin irritation.

There is a need in the art for an adhesive composition for transdermal delivery systems which can prevent or suppress crystallization of drugs therein.

It is, therefore, an object of this invention to provide a transdermal drug delivery system wherein the rate of drug delivery from the transdermal composition may be selectably modulated.

It is another object of this invention to provide a transdermal drug delivery system wherein the rate of drug delivery from the transdermal composition may be selectably modulated by adjusting the solubility and/or diffusivity of the drug in the multiple polymer adhesive system.

It is also an object of this invention to provide a transdermal drug delivery system wherein the multiple polymer adhesive system is simple to manufacture.

It is a further object of this invention to provide a transdermal drug delivery system wherein drug-loading of a multiple polymer adhesive system may be selectably varied without adverse effects on drug delivery rate and adhesive properties, such as adhesion, tack, and shear resistance.

It is additionally an object of this invention to provide a transdermal drug delivery system wherein a novel multiple polymer adhesive system is provided which has desirable physical properties.

SUMMARY OF THE INVENTION

The foregoing and other objects are achieved by this invention which provides a transdermal drug delivery system wherein a blend of at least two polymers, or at least one polymer and a soluble polyvinylpyrrolidone permits increased loading of a drug and adjusts the solubility of a drug in the blend and thereby modulates the delivery of the drug from the system and through the dermis.

In accordance with one aspect of the invention, an improved pressure-sensitive adhesive composition of the type which is suitable as a matrix for controlled release of a drug therefrom comprises a blend of a rubber-based pressure-sensitive adhesive and a soluble polyvinylpyrrolidone (PVP).

The term "polyvinylpyrrolidone," or "PVP" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum solubile, and Poly(1-vinyl-2-pyrrolidone). The copolymer vinyl acetate vinylpyrrolidone is known to the pharmaceutical industry as Copolyvidon, Copolyvidone, and Copolyvidonum.

The term "soluble" when used with reference to PVP means that the polymer is soluble in water and generally is not substantially cross-linked, and has a molecular weight of less than about 2,000,000. See, generally, Bühler, KOLLIDON®: POLYVINYLPRYRROLIDONE FOR THE PHARMACEUTICAL INDUSTRY, BASF Aktiengesellschaft (1992).

It has been surprisingly found that use of a soluble PVP results in the ability to form a film that does not contain particles of insoluble PVP and in the ability to employ higher concentrations of drug without resulting in increased crystallization of the drug.

In accordance with another embodiment of the invention, an improved pressure-sensitive adhesive composition of the type which is suitable as a matrix for controlled release of a drug therefrom comprises a blend of a rubber-based pressure-sensitive adhesive having a first solubility parameter, a polyacrylate polymer having a second solubility parameter, and a soluble PVP, the first and second solubility parameters preferably being different from one another by an increment of at least 2 $(J/cm^3)^{1/2}$. The blend, therefore, has a characteristic net solubility parameter.

In accordance with further embodiment of the invention, an improved pressure-sensitive adhesive composition of the type which is suitable as a matrix for controlled release of a drug therefrom comprises a blend of a rubber-based pressure-sensitive adhesive having a first solubility parameter, and a polyacrylate polymer having a second solubility parameter, the first and second solubility parameters preferably being different from one another by an increment of at least 2 $(J/cm^3)^{1/2}$. The blend, therefore, has a characteristic net solubility parameter.

Particularly preferred embodiments include binary blends comprising a rubber-based pressure-sensitive adhesive and a soluble PVP, wherein the rubber-based pressure-sensitive adhesive is a polysiloxane. Polysiloxane is preferably present in the pressure-sensitive adhesive composition in an amount ranging from about 9% to about 97% by weight of the total pressure-sensitive adhesive composition.

Other particularly preferred embodiments include ternary blends comprising a rubber-based pressure-sensitive adhesive, a polyacrylate polymer, and a soluble PVP, wherein the rubber-based pressure-sensitive adhesive is a polysiloxane. Polysiloxane is preferably present in the pressure-sensitive adhesive composition in an amount ranging from about 9% to about 97% by weight of the total pressure-sensitive adhesive composition, while the polyacrylate polymer is preferably present in an amount ranging from about 5% to about 85%. Preferably, the ratio of the polyacrylate polymer to the rubber-based pressure-sensitive adhesive is from about 2:98 to about 96:4, and more preferably from about 2:98 to about 86:14 by weight.

Other particularly preferred embodiments include blends comprising a rubber-based pressure-sensitive adhesive and a polyacrylate polymer, wherein the rubber-based pressure-sensitive adhesive is a polysiloxane. Polysiloxane is preferably present in the pressure-sensitive adhesive composition in an amount ranging from about 9% to about 97% by weight of the total pressure-sensitive adhesive composition, while the polyacrylate polymer is preferably present in an amount ranging from about 5% to about 85%. Preferably, the ratio of the polyacrylate polymer to the rubber-based pressure-sensitive adhesive is from about 2:98 to about 96:4, and more preferably from about 2:98 to about 86:14 by weight.

In both binary and ternary blends, soluble PVP is preferably present in the pressure-sensitive adhesive composition in an amount ranging from about 1% to about 20% by weight of the total pressure-sensitive adhesive composition.

The pressure-sensitive adhesive compositions may further include enhancers, fillers, co-solvents, and excipients as are known in the art for use in such compositions.

In a dermal adhesive composition embodiment of the invention, a multiple polymer adhesive system comprises a blend of 14–94% by weight of a rubber-based pressure-sensitive adhesive, 5–85% by weight of a polyacrylate polymer, and 2–10% by weight of a soluble PVP, and the multiple polymer adhesive system comprises about 50–99% by weight of the dermal adhesive composition. This multiple polymer adhesive system is combined with a drug in the amount of 0.1–50% by weight of the total dermal adhesive composition. Optional additives, such as co-solvent for the drug (up to 30% by weight) and enhancers (up to 20% by weight) may be included in the dermal adhesive composition.

In transdermal drug delivery system embodiments, incorporating a drug in the improved pressure-sensitive adhesive composition, the characteristic net solubility parameter can be preselected to adjust the saturation concentration of the drug in the composition and thereby control the release of the drug. The saturation concentration of the drug may be adjusted either upward or downward depending upon whether the rate of release is to be enhanced or retarded.

In particularly preferred embodiments, the drug is a steroid, such as an estrogen or a progestational agent, or combination thereof. In other preferred embodiments, the drug may be a $\beta_2$-adrenergic agonist, such as albuterol, or a cardioactive agent, such as nitroglycerin. In still other embodiments, the drug is a cholinergic agent, such as pilocarpine, or an antipsychotic such as haloperidol or a tranquilizer/sedative such as alprazolam.

The transdermal drug delivery system may comprise a monolithic adhesive matrix device in some embodiments. The transdermal drug delivery system may further include a backing material and a release liner as is known in the art.

The saturation concentration of a drug in a transdermal drug delivery system of the type having a drug-containing pressure-sensitive adhesive diffusion matrix is adjusted in accordance with an aspect of the present invention by blending at least two polymers having differing solubility parameters as defined above to form a pressure-sensitive adhesive diffusion matrix having a net solubility parameter which modifies the delivery rate of the drug from the pressure-sensitive adhesive diffusion matrix and through the dermis.

BRIEF DESCRIPTION OF THE DRAWINGS

Comprehension of the invention is facilitated by reading the following detailed description, in conjunction with the annexed drawing, in which.

Figure 15:
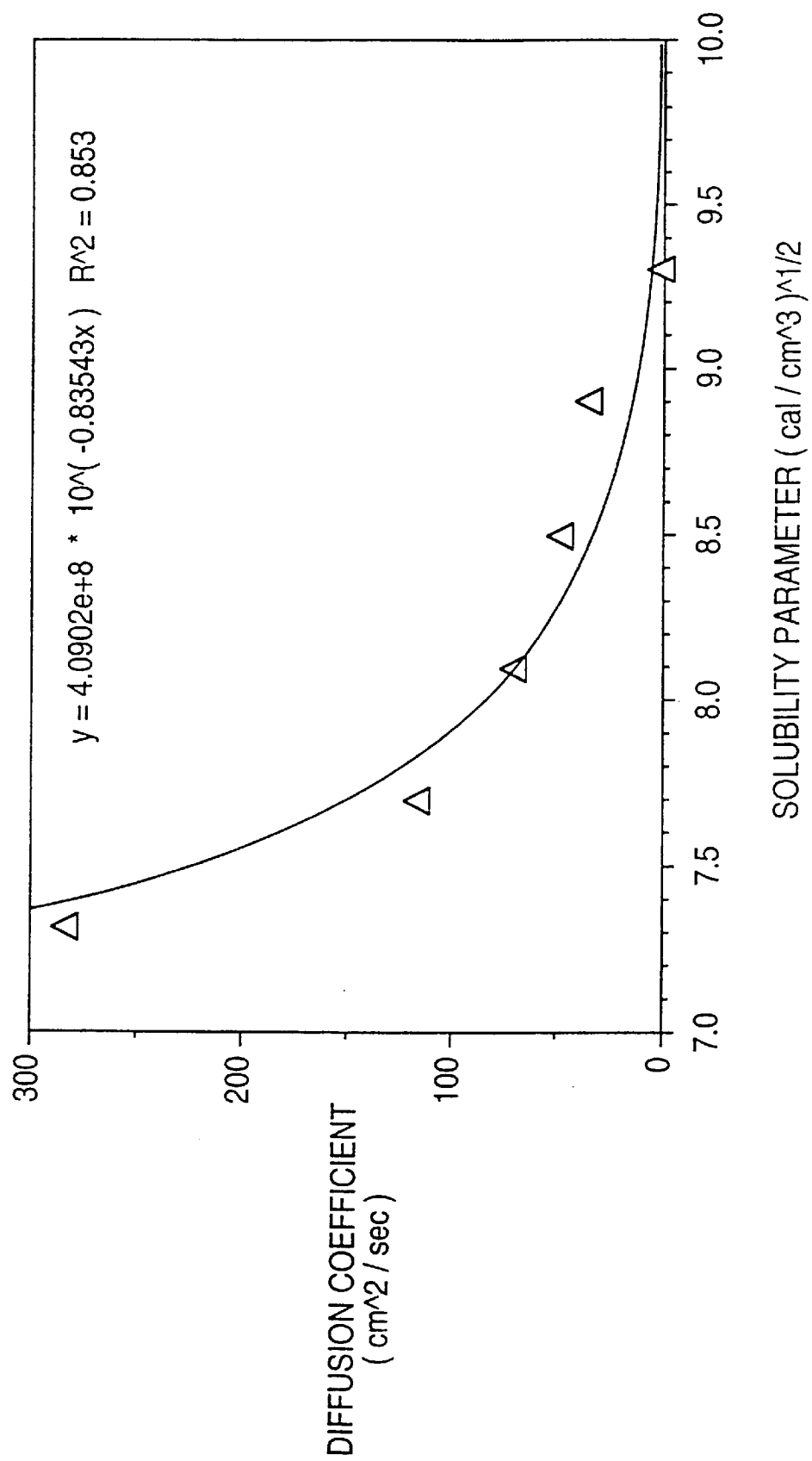
Figure 16:
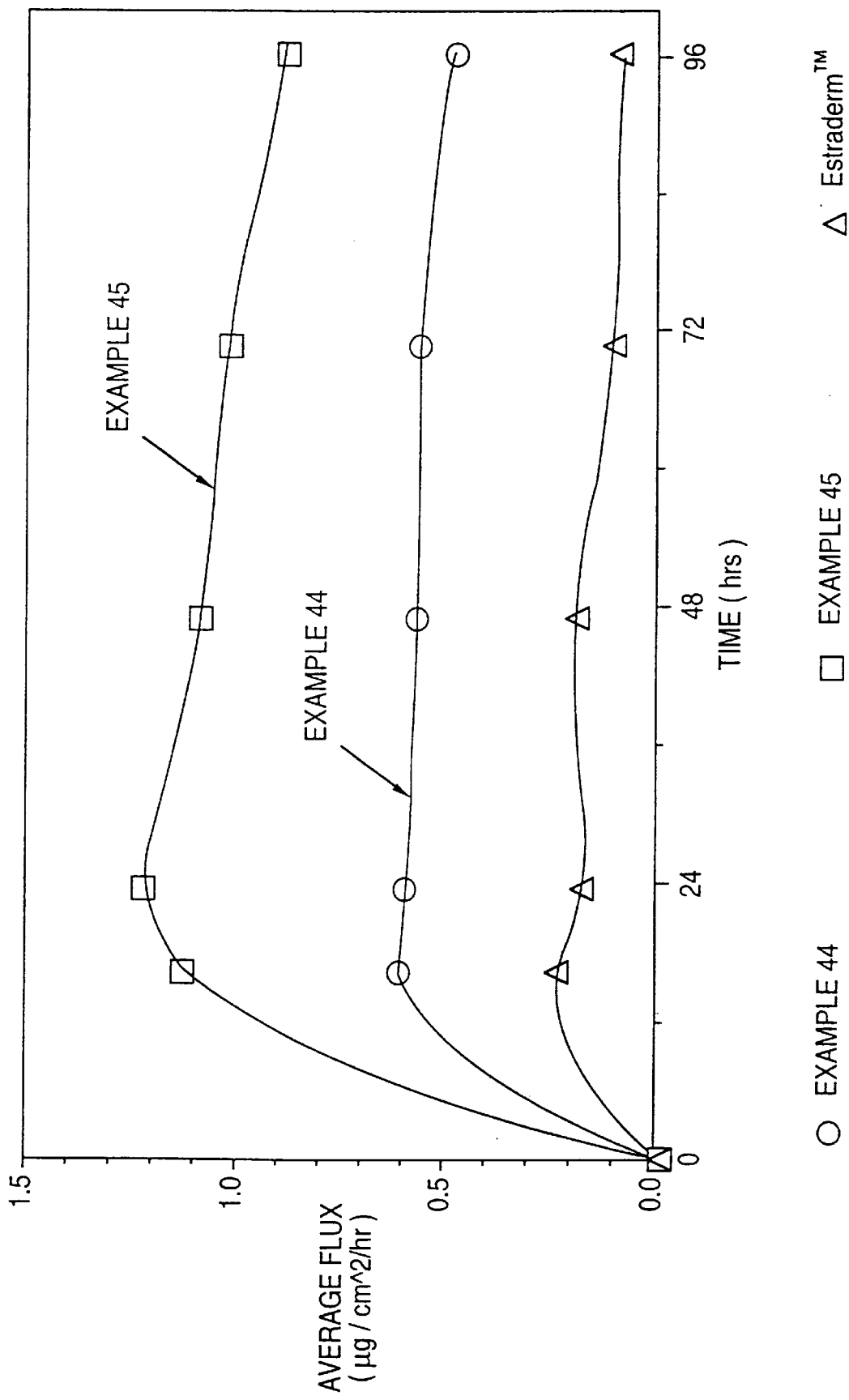
Figure 17:
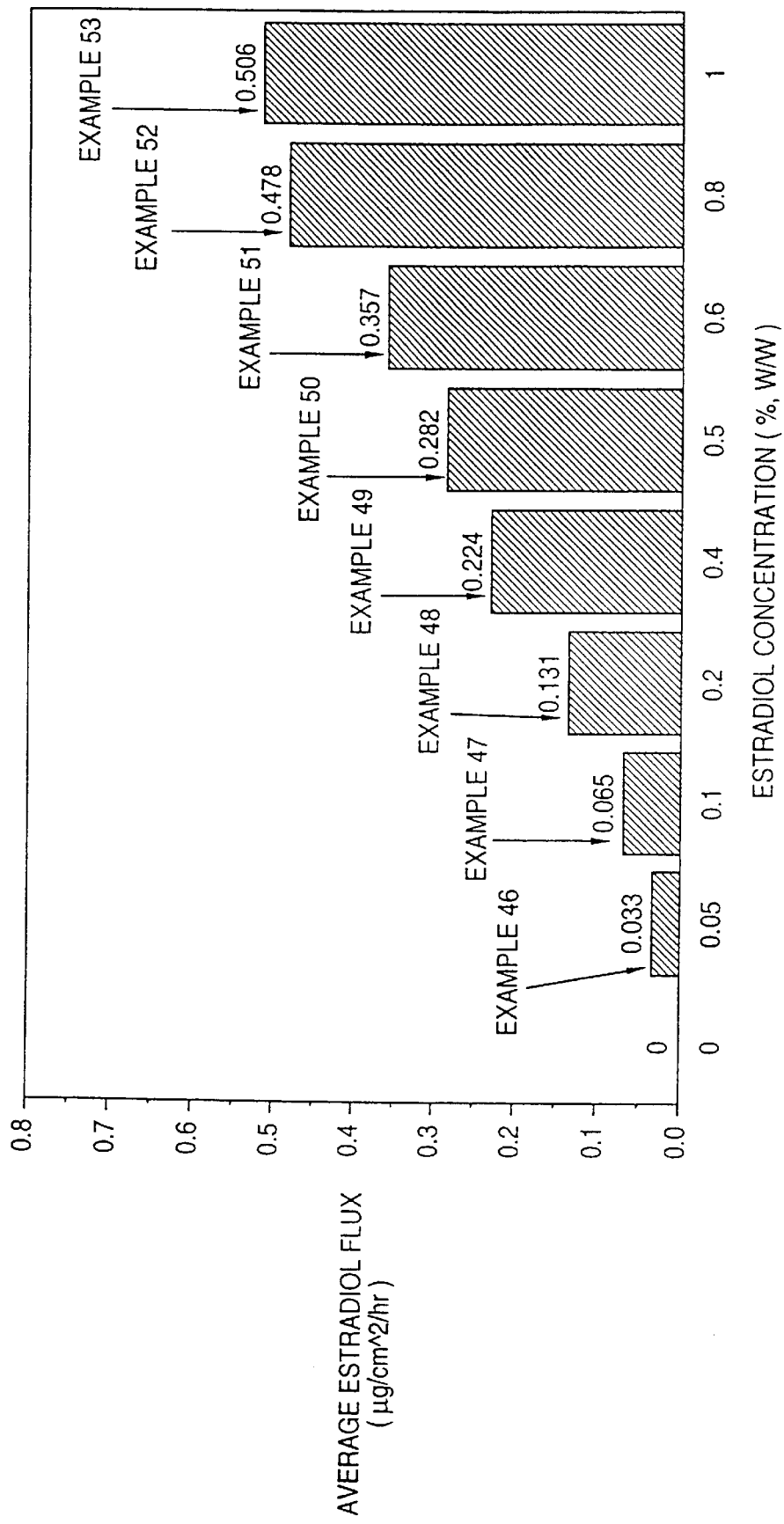
Figure 18:
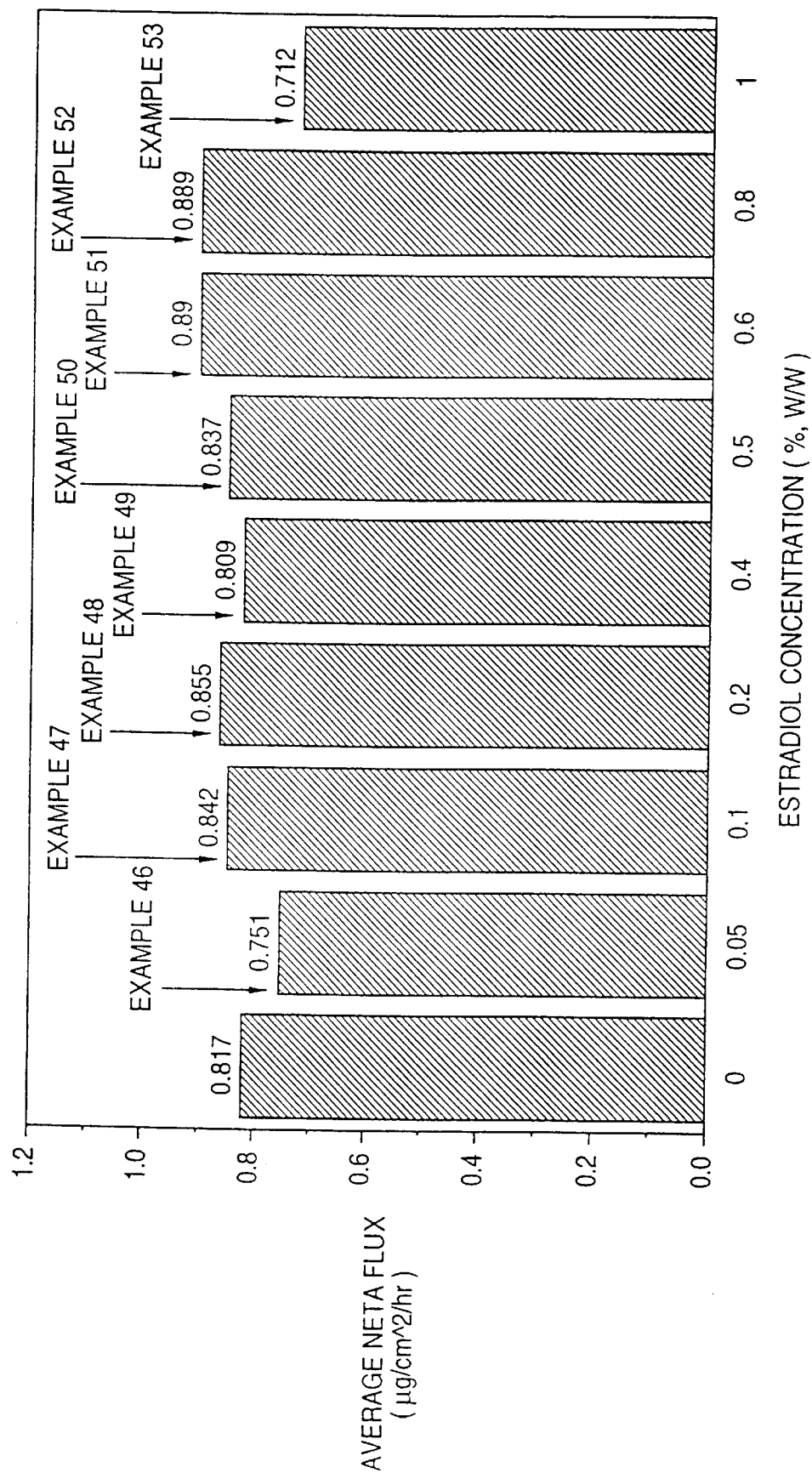
Figure 19:
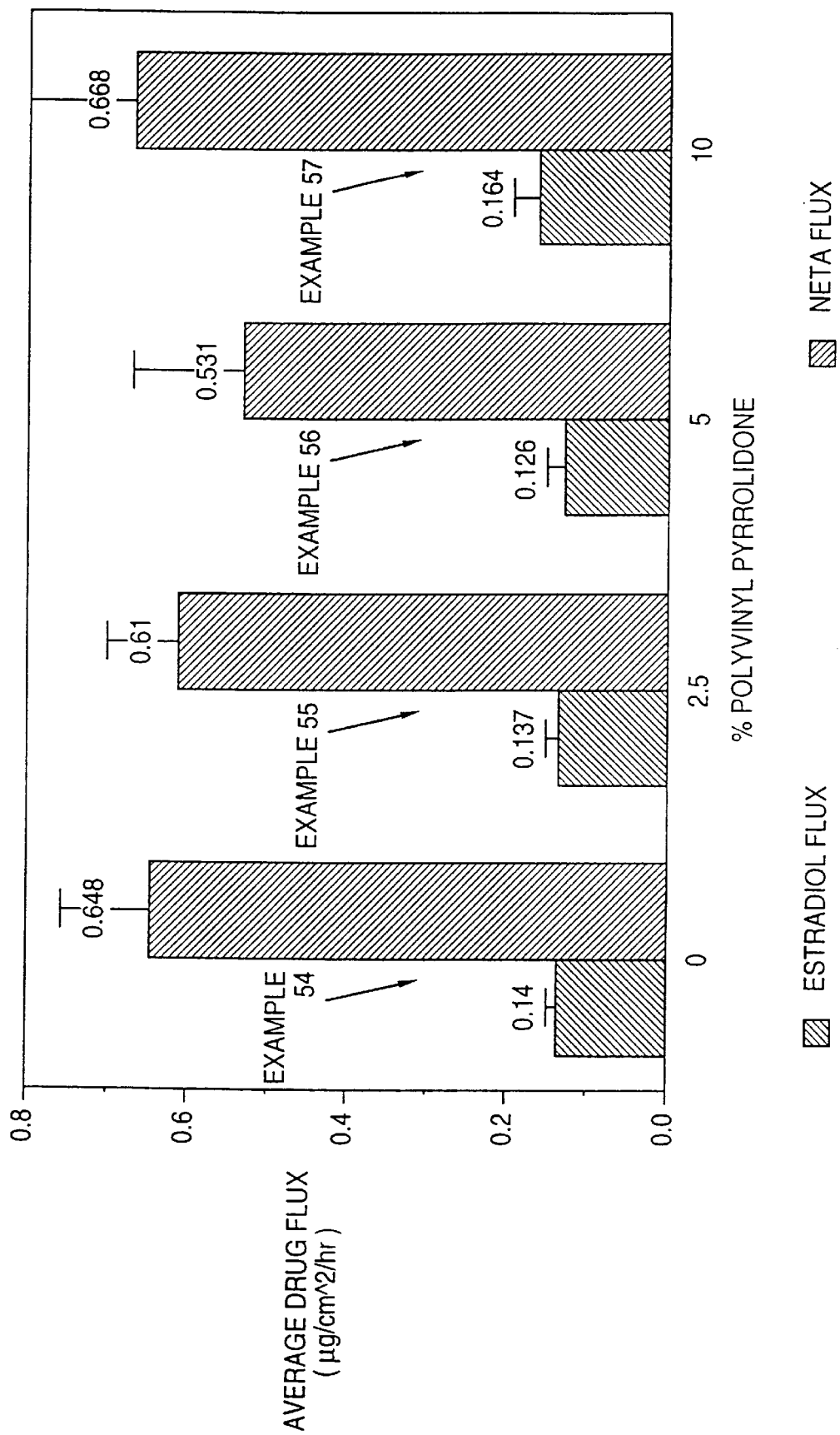

$$SP_{net} = \phi_{ps} SP_{ps} + \phi_{pa} SP_{pa},$$

where $\phi_{ps}$ is the weight percentage of polysiloxane and $SP_{ps}$ is the solubility parameter of polysiloxane. The subscript "pa" refers to the polyacrylate;

FIG. 15 is a plot of diffusion coefficient versus net solubility parameter;

FIG. 16 shows the average flux of estradiol for two compositions of this invention containing a soluble PVP;

FIG. 17 shows estradiol flux through the human epidermis from a PVP-containing compositions of this invention;

FIG. 18 shows norethindrone flux through human epidermis in a composition of this invention containing estradiol and soluble PVP;

FIG. 19 shows average estradiol and norethindrone acetate flux from a composition of this invention containing varying concentrations of soluble PVP; and FIG. 20 shows the effect of soluble PVP on estradiol flux through human epidermis.

DETAILED DESCRIPTION OF PREFERRED EMBODIMENTS

In one aspect of the present invention, a pressure-sensitive adhesive composition is provided which comprises a blend of at least two polymers and a soluble PVP, and a drug. The blend of at least two polymers is herein referred to as a multiple polymer adhesive system. The term "blend" is used herein to mean that there is no, or substantially no, chemical reaction or cross-linking (other than simple H-bonding) between the different polymers in the multiple polymer adhesive system.

As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

The term pressure-sensitive adhesive also includes mixtures of different polymers and mixtures of polymers, such as polyisobutylenes (PIB), of different molecular weights, wherein each resultant mixture is a pressure-sensitive. In the last case, the polymers of lower molecular weight in the mixture are not considered to be "tackifiers," said term being reserved for additives which differ other than in molecular weight from the polymers to which they are added.

As used herein, the term "rubber-based pressure-sensitive adhesive" refers to a viscoelastic material which has the properties of a pressure-sensitive adhesive and which contains at least one natural or synthetic elastomeric polymer.

As used herein, the term "drug," and its equivalent, "bioactive agent," is intended to have its broadest interpretation as any therapeutically, prophylactically and/or pharmacologically or physiologically beneficial active substance, or mixture thereof, which is delivered to a living organism to produce a desired, usually beneficial, effect.

More specifically, any drug which is capable of producing a pharmacological response, localized or systemic, irrespective of whether therapeutic, diagnostic, or prophylactic in nature, in plants or animals is within the contemplation of the invention. Also within the contemplation of the invention are such bioactive agents as pesticides, insect repellents, sun screens, cosmetic agents, etc. It should be noted that the drugs and/or bioactive agents may be used singly or as a mixture of two or more such agents, and in amounts sufficient to prevent, cure, diagnose or treat a disease or other condition, as the case may be.

The multiple polymer adhesive not only functions as a carrier matrix for the drug, but enhances the rate of release of the drug, and hence the transdermal permeation rate. In some embodiments of the invention, however, the multiple polymer adhesive system will function to retard the transdermal permeation rate.

A soluble PVP is blended with one or more other polymers in order to further modulate the transdermal permeation rate of the drug.

An important aspect of the present invention is the discovery that the transdermal permeation rate of a drug from the multiple polymer adhesive system can be selectively modulated by adjusting the solubility of the drug in the device. As used herein, the term "transdermal permeation rate" means the rate of passage of the drug through the skin; which, as known in the art, may or may not be affected by the rate of release of the drug from the carrier.

The polymers comprising the multiple polymer adhesive system are preferably inert to the drug, and are preferably immiscible with each other, as can be surmised by their different solubility parameters. Forming a blend of multiple polymers results in an adhesive system having a characteristic "net solubility parameter," the selection of which advantageously permits a selectable modulation of the delivery rate of the drug by adjusting the solubility of the drug in the multiple polymer adhesive system.

Solubility parameter, also referred to herein as "SP," has been defined as the sum of all the intermolecular attractive forces, which are empirically related to the extent of mutual solubility of many chemical species. A general discussion of solubility parameters is found in an article by Vaughan, "Using Solubility Parameters in Cosmetics Formulation," *J. Soc. Cosmet. Chem.*, Vol.36, pages 319–333 (1985). Many methods have been developed for the determination of solubility parameters, ranging from theoretical calculations to totally empirical correlations. The most convenient method is Hildebrand's method, which computes the solubility parameter from molecular weight, boiling point and density data, which are commonly available for many materials and which yields values which are usually within the range of other methods of calculation:

$$SP=(\Delta E_v/V)^{1/2},$$

where V=molecular weight/density and $\Delta E_v$=energy of vaporization.

Alternatively written, $SP=(\Delta H_v/V-RT/V)^{1/2}$ where $\Delta H_v$= heat of vaporization, R=gas constant, and T is the absolute temperature, °K. For materials, such as high molecular weight polymers, which have vapor pressures too low to detect, and thus for which $\Delta H_v$ is not available, several methods have been developed which use the summation of atomic and group contributions to $\Delta H_v$:

$$\Delta Hv = \Sigma_i \Delta h_i,$$

where $\Delta h_i$ is the contribution of the ith atom or group to the molar heat of vaporization. One convenient method has been proposed by R. F. Fedors, *Polymer Engineering and Science*, Vol. 14, p. 147 (1974). In this method $\Delta E_v$ and V are be obtained by simply assuming that $$\Delta Ev = \Sigma_i \Delta e_i \text{ and } V = \Sigma_i v_i,$$

where $\Delta e_i$ and $v_i$ are the additive atomic and group contributions for the energy of vaporization and molar volume, respectively.

Yet another method of calculating the solubility parameter of a material is described by Small, *J. Applied Chem.* Vol. 3, p. 71 (1953).

Table I-A below sets forth solubility parameters of some exemplary adhesive polymers which would be useful in the practice of the invention and shows the variation of SP with molecular weight, free —OH and —COOH groups, the degree of cross-linking. Table IA is in $(cal/cm^3)^{1/2}$ and $(J/cm^3)^{1/2}$ as calculated by Small's method.

TABLE IA

| Polymers | Solubility Parameter | |
|---|---|---|
| | $(cal/cm^3)^{1/2}$ | $(J/cm^3)^{1/2}$ |
| Addition polymers of unsaturated esters | | |
| Polymethyl methacrylate | 9.3 | 19.0 |
| Polyethylmethacrylate | 9.1 | 18.6 |
| Polymethylacrylate | 9.7 | 19.8 |
| Polyethylacrylate | 9.2 | 18.8 |
| Hydrocarbon polymers | | |
| Polyethylene | 8.1 | 16.6 |
| Polystyrene | 9.1 | 18.6 |
| Polyisobutylene | 7.7 | 15.7 |
| Polyisoprene | 8.1 | 16.6 |
| Polybutadiene | 8.4 | 16.6 |
| Polyethylene/butylene | 7.9 | 16.2 |
| Halogen-containing polymers | | |
| Polytetrafluoroethylene | 6.2 | 12.7 |
| Polyvinylchloride | 9.5 | 19.4 |
| Polyvinylidene chloride | 12.2 | 24.9 |
| Polychloroprene | 9.4 | 19.2 |
| Polyacrylonitrile | 12.7 | 26.0 |
| Condensation polymers | | |
| Nylon-66 | 13.6 | 27.8 |
| Epon resin 1004 (epoxy) | 9.7 | 19.8 |
| Polysiloxanes | | |
| Polydimethylsiloxane Copolymers | 7.3 | 14.9 |
| Polybutadiene-co-acrylonitrile: 75/25 to 70/30 | 9.25 | 18.9 |
| Polybutadiene-co-styrene: 75/25 to 72/28 | 8.5 | 17.4 | excerpted from Kraton ® Thermoplastic Rubber Shell Chemical Co. Product Brochure Number SC: 198-89

Table I-B below sets forth solubility parameters calculated by Fedors' method and are expressed in units of $(J/cm^3)^{1/2}$.

TABLE I-B

| Components | Solubility Parameter $(J/cm^3)^{1/2}$ |
|---|---|
| ethylene/vinyl acetate (40% VAC) | 20.9 |
| polydimethylsiloxane | 15.1 |
| polyisobutylene | 17.6 |
| polyethylene | 17.6 |
| polyethyl methacrylate | 19.8 |
| polyethyl acrylate | 20.9 |
| polymethyl acrylate | 21.7 |
| polymethyl methacrylate | 22.3 |
| polystyrene | 22.5 |
| nitroglycerin | 27.0 |
| estradiol | 24.5 |
| norethindrone acetate | 21.3 |
| pilocarpine | 22.9 |
| albuterol | 26.7 |

In accordance with the principles of the invention, the transdermal permeation rate is controlled by varying the polymer components of a ternary multiple polymer adhesive system so as to alter the difference in the solubility parameter of the multiple polymer adhesive system relative to that of the drug (see Examples 2–5, or 28 and 29, hereinbelow). The solubility parameters of a rubber-based pressure-sensitive adhesive and a polyacrylate polymer are different from one another by an increment of at least 2 $(J/cm^3)^{1/2}$. Most preferably they differ by at least 4 $(J/cm^3)^{1/2}$ The transdermal permeation rate is also controlled by varying the relative proportions of the polymers comprising the multiple polymer adhesive system (see Example 6 hereinbelow).

The multiple polymer adhesive system is preferably formulated so that it is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In general, the multiple polymer adhesive system should have a glass transition temperature ($T_g$), measured using a differential scanning calorimeter, of between about −70° C. and 0° C.

Selection of the particular polymer composition is governed in large part by the drug to be incorporated in the device, as well as the desired rate of delivery of the drug. Those skilled in the art can readily determine the rate of delivery of drugs from the multiple polymer adhesive system in order to select suitable combinations of polymers and drug for a particular application. Various techniques can be used to determine the rate of delivery of the drug from the polymer. Illustratively, the rate of delivery can be determined by measuring the transfer of drug from one chamber to another through cadaver skin over time, and calculating, from the obtained data, the drug delivery or flux rate.

In a particularly preferred embodiment of the invention, the multiple polymer adhesive system comprises a pressure-sensitive adhesive blend of an acrylic polymer, a silicone polymer, and a soluble PVP. The term "acrylic polymer" is used here as in the art interchangeably with "polyacrylate," "polyacrylic polymer," and "acrylic adhesive." The acrylic-based polymer and silicone-based polymer are preferably in a ratio by weight, respectively, from about 2:98 to about 96:4, more preferably from about 2:98 to about 90:10, and even more preferably about 2:98 to about 86:14. The amount of acrylic-based (hereinafter referred to broadly as a polyarylate) polymer and silicone-based polymer (hereinafter referred to broadly as a polysiloxane) is adjusted so as to modify the saturation concentration of the drug in the ternary multiple polymer adhesive system in order to affect the rate of delivery of the drug from the system and through the skin.

In other particularly improved embodiments of the invention, the polyacrylate polymer is present in an amount ranging from about 5–85% by weight of the composition and polyisobutylene is present in an amount ranging from about 14–94% by weight of the composition. In yet another preferred embodiment, the polyisobutylene is present in an amount ranging from about 10–90% by weight of said composition and the polysiloxane is present in an amount ranging from about 5–95% by weight of said composition.

The adjustment to the saturation concentration of the drug in the multiple polymer adhesive system can either be an increase or a decrease. It has been found that when a polyacrylate having a solubility parameter SP of about 21 $(J/cm^3)^{1/2}$ is used as the principal polymer of a nitroglycerin (SP about 27 $(J/cm^3)^{1/2}$) monolithic system, a significant increase in the transdermal permeation rate of nitroglycerin can be achieved by the addition of a polymer having a lower solubility parameter, for example a polysiloxane (SP about 15 $(J/cm^3)^{1/2}$). By reducing the "net" solubility parameter of the multiple polymer transdermal adhesive system, the difference between the solubility parameter of nitroglycerin and the multiple polymer adhesive system is modified. This solubility parameter difference results in a lower saturation concentration for nitroglycerin, and thereby a greater thermodynamic driving force. Conversely, the composition of the multiple polymer adhesive system can be selected so that the saturation concentration of the drug in the system is modified, so the rate of delivery is retarded, such as would be desirable for administration of scopolamine or nicotine.

Advantageously, the method and composition of the present invention permit selectable loading of the drug in the transdermal drug delivery system. The concentration by weight of the drug in the transdermal drug delivery system is preferably about 0.1 to about 50 percent, more preferably about 0.1 to about 40 percent, and even more preferably about 0.3 to about 30 percent, said percentages being based on the total weight of the transdermal drug delivery system. Irrespective of whether there is high-loading or low-loading of the drug into the transdermal drug delivery system, the pressure-sensitive adhesive composition of the present invention can be formulated to maintain acceptable shear, tack, and peel adhesive properties.

Although not wishing to be bound by theory, particularly in this case where the structure of the composition has not been analyzed, it is postulated that the polymers of varying solubility parameters, for example, the polysiloxane and the polyacrylate, result in a heterogenous mix, with the components of the polymeric mixture performing as a mutually interpenetrating polymeric network in the composition. In other words, the multiple polymer adhesive system is a mixture of essentially mutually insoluble or immiscible polymers, in contradistinction to the typical prior art transdermal drug delivery systems derived from a single polymer or a solution of mutually soluble polymers.

In the practice of preferred embodiments of the invention, the polyacrylate polymer can be any of the homopolymers, copolymers, terpolymers, and the like of various acrylic acids. In such preferred embodiments, the polyacrylate polymer constitutes preferably from about 2% to about 95% of the total weight of the total polymer blend, and preferably about 3% to about 90%, and more preferably about 5% to about 85%, the amount of polyacrylate polymer being dependent on the amount and type of drug used.

The acrylate polymers useful in practicing the invention are polymers of one or more monomers of acrylic acids and other copolymerizable monomers. The acrylate polymers also include copolymers of alkyl acrylates and/or methacrylates and/or copolymerizable secondary monomers or monomers with functional groups. By varying the amount of each type of monomer added, the cohesive properties of the resulting acrylate polymer can be changed as is known in the art. In general, the acrylate polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

Further details and examples of acrylic adhesives which are suitable in the practice of the invention are described in Satas, "Acrylic Adhesives," *Handbook of Pressure-Sensitive Adhesive Technology 2nd ed.,* pp. 396–456 (D. Satas, ed.), Van Nostrand Reinhold, New York (1989).

Suitable acrylic adhesives are commercially available and include the polyacrylate adhesives sold under the trademarks Duro-Tak 80-1194, Duro-Tak 80-1196, and Duro-Tak 80-1197 by National Starch and Chemical Corporation, Bridgewater, N.J. Other suitable acrylic adhesives are those sold under the trademarks Gelva-Multipolymer Solution (GMS) 737 or 788 (Monsanto; St. Louis, Mo.).

The rubber-based pressure-sensitive adhesives useful in practicing the invention include hydrocarbon polymers such as natural and synthetic polyisoprene, polybutylene and polyisobutylene, styrene/butadiene polymers styrene-isoprene-styrene block copolymers, hydrocarbon polymers such as butyl rubber, halogen-containing polymers such as polyacrylic-nitrile, polytetrafluoroethylene, polyvinylchloride, polyvinylidene chloride, and polychlorodiene, and polysiloxanes and other copolymers thereof.

Suitable polysiloxanes include silicone pressure-sensitive adhesives which are based on two major components: a polymer, or gum, and a tackifying resin. The polysiloxane adhesive is usually prepared by cross-linking the gum, typically a high molecular weight polydiorganosiloxane, with the resin, to produce a three-dimensional silicate structure, via a condensation reaction in an appropriate organic solvent. The ratio of resin to polymer is the most important factor which can be adjusted in order to modify the physical properties of polysiloxane adhesives. Sobieski, et al., "Silicone Pressure Sensitive Adhesives," *Handbook of Pressure-Sensitive Adhesive Technology, 2nd ed.,* pp. 508–517 (D. Satas, ed.), Van Nostrand Reinhold, New York (1989).

Further details and examples of silicone pressure sensitive adhesives which are useful in the practice of this invention are described in the following U.S. Patents: U.S. Pat. Nos. 4,591,622; 4,584,355; 4,585,836; and 4,655,767.

Suitable silicone pressure-sensitive adhesives are commercially available and include the silicone adhesives sold under the trademarks BIO-PSA X7-3027, BIO-PSA X7-4503, BIO-PSA X7-4603, BIO-PSA X7-4301, BIO-PSA X7-4303, BIO-PSA X7-4919, BIO-PSA X7-2685, and BIO-PSA X7-3122 by Dow Corning Corporation, Medical Products, Midland, Mich. BIO-PSA-3027 is particularly suitable for use in formulations containing amine-functional drugs, such as albuterol.

In the practice of preferred embodiments of the invention, the polysiloxane constitutes preferably from about 9% to about 97% of the total weight of the total polymer blend, and preferably about 8% to about 97%, and more preferably about 14% to about 94%.

Exemplary of drugs that can be administered by the novel transdermal drug delivery system of this invention include, but are not limited to:

1. α-Adrenergic agonists such as Adrafinil, Adrenolone, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine Hydrochloride, Methylhexaneamine, Metizolene, Midodrine, Naphazoline, Norepinephrine, Norfenefrine, Octodrine, Octopamine, Oxymetazoline, Phenylephrine Hydrochloride, Phenylpropanolamine Hydrochloride, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine and Xylometazoline.

2. β-Adrenergic agonists such as Albuterol, Bambuterol, Bitolterol, Carbuterol, Clenbuterol, Clorprenaline, Denopamine, Dioxethedrine, Dopexamine, Ephedrine, Epinephrine, Etafedrine, Ethylnorepinephrine, Fenoterol, Formoterol, Hexoprenaline, Ibopamine, Isoetharine, Isoproterenal, Mabuterol, Metaproterenol, Methoxyphenamine, Oxyfedrine, Pirbuterol, Prenalterol, Procaterol, Protokylol, Reproterol, Rimiterol, Ritodrine, Soterenol, Terbuterol and Xamoterol.

3. α-Adrenergic blockers such as Amosulalol, Arotinolol, Dapiprazole, Doxazosin, Ergoloid Mesylates, Fenspiride, Indoramin, Labetalol, Nicergoline, Prazosin, Terazosin, Tolazoline, Trimazosin and Yohimbine.

4. β-Adrenergic blockers such as Acebutolol, Alprenolol, Amosulalol, Arotinolol, Atenolol, Befunolol, Betaxolol, Bevantolol, Bisoprolol, Bopindolol, Bucumolol, Befetolol, Bufuralol, Bunitrolol, Bupranolol, Butidrine Hydrochloride, Butofilolol, Carazolol, Carteolol, Carvedilol, Celiprolol, Cetamolol, Cloranolol, Dilevalol, Epanolol, Esmolol, Indenolol, Labetalol, Levobunolol, Mepindolol, Metipranalol, Metoprolol, Moprolol, Nadoxolol, Nifenalol, Nipradilol, Oxprenolol, Penbutolol, Pindolol, Practolol, Pronethalol, Propranolol, Sotalol, Sulfinalol, Talinolol, Tertatolol, Timolol, Toliprolol and Xibenolol.

5. Alcohol deterrents such as Calcium Cyanamide Citrated, Disulfiram, Nadide and Nitrefazole.

6. Aldose reductase inhibitors such as Epalrestat, Ponalrestat, Sorbinil and Tolrestat.

7. Anabolics such as Androisoxazole, Androstenediol, Bolandiol, Bolasterone, Clostebol, Ethylestrenol. Formyldienolone, 4-Hydroxy-19-nortestosterone, Methandriol, Methenolone, Methyltrienolone, Nandrolone, Nandrolone Decanoate, Nandrolone p-Hexyloxyphenylpropionate, Nandrolone Phenpropionate, Norbolethone, Oxymesterone, Pizotyline, Quinbolone, Stenbolone and Trenbolone.

8. Analgesics (dental) such as Chlorobutanol, Clove and Eugenol.

9. Analgesics (narcotic) such as Alfentanil, Allylprodine, Alphaprodine, Anileridine, Benzylmorphine, Bezitramide, Buprenorphine, Butorphanol, Clonitazene, Codeine, Codeine Methyl Bromide, Codeine Phosphate, Codeine Sulfate, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl Butyrate, Dipipanone, Eptazocine, Ethoheptazine, Ethylmethlythiambutene, Ethylmorphine, Etonitazene, Fentanyl, Hydrocodone, Hydromorphone, Hydroxypethidine, Isomethadone, Ketobemidone, Levorphanol, Lofentanil, Meperidine, Meptazinol, Metazocine, Methadone Hydrochloride, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papaveretum, Pentazocine, Phenadoxone, Phenazocine, Pheoperidine, Piminodine, Piritramide, Proheptazine, Promedol, Properidine, Propiram, Propoxyphene, Sufentanil and Tilidine.

10. Analgesics (non-narcotic) such as Acetaminophen, Acetaminosalol, Acetanilide, Acetylsalicylsalicylic Acid, Alclofenac, Alminoprofen, Aloxiprin, Aluminum Bis (acetylsalicylate), Aminochlorthenoxazin, 2-Amino-4-picoline, Aninopropylon, Aminopyrine, Ammonium Salicylate, Antipyrine, Antipyrine Salicylate, Antrafenine, Apazone, Aspirin, Benorylate, Benoxaprofen, Benzpiperylon, Benzydamine, p-Bromoacetanilide, 5-Bromosalicylic Acid Acetate, Bucetin, Bufexamac, Bumadizon, Butacetin, Calcium Acetylsalicylate, Carbamazepine, Carbetidine, Carbiphene, Carsalam, Chloralantipyrine, Chlorthenoxazin(e), Choline Salicylate, Cinchophen, Ciramadol, Clometacin, Cropropamide, Crotethamide, Dexoxadrol, Difenamizole, Diflunisal, Dihydroxyaluminum Acetylsalicylate, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Magnesium Acetylsalicylate, Methotrimeprazine, Metofoline, Miroprofen, Morazone, Morpholine Salicylate, Naproxen, Nefopam, Nifenazone, 5' Nitro-2' propoxyacetanilide, Parsalmide, Perisoxal, Phenacetin, Phenazopyridine Hydrochloride, Phenocoll, Phenopyrazone, Phenyl Acetylsalicylate, Phenyl Salicylate, Phenyramidol, Pipebuzone, Piperylone, Prodilidine, Propacetamol, Propyphenazone, Proxazole, Quinine Salicylate, Ramifenazone, Rimazolium Metilsulfate, Salacetamide, Salicin, Salicylamide, Salicylamide O-Acetic Acid, Salicylsulfuric Acid, Salsalte, Salverine, Simetride, Sodium Salicylate, Sulfamipyrine, Suprofen, Talniflumate, Tenoxicam, Terofenamate, Tetradrine, Tinoridine, Tolfenamic Acid, Tolpronine, Tramadol, Viminol, Xenbucin and Zomepirac.

11. Androgens such as Boldenone, Fluoxymesterone, Mestanolone, Mesterolone, Methandrostenolone, 17-Methyltestosterone, 17α-Methyltestosterone 3-Cyclopentyl Enol Ether, Norethandrolone, Normethandrone, Oxandrolone, Oxymesterone, oxymetholone, Prasterone, Stanlolone, Stanozolol, Testosterone, Testosterone 17-Chloral Hemiacetal, Testosterone 17β-Cypionate, Testosterone Enanthate, Testosterone Nicotinate, Testosterone Pheynylacetate, Testosterone Propionate and Tiomesterone.

12. Anesthetics (intravenous) such as Acetamidoeugenol, Alfadolone Acetate, Alfaxalone, Amucaine, Amolanone, Amylocaine Hydrochloride, Benoxinate, Betoxycaine, Biphenamine, Bupivacaine, Butacaine, Butaben, Butanilicaine, Burethamine, Buthalital Sodium, Butoxycaine, Carticaine, 2-Chloroprocaine Hydrochloride, Cocaethylene, Cocaine, Cyclomethycaine, Dibucaine Hydrochloride, Dimethisoquin, Dimethocaine, Diperadon Hydrochloride, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine Hydrochloride, Hydroxydione Sodium, Hydroxyprocaine, Hydroxytetracaine, Isobutyl p-Aminobenzoate, Kentamine, Leucinocaine Mesylate, Levoxadrol, Lidocaine, Mepivacaine, Meprylcaine Hydrochloride, Metabutoxycaine Hydrochloride, Methohexital Sodium, Methyl Chloride, Midazolam, Myrtecaine, Naepaine, Octacaine, Orthocaine, Oxethazaine, Parethoxycaine, Phenacaine Hydrochloride, Phencyclidine, Phenol, Piperocaine, Piridocaine, Polidocanol, Pramoxine, Prilocaine, Procaine, Propanidid, Propanocaine, Proparacaine, Propipocaine, Propofol, Propoxycaine Hydrochloride, Pseudococaine, Pyrrocaine, Quinine Urea Hydochloride, Risocaine, Salicyl Alcohol, Tetracaine Hydrochloride, Thialbarbital, Thimylal, Thiobutabarbital, Thiopental Sodium, Tolycaine, Trimecaine and Zolamine.

13. Anorectics such as Aminorex, Amphecloral, Amphetamine, Benzaphetamine, Chlorphentermine, Clobenzorex, Cloforex, Clortermine, Cyclexedrine, Destroamphetamine Sulfate, Diethylpropion, Diphemethoxidine, N-Ethylamphetamine, Fenbutrazate, Fenfluramine, Fenproporex, Furfurylmethylamphetamine, Levophacetoperate, Mazindol, Mefenorex, Metamfeproamone, Methamphetamine, Norpseudoephedrine, Phendimetrazine, Phenmetrazine, Phenpentermine, Phenylpropanolamine Hydrochloride and Picilorex.

14. Anthelmintics (Cestodes) such as Arecoline, Aspidin, Aspidinol, Dichlorophen(e), Embelin, Kosin, Napthalene, Niclosamide, Pellertierine, Pellertierine Tannate and Quinacrine.

15. Anthelmintics (Nematodes) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4-Hexylresorcinol, Kainic Acid, Mebendazole, 2-Napthol, Oxantel, Papain, Piperazine, Piperazine Adipate, Piperazine Citrate, Piperazine Edetate Calcium, Piperazine Tartrate, Pyrantel, Pyrvinium Pamoate, α-Santonin, Stilbazium Iodide, Tetrachloroethylene, Tetramisole, thiabendazole, Thymol, Thymyl N-Isoamylcarbamate, Triclofenol Piperazine and Urea Stibamine.

16. Anthelmintics (Onchocerca) such as Ivermectin and Suramin Sodium.

17. Anthelmintics (Schistosoma) such as Amoscanate, Amphotalide, Antimony Potassium Tartrate, Antimony Sodium Gluconate, Antimony Sodium Tartrate, Antimony Sodium Thioglycollate, Antimony Thioglycollamide, Becanthone, Hycanthone, Lucanthone Hydrochloride, Niridazole, oxamniquine, Praziquantel, Stibocaptate, Stibophen and Urea Stibamine.

18. Anthelmintic (Trematodes) such as Anthiolimine and Tetrachloroethylene.

19. Antiacne drugs such as Algestone Acetophenide, Azelaic Acid, Benzoyl Peroxide, Cyoctol, Cyproterone, Motretinide, Resorcinol, Retinoic Acid and Tetroquinone.

20. Antiallergics such as Amlexanox, Astemizole, Azelastine, Cromolyn, Fenpiprane, Histamine, Ibudilast, Nedocromil, Oxatomide, Pentigetide, Poison Ivy Extract, Poison Oak Extract, Poison Sumac Extract, Repirinast, Tranilast, Traxanox and Urushiol.

21. Antiamebics such as Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Dephetarsone, Emetine, Fumagillin, Glaucarubin, Glycobiarsol, 8-Hydroxy-7-iodo-5-quinolinesulfonic Acid, Iodochlorhydroxyquin, Iodoquinol, Paromomycin, Phanquinone, Phearsone Sulfoxylate, Polybenzarsol, Propamidine, Quinfamide, Secnidazole, Sulfarside, Teclozan, Tetracycline, Thiocarbamizine, Thiocarbarsone and Tinidazole.

22. Antiandrogens such as Bifluranol, Cyoctol, Cyproterone, Delmadinone Acetate, Flutimide, Nilutamide and Oxendolone.

23. Antianginals such as Acebutolol, Alprenolol, Amiodarone, Amlodipine, Arotinolol, Atenolol, Bepridil, Bevantolol, Bucumolol, Bufetolol, Bufuralol, Bunitrolol, Bupranolol, Carozolol, Carteolol, Carvedilol, Celiprolol, Cinepazet Maleate, Diltiazem, Epanolol, Felodipine, Gallopamil, Imolamine, Indenolol, Isosorbide Dinitrate, Isradipine, Limaprost, Mepindolol, Metoprolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutolol, Pentaerythritol Tetranitrate, Pindolol, Pronethalol, Propranolol, Sotalol, Terodiline, Timolol, Toliprolol and Verapamil.

24. Antiarrhythmics such as Acebutol, Acecaine, Adenosine, Ajmaline, Alprenolol, Amiodarone, Amoproxan, Aprindine, Arotinolol, Atenolol, Bevantolol, Bretylium Tosylate, Bubumolol, Bufetolol, Bunaftine, Bunitrolol, Bupranolol, Butidrine Hydrochloride, Butobendine, Capobenic Acid, Carazolol, Carteolol, Cifenline, Cloranolol, Disopyramide, Encainide, Esmolol, Flecainide, Gallopamil, Hydroquinidine, Indecainide, Indenolol, Ipratropium Bromide, Lidocaine, Lorajmine, Lorcainide, Meobentine, Metipranolol, Mexiletine, Moricizine, Nadoxolol, Nifenalol, Oxprenolol, Penbutolol, Pindolol, Pirmenol, Practolol, Prajmaline, Procainamide Hydrochloride, Pronethalol, Propafenone, Propranolol, Pyrinoline, Quinidine Sulfate, Quinidine, Sotalol, Talinolol, Timolol, Tocainide, Verapamil, Viquidil and Xibenolol.

25. Antiarteriosclerotics such as Pyridinol Carbamate.

26. Antiarthritic/Antirheumatics such as Allocupreide Sodium, Auranofin, Aurothioglucose, Aurothioglycanide, Azathioprine, Calcium 3-Aurothio-2-propanol-1-sulfonate, Chloroquine, Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Methotrexate, Myoral and Penicillamine.

27. Antibacterial (antibiotic) drugs including:

Aminoglycosides such as Amikacin, Apramycin, Arbekacin, Bambermycins, Butirosin, Dibekacin, Dihdrostreptomycin, Fortimicin(s), Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols such as Azidamfenicol, Chloramphenicol, Chloramphenicol Palmitate, Chloramphenicol Pantothenate, Florfenicol and Thiamphenicol;

Ansamycins such as Rifamide, Rifampin, Rifamycin and Rifaximin;

β-Lactams, including:

Carbapenems such as Imipenem;

Cephalosporins such as Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonam;

Oxacephems such as Flomoxef and Moxolactam;

Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin Sodium, Carbenicillin, Carfecillin Sodium, Carindacillin, Clometocillin, Cloxacillin, Cyclacillin, Dicloxacillin, Diphenicillin Sodium, Epicillin, Fenbenicillin, Floxicillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillen N, Penicillin O, Penicillin V, Penicillin V Benzathine, Penicillin V Hydrabamine, Penimepicycline, Phenethicillin Potassium, Piperacillin, Pivapicillin, Propicillin, Quinacillin, Sulbenicillin, Talampicillin, Temocillin and Ticarcillin;

Lincosamides such as Clindamycin and Lincomycin;

Macrolides such as Azithromycin, Carbomycin, Clarithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin;

Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and other antibiotics such as Cycloserine, Mupirocin and Tuberin.

28. Antibacterial drugs (synthetic), including:

2,4-Diaminopyrimidines such as Brodimoprim, Tetroxoprim and Trimethoprim;

Nitrofurans such as Furaltadone, Furazolium Chloride, Nifuradene, Nifuratel, Nifurfoline, Nifurpirinol, Nifurprazine, Nifurtoinol and Nitrofurantoin;

Quinolones and Analogs such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N^2$Formylsulfisomidine, $N^2$-β-D-Glucosylsulfanilamide, Mafenide, 4'-(Methylsulfamoyl) sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethanesulfonic Acid Triethanolamine Salt, 4-Sulfanilamidosalicylic Acid, $N^4$-Sulfanilylsulfanilamide, Sulfanilylurea, N-Sulfanilyl-3,4-xylamide, Sulfanitran, Sulfaperine, Sulfaphenazole. Sulfaproxyline, Sulfapyrazine, Sulfapyridine, Sulfasomizole, Sulfasymazine, Sulfathiazole, Sulfathiourea, Sulfatolamide, Sulf isomidine and Sulfisoxazole;

Sulfones such as Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, p,p'-Sulfonyldianiline-N.N' digalactoside, Sulfoxone Sodium and Thiazolsulfone; and others such as Clofoctol, Hexedine, Methenamine, Methenamine Anhydromethylene-citrate, Methenamine Hippurate, Methenamine Mandelate, Methenamine Sulfosalicylate, Nitroxoline and Xibornol.

29. Anticholinergics such as Adiphenine Hydrochloride, Alverine, Ambutonomium Bromide, Aminopentamide, Amixetrine, Amprotropine Phosphate, Anisotropine Methylbromide, Apoatropine, Atropine, Atropine N-Oxide, Benactyzine, Benapryzine, Benzetimide, Benzilonium Bromide, Benztropine Mesylate, Bevonium Methyl Sulfate, Biperiden, Butropium Bromide, N-Butylscopolammonium Bromide, Buzepide, Camylofine, Caramiphen Hydrochloride, Chlorbenzoxamine, Chlorphenoxamine, Cimetropium Bromide, Clidinium Bromide, Cyclodrine, Cyclonium Iodide, Cycrimine Hydrochloride, Deptropine, Dexetimide, Dibutoline Sulfate, Dicyclomine Hydrochloride, Diethazine, Difemerine, Dihexyverine, Diphemanil Methylsulfate, N-(1,2-Diphenylethyl) nicotinamide, Dipiproverine, Diponium Bromide, Emepronium Bromide, Endobenzyline Bromide, Ethopropazine, Ethybenztropine, Ethylbenzhydramine, Etomidoline, Eucatropine, Fenpiverinium Bromide, Fentonium Bromide, Flutropium Bromide, Glycopyrrolate, Heteronium Bromide, Hexocyclium Methyl Sulfate, Homatropine, Hyoscyamine, Ipratropium Bromide, Isopropamide, Levomepate, Mecloxamine, Mepenzolate Bromide, Metcaraphen, Methantheline Bromide, Methixene, Methscopolamine Bromide, Octamylamine, Oxybutynin Chloride, oxyphencyclimine, Oxyphenonium Bromide, Pentapiperide, Penthienate Bromide, Phencarbamide, Phenglutarimide, Pipenzolate Bromide, Piperidolate, Piperilate, Poldine Methysulfate, Pridinol, Prifinium Bromide, Procyclidine, Propantheline Bromide, Propenzolate, Propyromazine, Scopolamine, Scopolamine N-Oxide, Stilonium Iodide, Stramonium, Sultroponium, Thihexinol, Thiphenamil, Tiemonium Iodide, Timepidium Bromide, Tiquizium Bromide, Tridihexethyl Iodide, Trihexyphenidyl Hydrochloride, Tropacine, Tropenzile, Tropicamide, Trospium Chloride, Valethamate Bromide and Xenytropium Bromide.

30. Anticonvulsants such as Acetylpheneturide, Albutoin, Aloxidone, Aminoglutethimide, 4-Amino-3-hydroxybutyric Acid, Atrolactamide, Beclamide, Buramate, Calcium Bromide, Carbamazepine, Cinromide, Clomethiazole, Clonazepam, Decimemide, Diethadione, Dimethadione, Doxenitoin, Eterobarb, Ethadione, Ethosuximide, Ethotoin, Fluoresone, 5-Hydroxytryptophan, Lamotrigine, Magnesium Bromide, Magnesium Sulfate, Mephenytoin, Mephobarbital, Metharbital, Methetoin, Methsuximide, 5-Methyl-5-(3-phenanthryl)hydantoin, 3-Methyl-5-phenylhydantoin, Narcobarbital, Nimetazepam, Nitrazepam, Paramethadione, Phenacemide, Phenethabital, Pheneturide, Phenobarbital, Phenobarbital Sodium, Phensuximide, Phenylmethylbarbituric Acid, Phenytoin, Phethenylate Sodium, Potassium Bromide, Primidone, Progabide, Sodium Bromide, Solanum, Strontium Bromide, Suclofenide, Sulthiame, Tetrantoin, Trimethadione, Valproic Acid, Valpromide, Vigabatrin and Zonisamide.

31. Antidepressants, including:

Bicyclics such as Binedaline, Caroxazone, Citalopram, Dimethazan, Indalpine, Fencamine, Indeloxazine Hydrochloride, Nefopam, Nomifensine, Oxitriptan, Oxypertine, Paroxetine, Sertraline, Thiazesim, Trazodone and Zometapine;

Hydrazides/Hydrazines such as Benmoxine, Iproclozide, Iproniazid, Isocarboxazid, Nialamide, Octamoxin and Phenelzine;

Pyrrolidones such as Cotinine, Rolicyprine and Rolipram;

Tetracyclics such as Maprotiline, Metralindole, Mianserin and Oxaprotiline.

Tricyclics such as Adinazolam, Amitriptyline, Amitriptylinoxide, Amoxapine, Butriptyline, Clomipramine, Demexiptiline, Desipramine, Dibenzepin, Dimetracrine, Dothiepin, Doxepin, Fluacizine, Imipramine, Imipramine N-Oxide, Iprindole, Lofepramine, Melitracen, Metapramine, Nortriptyline, Noxiptilin, Opipramol, Pizotyline, Propizepine, Protriptyline, Quinupramine, Tianeptine and Trimipramine; and others such as Adrafinil, Benactyzine.

Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Hematoporphyrin, Hypercinin, Levophacetoperane, Medifoxamine, Minaprine, Moclobemide, Oxaflozane, Piberaline, Prolintane, Pyrisuccideanol, Rubidium Chloride, Sulpiride, Sultopride, Teniloxazine, Thozalinone, Tofenacin, Toloxatone, Tranylcypromine, L-Tryptophan, Viloxazine and Zimeldine.

32. Antidiabetics, including:

Biguanides such as Buformin, Metformin and Phenformin;

Hormones such as Glucagon, Insulin, Insulin Injection, Insulin Zinc Suspension, Isophane Insulin Suspension, Protamine Zinc Insulin Suspension and Zinc Insulin Crystals;

Sulfonylurea derivatives such as Acetohexamide, 1-Butyl-3-metanilylurea, Carbutamide, Chlorpropamide, Glibornuride, Gliclazide, Glipizide, Gliquidone, Glisoxepid, Glyburide, Glybuthiazol(e), Glybuzole, Glyhexamide, Glymidine, Glypinamide, Phenbutamide, Tolazamide, Tolbutamide and Tolcyclamide; and others such as Acarbose, Calcium Mesoxalate and Miglitol.

33. Antidiarrheal drugs such as Acetyltannic Acid, Albumin Tannate, Alkofanone, Aluminum Salicylates—Basic, Catechin, Difenoxin, Diphenoxylate, Lidamidine, Loperamide, Mebiquine, Trillium and Uzarin.

34. Antidiuretics such as Desmopressin, Felypressin, Lypressin, Ornipressin, Oxycinchophen, Pituitary-Posterior, Terlipressin and Vasopressin.

35. Antiestrogens such as Delmadinone Acetate, Ethamoxytriphetol, Tamoxifen and Toremifene.

36. Antifungal drugs (antibiotics), including:

Polyenes such as Amphotericin-B, Candicidin, Dermostatin, Filipin, Fungichromin, Hachimycin, Hamycin, Lucensomycin, Mepartricin, Natamycin, Nystatin, Pecilocin and Perimycin; and others such as Azaserine, Griseofulvin, oligomycins, Neomycin Undecylenate, Pyrrolnitrin, Siccanin, Tubercidin and Viridin.

37. Antifungal drugs (synthetic), including:

Allylamines such as Naftifine and Terbinafine;

Imidazoles such as Bifonazole, Butoconazole, Chlordantoin, Chlor=idazole, Cloconazole, Clotrimazole, Econazole, Enilconazole, Fenticonazole, Isoconazole, Ketoconazole, Miconazole, Omoconazole, Oxiconazole, Nitrate, Sulconazole and Tioconazole;

Triazoles such as Fluconazole, Itraconazole and Terconazole; and others such as Acrisorcin, Amorolfine, Biphenamine, Bromosalicylchloranilide, Buclosamide, Calcium Propionate, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Tricetin, Ujothion, Undecylenic Acid and Zinc Propionate.

38. Antiglaucoma drugs such as Acetazolamide, Befunolol, Betaxolol, Bupranolol, Carteolol, Dapiprazoke, Dichlorphenamide, Dipivefrin, Epinephrine, Levobunolol, Methazolamide, Metipranolol, Pilocarpine, Pindolol and Timolol.

39. Antigonadotropins such as Danazol, Gestrinone and Paroxypropione.

40. Antigout drugs such as Allopurinol, Carprofen, Colchicine, Probenecid and Sulfinpyrazone.

41. Antihistamines, including:

Alkylamine derivatives such as Acrivastine, Bamipine, Brompheniramine, Chlorpheniramine, Dimethindene, Metron S., Pheniramine, Pyrrobutamine, Thenaldine, Tolpropamine and Triprolidine;

Aminoalkyl ethers such as Bietanautine, Bromodiphenhydramine, Carbinoxamine, Clemastine, Diphenlypyraline, Doxylamine, Embrammine, Medrylamine, Mephenphydramine, p-Methyldiphenhydramine, Orphenadrine, Phenyltoloxamine, Piprinhydrinate and Setasine;

Ethylenediamine derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine Hydrochloride, Tripelennamine and Zolamine;

Piperazines such as Cetirizine, Chlorcyclizine, Cinnarizine, Clocinizine and Hydroxyzine;

Tricyclics, including:

Phenothiazines such as Ahistan, Etymemazine, Fenethazine, N-Hydroxyethylpromethazine Chloride, Isopromethazine, Mequitazine, Promethazine, Pyrathiazine and Thiazinamium Methyl Sulfate; and others such as Azatadine, Clobenzepam, Cyproheptadine, Deptropine, Isothipendyl, Loratadine and Prothipendyl; and other antihistamines such as Antazoline, Astemizole, Azelastine, Cetoxime, Clemizole, Clobenztropine, Diphenazoline, Diphenhydramine, Mebhydroline, Phenindamine, Terfenadine and Tritoqualine.

42. Antihyperlipoproteinemics, including:

Aryloxyalkanoic acid derivatives such as Beclorbrate, Bazafibrate, Binifibrate, Ciprofibrate, Clinofibrate, Clofibrate, Clofibric Acid, Etonfibrate, Fenofibrate, Gemfibrozil, Nicofibrate, Pirifibrate, Ronifibrate, Simfibrate and Theofibrate;

Bile acid sequesterants such as Cholestyramine Resin, Colestipol and Polidexide;

HMG CoA reductase inhibitors such as Lovastatin, Pravastatin Sodium and Simvastatin;

Nicotinic acid derivatives Aluminum Nicotinate, Acipimox, Niceritrol, Nicoclonate, Nicomol and Oxiniacic Acid;

Thyroid hormones and analogs such as Etiroxate, Thyropropic Acid and Thyroxine; and others such as Acifran, Azacosterol, Benfluorex, β-Benzalbutyramide, Carnitine, Chondroitin Sulfate, Clomestone, Detaxtran, Dextran Sulfate Sodium, 5,8,11,14,17-Eicosapentaenoic Acid, Eritadenine, Furazbol, Meglutol, Melinamide, Mytatrienediol, Ornithine, γ-Oryzanol, Pantethine, Penataerythritol Tetraacetate, α-Phenylbutyramide, Pirozadil, Probucol, α-Sitosterol, Sultosilic Acid, Piperazine Salt, Tiadenol, Triparanol and Xenbucin.

43. Antihypertensive drugs, including:

Arylethanolamine derivatives such as Amosulalol, Bufuralol, Dilevalol, Labetalol, Pronethalol, Sotalol and Sulfinalol;

Aryloxypropanolamine derivatives such as Acebutolol, Alprenolol, Arotinolol, Atenolol, Betaxolol, Bevantolol, Bisoprolol, Bopindolol, Bunitrolol, Bupranolol, Butofilolol, Carazolol, Cartezolol, Carvedilol, Celiprolol, Cetamolol, Epanolol, Indenolol, Mepindolol, Metipranolol, Metoprolol, Moprolol, Nadolol, Nipradilol, Oxprenolol, Penbutolol, Pindolol, Propranolol, Talinolol, Tetraolol, Timolol and Toliprolol;

Benzothiadiazine derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, Paraflutizide, Polythiazide, Tetrachlormethiazide and Trichlormethiazide;

N-Carboxyalkyl (peptide/lactam) derivatives such as Alacepril, Captopril, Cilazapril, Delapril, Enalapril, Enalaprilat, Fosinopril, Lisinopril, Moveltipril, Perindopril, Quinapril and Ramipril;

Dihydropyridine derivatives such as Amlodipine, Felodipine, Isradipine, Nicardipine, Nifedipine, Nilvadipine, Nisoldipine and Nitrendipine;

Guanidine derivatives such as Bethanidine, Debrisoquin, Guanabenz, Guanacline, Guanadrel, Guanazodine, Guanethidine, Guanfacine, Guanochlor, Guanoxabenz and Guanoxan;

Hydrazines and phthalazines such as Budralazine, Cadralazine, Dihydralazine, Endralazine, Hydragarbazine, Hydralazine, Pheniprazine, Pildralazine and Todralazine;

Imidazole derivatives such as Clonidine, Lofexidine, Phentolamine, Tiamenidine and Tolonidine;

Quaternary ammonium compounds Azamethonium Bromide, Chlorisondamine Chloride, Hexamethonium, Pentacynium Bis(methyl sulfate), Pentamethonium Bromide, Pentolinium Tartate, Phenactopinium Chloride and Trimethidiunum Methosulfate;

Quinazoline derivatives such as Alfuzosin, Bunazosin, Doxazosin, Prasosin, Terazosin and Trimazosin;

Reserpine derivatives such as Bietaserpine, Deserpidine, Rescinnamine, Reserpine and Syrosingopine;

Sulfonamide derivatives such as Ambuside, Clopamide, Furosemide, Indapamide, Quinethazone, Tripamide and Xipamide; and others such as Ajmaline, γ-Aminobutyric Acid, Bufeniode, Chlorthalidone, Cicletaine, Ciclosidomine, Cryptenamine Tannates, Fenoldopam, Flosequinan, Indoramin, Ketanserin, Metbutamate, Mecamylamine, Methyldopa, Methyl 4-Pyridyl Ketone Thiosemicarbarzone, Metolazone, Minoxidil, Muzolimine, Pargyline, Pempidine, Pinacidil, Piperoxan, Primaperone, Protoveratrines, Raubasine, Rescimetol, Rilmenidene, Saralasin, Sodium Nitroprusside, Ticrynafen, Trimethaphan Camsylate, Tyrosinase and Urapidil.

44. Antihyperthyroids such as 2-Amino-4-methylthiazole, 2-Aminothiazole, Carbimazole, 3,5-Dibromo-L-tyrosine, 3,5-Diiodotyrosine, Hinderin, Iodine, Iothiouracil, Methimazole, Methylthiouracil, Propylthiouracil, Sodium Perchlorate, Thibenzazoline, Thiobarbital and 2-Thiouracil.

45. Antihypotensive drugs such as Amezinium Methyl Sulfate, Angiotensin Amide, Dimetofrine, Dopamine, Etifelmin, Etilefrin, Gepefrine, Metaraminol, Midodrine, Norepinephrine, Pholedrinead and Synephrine.

46. Antihypothyroid drugs such as Levothyroxine Sodium, Liothyronine, Thyroid, Thyroidin, Thyroxine, Tiratricol and TSH.

47. Anti-Inflammatory (non-steroidal) drugs, including:
    Aminoarylcarboxylic acid derivatives such as Enfenamic Acid, Etofenamate, Flufenamic Acid. Isonixin, Meclofenamic Acid, Mefanamic Acid, Niflumic Acid, Talniflumate, Terofenamate and Tolfenamic Acid;
    Arylacetic acid derivatives such as Acemetacin, Alclofenac, Amfenac, Bufexamac, Cinmetacin, Clopirac, Diclofenac Sodium, Etodolac, Felbinac, Fenclofenac, Fenclorac, Fenclozic Acid, Fentiazac, Glucametacin, Ibufenac, Indomethacin, Isofezolac, Isoxepac, Lonazolac, Metiazinic Acid, Oxametacine, Proglumetacin, Sulindac, Tiaramide, Tolmetin and Zomepirac;
    Arylbutyric acid derivatives such as Bumadizon, Butibufen, Fenbufen and Xenbucin;
    Arylcarboxylic acids such as Clidanac, Ketorolac and Tinoridine;
    Arylpropionic acid derivatives such as Alminoprofen, Benoxaprofen, Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Pirprofen, Pranoprofen, Protizinic Acid, Suprofen and Tiaprofenic Acid;
    Pyrazoles such as Difenamizole and Epirizole;
    Pyrazolones such as Apazone, Benzpiperylon, Feprazone, Mofebutazone, Morazone, Oxyphenbutazone, Phenybutazone, Pipebuzone, Propyphenazone, Ramifenazone, Suxibuzone and Thiazolinobutazone;
    Salicylic acid derivatives such as Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, 1-Naphthyl Salicylate, Olsalazine, Parsalmide, Phenyl Acetylsalicylate, Phenyl Salicylate, Salacetamide, Salicylamine O-Acetic Acid, Salicylsulfuric Acid, Salsalate and Sulfasalazine;
    Thiazinecarboxamides such as Droxicam, Isoxicam, Piroxicam and Tenoxicam; and
    others such as ε-Acetamidocaproic Acid, S-Adenosylmethionine, 3-Amino-4-hydroxybutyric Acid, Amixetrine, Bendazac, Benzydamine, Bucolome, Difenpiramide, Ditazol, Emorfazone, Guaiazulene, Nabumetone, Nimesulide, Orgotein, Oxaceprol, Paranyline, Perisoxal, Pifoxime, Proquazone, Proxazole and Tenidap.

48. Antimalarial drugs such as Acedapsone, Amodiaquin, Arteether, Artemether, Artemisinin, Artesunate, Bebeerine, Berberine, Chirata, Chlorguanide, Chloroquine, Chlorproguanil, Cinchona, Cinchonidine, Cinchonine, Cycloguanil, Gentiopicrin, Halofantrine, Hydroxychloroquine, Mefloquine Hydrochloride, 3-Methylarsacetin, Pamaquine, Plasmocid, Primaquine, Pyrimethamine, Quinacrine, Quinine, Quinine Bisulfate, Quinine Carbonate, Quinine Dihydrobromide, Quinine Dihydrochloride, Quinine Ethylcarbonate, Quinine Formate, Quinine Gluconate, Quinine Hydriodide, Quinine Hydrochloride, Quinine Salicylate, Quinine Sulfate, Quinine Tannate, Quinine Urea Hydrochloride, Quinocide, Quinoline and Sodium Arsenate Diabasic.

49. Antimigraine drugs such as Alpiropride, Dihydroergotamine, Ergocornine, Ergocorninine, Ergocryptine, Ergot, Ergotamine, Flumedroxone acetate, Fonazine, Lisuride, Methysergid(e), Oxetorone, Pizotyline and Sumatriptan.

50. Antinauseant drugs such as Acetylleucine Monoethanolamine, Alizapride, Benzquinamide, Bietanautine, Bromopride, Buclizine, Chlorpromazine, Clebopride, Cyclizine, Dimenhydrinate, Dipheniodol, Domperidone, Granisetron, Meclizine, Methalltal, Metoclopramide, Metopimazine, Nabilone, Ondansteron, Oxypendyl, Pipamazine, Piprinhydrinate, Prochlorperazine, Scopolamine, Tetrahydrocannabinols, Thiethylperazine, Thioproperzaine and Trimethobenzamide.

51. Antineoplastic drugs, including:
    Alkylating agents, including:
        Alkyl sulfonates such as Busulfan, Improsulfan and Piposulfan;
        Aziridines such as Benzodepa, Carboquone, Meturedepa and Uredepa;
        Ethylenimines and methylmelamines such as Altretamine, Triethylenemelamine, Triethylenephosphoramide Triethylenethiophosphoramide and Trimethylolomelamine;
        Nitrogen mustards such as Chlorambucil, Chlornaphazine, Chclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard;
        Nitrosoureas such as Carmustine, Chlorozotocin, Fotemustine, Lomustine, Nimustine and Ranimustine; and
        others such as Dacarbazine, Mannomustine, Mitobronitol, Mitolactol and Pipobroman;
    Antibiotics such as Aclacinomycins, Actinomycin $F_1$, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tubercidin, Ubenimex, Zinostatin and Zorubicin;

Antimetabolites including:
Folic acid analogs such as Denopterin, Methotrexate, Pteropterin and Trimetrexate;
Purine analogs such as Fludarabine, 6-Mercaptopurine, Thiamiprine and Thioguanaine; and
Pyrimidine analogs such as Ancitabine, Azacitidine, 6-Azauridine, Carmofur, Cytarabine, Doxifluridine, Enocitabine, Floxuridine, Fluroouracil and Tegafur; Enzymes such as L-Asparaginase; and
others such as Aceglatone, Amsacrine, Bestrabucil, Bisantrene, Carboplatin, Cisplatin, Defofamide, Demecolcine, Diaziguone, Elfornithine, Elliptinium Acetate, Etoglucid, Etoposide, Gallium Nitrate, Hydroxyurea, Interferon-α, Interferon-β, Interferon-γ, Interleukine-2, Lentinan, Lonidamine, Mitoguazone, Mitoxantrone, Mopidamol, Nitracrine, Pentostatin, Phenamet, Pirarubicin, Podophyllinicc Acid, 2-Ethythydrazide, Procarbazine, PSK®, Razoxane, Sizofiran, Spirogermanium, Taxol, Teniposide, Tenuazonic Acid, Triaziquone, 2,2', 2"-Trichlorotriethylamine, Urethan, Vinblastine, Vincristine and Vindesine;

52. Antineoplastic (hormonal) drugs, including:
Androgens such as Calusterone, Dromostanolone Propionate, Epitiostanol, Mepitiostane and Testolactone;
Antiadrenals such as Aminoglutethimide, Mitotane and Trilostane;
Antiandrogens such as Flutamide and Nilutamide; and
Antiestrogens such as Tamoxifen and Toremifene.

53. Antineoplastic adjuncts including folic acid replenishers such as Frolinic Acid.

54. Antiparkinsonian drugs such as Amantadine, Benserazide, Bietanautine, Biperiden, Bromocriptine, Budipine, Carbidopa, Deprenyl, Dexetimide, Diethazine, Droxidopa, Ethopropazine, Ethylbenzhydramine, Levodopa, Naxagolide, Pergolide, Piroheptine, Pridinol, Prodipine, Terguride, Tigloidine and Trihexyphenidyl Hydrochloride.

55. Antipheochromocytoma drugs such as Metyrosine, Phenoxybenzamine and Phentolamine.

56. Antipneumocystis drugs such as Effornithine, Pentamidine and Sulfamethoxazole.

57. Antiprostatic hypertrophy drugs such as Gestonorone Caproate, Mepartricin, Oxendolone and Proscar®.

58. Antiprotozoal drugs (Leshmania) such as Antimony Sodium Gluconate, Ethylstibamine, Hydroxystilbamidine, N-Methylglucamine, Pentamidine, Stilbamidine and Urea Stibamine.

59. Antiprotozoal drugs (Trichomonas) such as Acetarsone, Aminitrozole, Anisomycin, Azanidazole, Forminitrazole, Furazolidone, Hachimycin, Lauroguadine, Mepartricin, Metronidazole, Nifuratel, Nifuroxime, Nimorazole, Secnidazole, Silver Picrate, Tenonitrozole and Tinidazole.

60. Antiprotozoal drugs (Trypanosma) such as Benznidazole, Eflornithine, Melarsoprol, Nifurtimox, oxophenarsine, Hydrochloride, Pentamidine, Propamidine, Puromycin, Quinapyramine, Stilbamidine, Suramin Sodium, Trypan Red and Tryparasmide.

61. Antipuritics such as Camphor, Cyproheptadine, Dichlorisone, Glycine, Halometasone, 3-Hydroxycamphor, Menthol, Mesulphen, Methdilazine, Phenol, Polidocanol, Risocaine, Spirit of Camphor, Thenaldine, Tolpropamine and Trimeprazine.

62. Antipsoriatic drugs such as Acitretin, Ammonium Salicylate, Anthralin, 6-Azauridine, Bergapten(e), Chrysarobin, Etretinate and Pyrogallol.

63. Antipsychotic drugs, including:
Butyrophenones such as Benperidol, Bromperidol, Droperidol, Fluanisone, Haloperidol, Melperone, Moperone, Pipamperone, Sniperone, Timiperone and Trifluperidol;
Phenothiazines such as Acetophenazine, Butaperazine, Carphenazine, Chlorproethazine, Chlorpromazine, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine and Triflupromazine;
Thioxanthenes such as Chlorprothixene, Clopenthixol, Flupentixol and Thiothixene;
other tricyclics such as Benzquinamide, Carpipramine, Clocapramine, Clomacran, Clothiapine, Clozapine, Opipramol, Prothipendyl, Tetrabenazine, and Zotepine; and
others such as Alizapride, Amisulpride, Buramate, Fluspirilene, Molindone, Penfluridol, Pimozide, Spirilene and Sulpiride.

64. Antipyretics such as Acetaminophen, Acetaminosalol, Acetanilide, Aconine, Aconite, Aconitine, Alclofenac, Aluminum Bis(acetylsalicylate), Aminochlorthenoxazin, Aminopyrine, Aspirin, Benorylate, Benzydamine, Berberine, p-Bromoacetanilide, Buf examac, Bumadizon, Calcium Acetysalicylate, Chlorthenoxazin(e), Choline Salicylate, Clidanac, Dihydroxyaluminum Acetylsalicylate, Dipyrocetyl, Dipyrone, Epirizole, Etersalate, Imidazole Salicylate, Indomethacin, Isofezolac, p-Lactophenetide, Lysine Acetylsalicylate, Magnesium Acetylsalicylate, Meclofenamic Acid, Morazone, Morpholine Salicylate, Naproxen, Nifenazone, 5'-Nitro-2'-propoxyacetanilide, Phenacetin, Phenicarbazide, Phenocoll, Phenopyrazone, Phenyl Acetylsalicylate, Phenyl Salicylate, Pipebuzone, Propacetamol, Propyphenazone, Ramifenazone, Salacetamide, Salicylamide O-Acetic Acid, Sodium Salicylate, Sulfamipyrine, Tetrandrine and Tinoridine.

65. Antirickettsial drugs such as p-Aminobenzoic Acid, Chloramphenicol, Chloramphenicol Palmitate, Chloramphenicol Pantothenate and Tetracycline.

66. Antiseborrheic drugs such as Chloroxine, 3-O-Lauroylpyridoxol Diacetate, Piroctone, Pyrithione, Resorcinol, Selenium Sulfides and Tioxolone.

67. Antiseptics, including:
Guanidines such as Alexidine, Ambazone, Chlorhexidine and Picloxydine;
Halogens and halogen compounds such as Bismuth Iodide Oxide, Bismuth Iodosubgallate, Bismuth Tribromophenate, Bornyl Chloride, Calcium Iodate, Chlorinated Lime, Cloflucarban, Flurosalan, Iodic Acid, Iodine, Iodine Monochloride, Iodine Trichloride, Iodoform, Methenamine Tetraiodine, Oxychlorosene, Povidone-Iodine, Sodium Hypochlorite, Sodium Iodate, Symclosene, Thymol Iodide, Triclocarban, Triclosan and Troclosene Potassium;

Mercurial compounds such as Hydragaphen, Meralein Sodium, Merbromin, Mercuric Chloride, Mercuric Chloride, Ammoniated, Mercuric Sodium p-Phenolsulfonate, Mercuric Succinimide, Mercuric Sulfide, Red, Mercurophen, Mercurous Acetate, Mercurous Chloride, Mercurous Iodide, Nitromersol, Potassium Tetraiodomercurate (II), Potassium Triiodomercurate(II) Solution, Thimerfonate Sodium and Thimerosal;

Nitrofurans such as Furazolidone, 2-(Methoxymethyl)-5-nitrofuran, Nidroxyzone, Nifuroxime, Nifurzide and Nitrofurazone;

Phenols such as Acetomeroctol, Bithionol, Cadmium Salicylate, Carvacrol, Chloroxylenol, Clorophene, Cresote, Cresol(s), p-Cresol, Fenticlor, Hexachlorophene, 1-Napthyl Salicylate, 2-Napthyl Salicylate, 2,4,6-Tribromo-m-cresol, and 3',4',5'-Trichlorosalicylanilide;

Quinolines such as Aminoquinuride, Benzoxiquine, Broxyquinoline, Chloroxine, Chlorquinaldol, Cloxyquin, Ethylhydrocupreine, Euprocin, Halquinol, Hydrastine, 8-Hydroxquinoline, 8-Hydroxquinoline Sulfate and Iodochlorhydroxyquin; and others such as Aluminum Acetate Solution, Aluminum Subacetate Solution, Aluminum Sulfate, 3-Amino-4-hydroxybutyric Acid, Boric Acid, Chlorhexidine, Chloroazodin, m-Cresyl Acetate, Cupric Sulfate, Dibromopropamidine, Ichthammol, Negatol®, Noxytiolin, Ornidazole, β-Propiolactone, α-Terpineol.

68. Antispasmodic drugs such as Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Fenpiprane, Fenpiverinium Bromide, Fentonium Bromide, Flavoxate, Flopropione, Gluconic Acid, Guaiactamine, Hydramitrazine, Hymecromone, Leiopyrrole, Mebeverine, Moxaverine, Nafiverine, octamylamine, Octaverine, Pentapiperide, Phenamacide Hydrochloride, Phloroglucinol, Pinaverium Bromide, Piperilate, Pipoxolan Hydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, Trifolium, Trimebutine, N,N-1Trimethyl-3,3-diphenyl-propylamine, Tropenzile, Trospium Chloride and Xenytropium Bromide.

69. Antithrombotic drugs such as Anagrelide, Argatroban, Cilostazol, Daltroban, Defibrotide, Enoxaparin, Fraxiparine®, Indobufen, Lamoparan, Ozagrel, Picotamide, Plafibride, Tedelparin, Ticlopidine and Triflusal.

70. Antitussive drugs such as Allocamide, Amicibone, Benproperine, Benzonatate, Bibenzonium Bromide, Bromoform, Butamirate, Butethamate, Caramiphen Ethanedisulfonate, Carbetapentane, Chlophedianol, Clobutinol, Cloperastine, Codeine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, α,α-Diphenyl-2-piperidinepropanol, Dropropizine, Drotebanol, Eprazinone, Ethyl Dibunate, Ethylmorphine, Fominoben, Guiaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine Hydrochloride, Racemethorphan, Taziprinone Hydrochloride, Tipepidine and Zipeprol.

71. Antiulcerative drugs such as Aceglutamide Aluminum Complex, ε-Acetamidocaproic Acid Zinc Salt, Acetoxolone, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Misoprostol, Nizatidine, Omeprazole, Ornoprostil, γ-Oryzanol, Pifarnine, Pirenzepine, Plaunotol, Ranitidine, Rioprostil, Rosaprostol, Rotraxate, Roxatidine Acetate, Sofalcone, Spizofurone, Sucralfate, Teprenone, Trimoprostil, Thrithiozine, Troxipide and Zolimidine.

72. Antiurolithic drugs such as Acetohydroxamic Acid, Allopurinol, Potassium Citrate and Succinimide.

73. Antivenin drugs such as Lyovac® Antivenin.

74. Antiviral drugs, including:

Purines and pyrimidinones such as Acyclovir, Cytarabine, Dideoxyadenosine, Dideoxycytidine, Dideoxyinosine, Edoxudine, Floxuridine, Ganciclovir, Idoxuridine, Inosine Pranobex, MADU, Trifluridine, Vidrarbine and Zidovudiine; and others such as Acetylleucine Monoethanolamine, Amantadine, Amidinomycin, Cuminaldehyde Thiosemicarbzone, Foscarnet Sodium, Interferon-α, Interferon-β, Interferon-γ, Kethoxal, Lysozyme, Methisazone, Moroxydine, Podophyllotoxin, Ribavirin, Rimantadine, Stallimycin, Statolon, Tromantadine and Xenazoic Acid.

75. Anxiolytic drugs, including:

Arylpiperazines such as Buspirone, Gepirone and Ipsapirone;

Benzodiazepine derivatives such as Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam and Tofisopam;

Carbamates such as Cyclarbamate, Emylcamate, Hydroxyphenamate, Meprobamate, Phenprobamate and Tybamate; and others such as Alpidem, Benzoctamine, Captodiamine, Chlormezanone, Etifoxine, Fluoresone, Glutamic Acid, Hydroxyzine, Mecloralurea, Mephenoxalone, Oxanamide, Phenaglycodol, Suriclone.

76. Benzodiazepine antagonists such as Flumazenil.

77. Bronchodilators, including:

Ephedrine derivatives such as Albuterol, Bambuterol, Bitolterol, Carbuterol, Clenbuterol, Clorprenaline, Dioxethedrine, Ephedrine, Epiniphrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Soterenol, Terbutaline and Tulobuterol;

Quaternary ammonium compounds such as Bevonium Methyl Sulfate, Clutropium Bromide, Ipratropium Bromide and Oxitropium Bromide;

Xanthine derivatives such as Acefylline, Acefylline Piperazine, Ambuphylline, Aminophylline, Bamifylline, choline Theophyllinate, Doxofylline, Dyphylline, Enprofylline, Etamiphyllin, Etofylline, Guaithylline, Proxyphylline, Theobromine, 1-Theobromineacetic Acid and Theophylline; and others such as Fenspiride, Medibazine, Methoxyphenanime and Tretoquinol.

78. Calcium channel blockers, including:

Arylalkylamines such as Bepridil, Ditiazem, Fendiline, Gallopanil, Prenylamine, Terodiline and Verapamil;

Dihydropyridine derivatives such as Felodipine, Isradipine, Nicardipine, Nifedipine, Nilvadipine, Nimodipine, Nisoldipine and Nitrendipine;

Piperazine derivatives such as Cinnarizine, Flunarisine and Lidoflazine; and others such as Bencyclane, Etafenone and Perhexiline.

79. Calcium regulators such as Calcifediol, Calcitonin, Calcitriol, Clodronic Acid, Dihydrotachysterol, Elcatonin, Etidronic Acid, Ipriflavone, Pamidronic Acid, Parathyroid Hormone and Teriparatide Acetate.

80. Cardiotonics such as Acefylline, Acetyldigititoxins, 2-Amino-4-picoline, Amrinone, Benfurodil Hemisuccinate, Buclasdesine, Cerberoside, Camphotamide, Convallatoxin, Cymarin, Denopamine, Deslanoside, Ditalin, Digitalis, Digitoxin, , Digoxin, Dobutamine, Dopamine, Dopexamine, Enoximone, Erythrophleine, Fenalcomine, Gitalin, Gitoxin, Glycocyamine, Heptaminol, Hydrastinine, Ibopamine, Lanotodises, Metamivam, Milrinone, Neriifolin, Oleandrin, Ouabain, Oxyfedrine, Prenalterol, Proscillaridin, Resibufogenin, Scillaren, Scillarenin, Strophanthin, Sulmazole, Theobromine and Xamoterol.

81. Chelating agents such as Deferozmine, Ditiocarb Sodium, Edetate Calcium Disodium, Edetate Disodium, Edeate Sodium, Edetate Trisodium, Penicillamine, Pentetate Calcium Trisodium, Pentectic Acid, Succimer and Trientine;

82. Cholecystokinin antagonists such as Proglumide.

83. Cholelitholytic agents such as Chenodiol, Methyl tert-Butyl Ether, Monooctanoin and Ursodiol.

84. Choleretics such as Alibendol, Anethole Trithion, Azintamide, Cholic Acid, Cicrotoic Acid, Clanobutin, Cyclobutyrol, Cyclovalone, Cynarin(e), Dehydrocholic Acid, Deoxycholic Acid, Dimecrotic Acid, α-Ethylbenzyl Alcohol, Exiproben, Feguprol, Fencibutirol, Fenipentol, Florantyrone, Hymecromone, Menbutone, 3-(o-Methoxyphenyl)-2-phenylacrylic Acid, Metochalcone, Moquizone, Osalmid, Ox Bile Extract, 4,4'-Oxydi-2-butanol, Piprozolin, Prozapine, 4-Salicyloylmorpholine, Sincalide, Taurocholic Acid, Timonacic, Tocamphyl, Trepibutone and Vanitiolide.

85. Cholinergic agents such as Aceclidine, Acetylcholine Bromide, Acetylcholide Chloride, Aclatonium Napadisilate, Benzpyrinium Bromide, Bethanechol chloride, Carbachol, Carpronium chloride, Demecarium Bromide, Dexpanthenol, Diisopropyl Paraoxon, Echothiophate Iodide, Edrophomium chloride, Eseridine, Furtrethonium, Isoflurophate, Methacholine chloride, Muscarine, Neostigmine, Oxapropanium Iodide, Physostigmine and Pyridostigmine Bromide.

86. Cholinesterase inhibitors such as Ambenonium Chloride, Distigmine Bromide and Galanthamine.

87. Cholinesterase reactivators such as Obidoximine Chloride and Pralidoxime Chloride.

88. Central nervous system stimulants and agents such as Amineptine, Amphetimine, Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate, Diethlpropion, N-Ethylamphetamine, Ethamivan, Etifelmin, Etryptamine, Fencamfamine, Fenethylline, Fenosolone, Flurothyl, Hexacyclonate Sodium, Homocamfin, Mazindol, Megexamide, Methamphetamine, Methylphenidate, Nikethamide, Pemoline, Pentylenetetrazole, Phenidimetrazine, Phenmetrazine, Phentermine, Picrotoxin, Pipradrol, Prolintane and Pyrovalerone.

89. Decongestants such as Amidephrine, Cafaminol, Cyclopentamine, Ephedrine, Epinephrine, Fenoxazoline, Indanazoline, Metizoline, Naphazoline, Nordefrin Hydrochloride, octodrine, Oxymetazoline, Phenylephrine Hydrochloride, Phenylpropanolamine Hydrochloride, Phenylpropylmethylamine, Propylhexedrine, Pseudoephedrine, Tetrahydrozoline, Tymazoline and Xylometazoline.

90. Dental carries prophylactics such as Sodium Fluoride.

91. Depigmentors such as Hydroquinine, Hydroquinone and Monobenzone.

92. Diuretics, including:

organomercurials such as Chlormerodrin, Meralluride, Mercamphamide, Mercaptomerin Sodium, Mercumallylic Acid, Mercumatilin Sodium, Mercurous Chloride and Mersalyl;

Pteridines such as Furterene and Triamterene;

Purines such as Acefylline, 7-Morpholinomethyltheophylline, Pamabrom, Protheobromine and Theobromine;

Steroids such as Canrenone, Oleandrin and Spironolactone;

Sulfonamide derivatives such as Acetazolmide, Ambuside, Azosemide, Bumetanide, Butazolamide, Chloraminophenamide, Clofenamide, Clopamide, Clorexolene, Diphenylmethane-4,4'-disulfonamide, Disulfamide, Ethoxzolamide, Furosemide, Indapamide, Mefruside, Methazolamide, Piretanide, Quinethazone, Torasemide, Tripamide and Xipamide;

Uracils such as Aminometradine and Amisometradine;

others such as Amanozine, Amiloride, Arbutin, Chlorazanil, Ethacrynic Acid, Etozolin, Hydracarbazine, Isosorbide, Mannitol, Metochalcone, Muzolimine, Perhexiline, Ticrynafen and Urea.

93. Dopamine receptor agonists such as Bromocriptine, Dopexamine, Fenoldopam, Ibopamine, Lisuride, Naxagolide and Pergolide.

94. Ectoparasiticides such as Amitraz, Benzyl Benzoate, Carbaryl, Crotamiton, DDT, Dixanthogen, Isobornyl Thiocyanoacetate—Technical, Lime Sulfurated Solution, LIndane, Malathion, Mercuric Oleate, Mesulphen and Sulphur—Pharmaceutical.

95. Enzymes, including:

Digestive enzymes such as α-Amylase (Swine Pancreas), Lipase, Pancrelipase, Pepsin and Rennin;

Mucolytic enzymes such as Lysozyme;

Penicillin inactivating enzymes such as Penicillinase; and

Proteolytic enzymes such as Collagenase, Chymopapain, Chymotrypsins, Papain and Trypsin.

96. Enzyme inducers (hepatic) such as Flumecinol.

97. Estrogens, including:

Nonsteroidal estrogens such as Benzestrol, Broparoestrol, Chlorotrianisene, Dienestrol, Diethylstilbestrol, Diethylstilbestrol Diproprionate, Dimestrol, Fosfestrol, Hexestrol, Methallenestril and Methestrol; and Steroidal estrogens such as Colpormon, Conjugated Estrogenic Hormones, Equilenin, Equilin, Estradiol, Estradiol Benzoate, Estradiol 17β-Cypionate, Estriol, Estrone, Ethinyl Estradiol, Mestranol, Moxestrol, Mytatrienediol, Quinestradiol and Quinestrol.

98. Gastric secretion inhibitors such as Enterogastrone and Octreotide.

99. Glucocorticoids such as 21-Acetoxyprefnenolone, Aalclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, ydrocortisone Phosphate, Hydrocortisone 21-Sodium Succinate, Hydrocortisone Tebutate, Mazipredone, Medrysone, Meprednisone, Methyolprednisolone, Mometasone Furoate, Paramethasone, Prednicarbate, Prednisolone, Prednisolone 21-Diethylaminoacetate, Prednisone Sodium Phosphate, Prednisolone Sodium Succinate, Prednisolone Sodium 21-m-Sulfobenzoate, Prednisolone 21-Stearoylglycolate, Prednisolone Tebutate, Prednisolone 21-Trimethylacetate, Prednisone, Prednival, Prednylidene, Prednylidene 21-Diethylaminoacetate, Tixocortal, Triamcinolone, Triamcinolone Acetonide, Triamcinolone Benetonide and Triamcinolone Hexacetonide.

100. Gonad-Stimulating principles such as Buserelin, Clomiphene, Cyclofenil, Epimestrol, FSH, HCG and LH-RH.

101. Gonadotropic hormones such as LH and PMSG.

102. Growth hormone inhibitors such as Octreotide and Somatostatin.

103. Growth hormone releasing factors such as Semorelin.

104. Growth stimulants such as Somatotropin.

105. Hemolytic agents such as Phenylhydrazine and Phenylhydrazine Hydrochloride.

106. Heparin antagonists such as Hexadimethrine Bromide and Protamines.

107. Hepatoprotectants such as S-Adenosylmethionine, Betaine, Catechin, Citolone, Malotilate, Orazamide, Phosphorylcholine, Protoporphyrin IX, Silymarin-Group, Thiotic Acid and Tiopronin.

108. Immunomodulators such as Amiprilose, Bucillamine, Ditiocarb Sodium, Inosine Pranobex, Interferon-γ, Interleukin-2, Lentinan, Muroctasin, Platonin, Procodazole, Tetramisole, Thymomodulin, Thymopentin and Ubenimex.

109. Immunosuppressants such as Azathioprine, Cyclosporins and Mizoribine.

110. Ion exchange resins such as Carbacrylic Resins, Cholestyramine Resin, Colestipol, Polidexide, Resodec and Sodium Polystyrene Sulfonate.

111. Lactation stimulating hormone such as Prolactin.

112. LH-RH agonists such as Buserelin, Goserelin, Leuprolide, Nafarelin, and Triptorelin.

113. Lipotropic agents such as N-Acetylmethionine, Choline Chloride, Choline Dehydrocholate, Choline Dihydrogen Citrate, Inositol, Lecithin and Methionine.

114. Lupus erythematosus suppressants such as Bismuth Sodium Triglycollamate, Bismuth Subsalicylate, Chloroquine and Hydroxychloroquine.

115. Mineralcorticoids such as Aldosterone, Deoxycorticosterone, Deoxycorticosterone Acetate and Fludrocortisone.

116. Miotic drugs such as Carbachol, Physostigmine, Pilocarpine and Pilocarpus.

117. Monoamine oxidase inhibitors such as Deprenyl, Iproclozide, Iproniazid, Isocarboxazid, Moclobemide, Octomoxin, Pargyline, Phenelzine, Phenoxypropazine, Pivalylbenzhydrazine, Prodipine, Toloxatone and Tranylcypromine.

118. Mucolytic agents such as Acetylcysteine, Bromhexine, Carbocysteine, Domiodol, Letosteine, Lysozyme, Mecysteine Hydrochloride, Mesna, Sobrerol, Stepronin, Tiopronin and Tyloxapol.

119. Muscle relaxants (skeletal) such as Afloqualone, Alcuronium, Atracurium Besylate, Baclofen, Benzoctamine, Benzoquinonium Chloride, C-Calebassine, Carisoprodol, Chlormezanone, Chlorphenesin Carbamate, Chlorproethazine, Chlozoxazone, Curare, Cyclarbamate, Cyclobenzaprine, Dantrolene, Decamethonium Bromide, Diazepam, Eperisone, Fazadinium Bromide, Flumetramide, Gallamine Triethiodide, Hexacarbacholine Bromide, Hexafluorenium Bromide, Idrocilamide, Lauexium Methyl Sulfate, Leptodactyline, Memantine, Mephenesin, Mephenoxalone, Metaxalone, Methocarbamol, Metocurine Iodide, Nimetazepam, Orphenadrine, Pancuronium Bromide, Phenprobamate, Phenyramidol, Pipecurium Bromide, Promoxolane, Quinine Sulfate, Styramate, Succinylcholine Bromide, Succinylcholine Chloride, Succinylcholine Iodine, Suxethonium Bromide, Tetrazepam, Thiocolchicoside, Tizanidine, Tolperisone, Tubocurarine Chloride, Vecuronium Bromide and Zoxolamine.

120. Narcotic antagonists such as Amiphenazole, Cyclazocine, Levallorphan, Nadide, Nalmfene, Nalorphine, Nalorphine Dinicotinate, Naloxone and Naltrexone.

121. Neuroprotective agents such as Dizocilpine.

122. Nootropic agents such as Aceglutamide, Acetylcarnitine, Aniracetam, Bifematlane, Exifone, Fipexide, Idebenone, Indeloxazune Hydrochloride, Nizofenone, Oxiracetam, Piracetam, Propentofylline, Pyritinol and Tacrine.

123. Ophthalmic agents such as 15-ketoprostaglandins.

124. Ovarian hormone such as relaxin.

125. Oxytocic drugs such as Carboprost, Cargutocin, Deaminooxytocin, Ergonovine, Gemeprost, Methylergonovine, Oxytocin, Pituitary (Posterior), Prostaglandin $E_2$, Prostaglandin $F_{2\alpha}$ and Sparteine.

126. Pepsin inhibitors such as Sodium Amylosulfate.

127. Peristaltic stimulants such as Cisapride.

128. Progestogens such as Allylestrenol, Anagestone, Chlormadinone Acetate, Delmadinone Acetate, Demegestone, Desogestrel, Dimethisterone, Dydrogesterone, Ethisterone, Ethynodiol, Flurogestone Acetate, Gestodene, Gestonorone Caproate, Haloprogesterone, 17-Hydroxy-16-methyleneprogesterone, 17α-Hydroxyprogesterone, 17α-Hydroxygesterone Caproate, Lynestrenol, Medrogestone, Medroxyprogesterone, Megestrol Acetate, Melengestrol, Norethindrone, Norethynodrel, Norgesterone, Norgestimate, Norgestrel, Norgestrienone, Norvinisterone, Pentagestrone, Progesterone, Promegestone, Quingestrone and Trengestone.

129. Prolactin inhibitors such as Metergoline.

130. Prostaglandins and prostaglandin analogs such as Arbaprostil, Carboprost, Enprostil, Bemeprost, Limaprost, Misoprostol, Ornoprostil, Prostacyclin, Prostaglandin $E_1$, Prostaglandin $E_2$, Prostagland in $F_{2\alpha}$, Rioprostil, Rosaprostol, Sulprostone and Trimoprostil.

131. Protease inhibitors such as Aprotinin, Camostat, Gabexate and Nafamostat.

132. Respiratory stimulants such as Almitrine, Bemegride, Carbon Dioxide, Cropropamide, Crotethamide, Dimefline, Dimorpholamine, Doxapram, Ethamivan, Fominoben, Lobeline, Mepixanox, Metamivam, Nikethamide, Picrotoxin, Pimeclone, Pyridofylline, Sodium Succinate and Tacrine.

133. Sclerosing agents such as Ethanolamine, Ethylamine, 2-Hexyldecanoic Acid, Polidocanol, Quinine Bisulfate, Quinine Urea Hydrochloride, Sodium Ricinoleate, Sodium Tetradecyl Sulfate and Tribenoside.

134. Sedatives and hypnotics, including:

Acyclic ureides such as Acecarbromal, Apronalide, Bomisovalum, Capuride, Carbromal and Ectylurea;

Alcohols such as Chlorhexadol, Ethchlorvynol, Meparfynol, 4-Methyl-5-thiazoleethanol, tert-Pentyl Alcohol and 2,2,2-Trichloroethanol;

Amides such as Butoctamide, Diethylbromoacetamide, Ibrotamide, Isovaleryl Diethylamide, Niaprazine, Tricetamide, Trimetozine, Zolpidem and Zopiclone;

Barbituric acid derivatives such as Allobarbital, Amobarbital, Aprobarbital, Barbital, Brallabarbital, Butabarbital Sodium, Butalbital, Butallylonal, Butethal, Carbubarb, Cyclobarbital, Cyclopentobarbital, Enallylpropymal, 5-Ethyl-5-(1-piperidyl) barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbital Sodium and Vinylbital;

Benzodiazepine derivatives such as Brotizolam, Doxefazepam, Estazolam, Flunitrazepam, Flurazepam, Haloxazolam, Loprazolam, Lormetazepam, Nitrazepam, Quazepam, Temasepam and Triazolam;

Bromides such as Ammonium Bromide, Calcium Bromide, Calcium Bromolactobionate, Lithium Bromide, Magnesium Bromide, Potassium Bromide and Sodium Bromide;

Carbamates such as Amyl Carbamate—Tertiary, Ethinamate, Hexaprpymate, Meparfynol Carbamate, Novonal and Tricholorourethan;

Chloral derivatives such as Carbocloral, Chloral Betaine, Chloral Formamide, Chloral Hydrate, Chloralantipyrine, Dichloralphenazone, Pentaerythritol Chloral and Triclofos;

Piperidinediones such as Glutehimide, Methyprylon, Piperidione, Pyrithyldione, Taglutimide and Thalidomide;

Quinazolone derivatives such as Etaqualone, Mecloqualone and Methaqualone; and others such as Acetal, Acetophenone, Aldol, Ammonium Valerate, Amphenidone, d-Bornyl α-Bromoisovalerate, d-Bornyl Isovalerate, Bromoform, Calcium 2-Ethylbutanoate, Carfinate, α-Chlorolose, Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane and Sulfonmethane.

135. Thrombolytic agents such as APSAC, Plasmin, Pro-Urokinase, Streptokinase, Tissue Plasminogen Activator and Urokinase;

136. Thyrotropic hormones such as TRH and TSH.

137. Uricosurics such as Benzbromarone, Ethebenecid, Orotic Acid, Oxycinchophen, Probenecid, Sulfinpyrazone, Ticrynafen and Zoxazolamine.

138. Vasodilators (cerebral) such as Bencyclane, Cinnarizine, Citicoline, Cyclandelate, Ciclonicate, Diisopropylamine Dichloractetate, Eburnamonine, Fenoxedil, Flunarizine, Ibudilast, Ifenprodil, Nafronyl, Nicametate, Nicergoline, Nimodipine, Papaverine, Pentifylline, Tinofedrine, Vincamine, Vinpocetine and Viquidil.

139. Vasodilators (coronary) such as Amotriphene, Bendazol, Benfurodil Hemisuccinate, Benziodarone, Chloacizine, Chromonar, Clobenfurol, Clonitrate, Dilazep, Dipyridamole, Droprenilamine, Efloxate, Erythritol, Erythrityl Tetranitrate, Etafenone, Fendiline, Floredil, Ganglefene, Hexestrol Bis(β-diethylaminoethyl ether), Hexobendine, Itramin Tosylate, Khellin, Lidoflazine, Mannitol Hexanitrate, Medibazine, Nicorandil, Nitroglycerin, Pentaerythritol Tetranitrate, Pentrinitrol, Perhexiline, Pimefylline, Prenylamine, Propatyl Nitrate, Pyridofylline, Trapidil, Tricromyl, Trimetazidine, Trolnitrate Phosphate and Visnadine.

140. Vasodilators (peripheral) such as Aluminum Nicotinate, Bamethan, Bencyclane, Betahistine, Bradykinin, Brovincamine, Bufoniode, Buflomedil, Butalamine, Cetiedil, Ciclonicate, Cinepazide, Cinnarizine, Cyclandelate, Diisopropylamine Dichloracetate, Eledoisin, Fenoxidil, Flunarisine, Heronicate, Ifenprodil, Inositol Niacinate, Isoxsuprine, Kallidin, Kallikrein, Moxisylyte, Nafronyl, Nicametate, Nicergoline, Nicofuranose, Nicotinyl Alcohol, Nylidrin, Pentifylline, Pentoxifylline, Piribedil, Protaglandin $E_1$, Suloctidil and Xanthinal Niacinate.

141. Vasoprotectants such as Benzarone, Bioflavonoids, Chromocarb, Clobeoside, Diosmin, Dobesilate Calcium, Escin, Rolescutol, Leucocyanidin, Metescufylline, Quercetin, Rutin and Troxerutin.

142. Vitamins, vitamin sources, and vitamin extracts such as Vitamins A, B, C, D, E, and K and derivatives thereof, Calciferols, Glycyrrhiza and Mecobalamin.

143. Vulnerary agents such as Acetylcysteine, Allantoin, Asiaticoside, Cadexomer Iodine, Chitin, Dextranomer and Oxaceprol.

The drugs can be present in the composition in different forms, depending on which form yields the optimum delivery characteristics. Thus, in the case of drugs, the drug can be in its free base or acid form, or in the form of salts, esters, or any other pharmacologically acceptable derivatives, or as components of molecular complexes.

The amount of drug to be incorporated in the composition varies depending on the particular drug, the desired therapeutic effect, and the time span for which the device is to provide therapy. For most drugs, the passage of the drugs through the skin will be the rate-limiting step in delivery. Thus, the amount of drug and the rate of release is typically adjusted so as to provide transdermal delivery characterized by a zero order time dependency for a prolonged period of time. The minimum amount of drug in the system is selected based on the amount of drug which passes through the skin in the time span for which the device is to provide therapy. Normally, the amount of drug in the system can vary from about 0.1% to about 50% by weight, and preferably, for the lower drug doses permitted by this invention, from about 0.3% to about 30%.

Of course, the composition of the transdermal drug delivery system can also contain agents known to accelerate the delivery of the drug through the skin. These agents have been referred to as skin-penetration enhancers, accelerants, adjuvants, and sorption promoters, and are collectively referred to herein as "enhancers." This class of agents includes those with diverse mechanisms of action including those which have the function of improving the solubility and diffusibility of the drug within the multiple polymer and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the delivery of the drug.

Some examples of enhancers are polyhydric alcohols such as dipropylene glycol, propylene glycol, and polyethylene glycol which enhance drug solubility; oils such as olive oil, squalene, and lanolin; fatty ethers such as cetyl ether and oleyl ether; fatty acid esters such as isopropyl myristate which enhance drug diffusibility; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In certain embodiments of the invention a plasticizer or tackifying agent is incorporated into the formulation to improve the adhesive characteristics of the pressure-sensitive adhesive composition. A tackifying agent is particularly useful in those embodiments in which the drug does not plasticize the polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins. The tackifying agent employed is preferably compatible with the blend of polymers. In preferred embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where a synthetic rubber, for example, is a major component, mineral oil is a preferred tackifying agent.

Some drugs, such as the vasodilator nitroglycerin, function as plasticizers in the composition because they are soluble to a certain degree in the polymers comprising the system. For drug molecules which are not readily soluble in the polymer system, a co-solvent for the drug and polymer can be added. Co-solvents, such as lecithin, retinal derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the drug in the multiple polymer adhesive system.

To summarize, the preferred and optimum compositions for the polyacrylate and polysiloxane embodiments are as follows:

TABLE II

| Component | PERCENT BY WEIGHT Preferred Range | Optimum Range |
|---|---|---|
| First Polymer | 97–9 | 94–14 |
| Second Polymer | 0–95 | 5–85 |
| Polyvinyl-pyrrolidone | 1–20 | 5–15 |
| Co-solvent(s) | 0–30 | 0–20 |
| Enhancer(s) | 0–20 | 0–15 |
| Drug(s) | 0.1–50 | 0.3–30 |

The compositions of this invention may further be provided with various thickeners, fillers and other additives known for use with transdermal drug delivery systems. Where the composition tends to absorb water, for example, when lecithin is used as a co-solvent, hydrophilic substances are especially useful. One type of hydrophilic substance which has been successfully employed is clay. The addition of clay has been found to improve adhesiveness in transdermal formulations without reducing the rate of drug delivery. Suitable clays include aluminum silicate clay, kaolinite, montmorillonite, atapulgite, illite, bentonite, halloysite and the like.

In a device aspect of the invention, the pressure-sensitive adhesive composition can be used as an adhesive portion of any transdermal drug delivery system (e.g., a reservoir device) or it can comprise an adhesive monolithic device. Of course, the principles of the invention would still apply to embodiments where the dermal composition is not a pressure-sensitive adhesive and comprises the drug reservoir.

Figure 1:
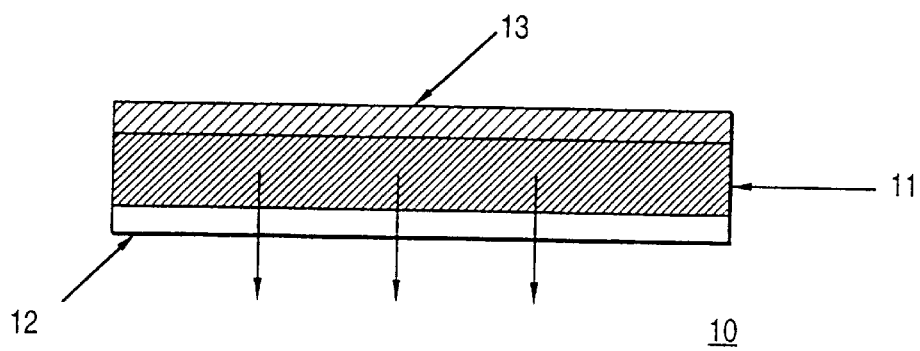
FIG. 1 is a schematic illustration of a monolithic transdermal drug delivery device of the present invention.

Reference to FIG. 1 shows a schematic illustration of an adhesive monolithic device embodiment of the invention 10. The transdermal drug delivery system comprises a monolithic body 11 of a defined geometric shape with a protective release liner 12 on one side of monolithic body 11 and a backing layer 13 on the other side. Removal of the release liner 12 exposes the pressure-sensitive multiple polymer adhesive composition which functions both as the drug carrier matrix and as the means of applying the system to the patient.

A device, or individual dosage unit, of the present invention can be produced in any manner known to those of skill in the art. After the dermal composition is formed, it may be brought into contact with the backing layer in any manner known to those of skill in the art. Such techniques include calender coating, hot melt coating, solution coating, etc. Of course, backing materials are well known in the art and can comprise plastic films of polyethylene, vinyl acetate resins, ethylene/vinyl acetate copolymers, polyvinyl chloride, polyurethane, and the like, metal foils, non-woven fabric, cloth and commercially available laminates. The backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Dow Corning Corporation designated Bio-Release® liner and Syl-off® 7610 liner. For preferred embodiments in which a polysiloxane is part of the multiple polymeric adhesive system, the release liner must be compatible with the silicone adhesive. An example of a suitable commercially available liner is 3M's 1022 Scotch Pak.

The configuration of the transdermal delivery system of the present invention can be in any shape or size as is necessary or desirable. Illustratively, a single dosage unit may have a surface area in the range of 1 to 200 cm². Preferred sizes are from 5 to 60 cm².

In a method aspect of the invention, a plurality of polymers having differing solubility parameters are blended (but not chemically reacted or cross-linked) with soluble PVP to result in a pressure-sensitive adhesive composition, or transdermal drug delivery system adhesive system (with incorporated drug), which controls delivery of an incorporated drug into and through the epidermis. The blending of polymers results in an adjustment of the saturation concentration of the drug in the polymeric system and therefore permits selective modulation of the transdermal drug delivery rate. The term "blending," of course, incorporates choosing the appropriate polymeric components, and the proportions thereof, to achieve the desired effect.

In a preferred embodiment of the invention, a transdermal drug delivery system is prepared by mixing a soluble PVP, polyacrylate, polysiloxane, drug, co-solvent(s), and tackifying agent, if needed, in an appropriate volatile solvent(s), then casting the mixture and removing the solvent(s) by evaporation to form a film.

Suitable volatile solvents include, but are not limited to, alcohols such as isopropanol and ethanol; aromatics such as xylenes and toluene; aliphatics such as hexane, cyclohexane, and heptane; and alkanoic acid esters such as ethyl acetate and butyl acetate.

An exemplary general method for the preparation of an embodiment that contains a soluble PVP is as follows:

1. Appropriate amounts of soluble PVP, solvent(s), enhancer(s), and organic solvent(s) (for example toluene) are combined and thoroughly mixed together in a vessel.
2. The drug is then added to the mixture and agitation is carried out until the drug is uniformly mixed in.
3. Appropriate amounts of polysiloxane with or without polyacrylate are then added to the drug mixture, and thoroughly mixed.
4. The formulation is then transferred to a coating operation where it is coated onto a protective release liner at a controlled specified thickness. The coated product is then passed through an oven in order to drive off all volatile processing solvents.
5. The dried product on the release liner is then joined to the backing material and wound into rolls for storage.
6. Appropriate size and shape "systems" are die-cut from the roll material and then pouched.

An exemplary general method for the preparation of an embodiment that does not contain a soluble PVP is as follows:

1. Appropriate amounts of polysiloxane and polyacrylate, dissolved in a solvent(s), are combined and thoroughly mixed together in a vessel.
2. The drug is then added to the polymer mixture and agitation is carried out until the drug is uniformly mixed in.
3. Co-solvents and enhancers, if necessary, can then be added to the drug-polymer mixture, and thoroughly mixed.
4. The formulation is then transferred to a coating operation where it is coated onto a protective release liner at a controlled specified thickness. The coated product is then passed through an oven in order to drive off all volatile processing solvents.
5. The dried product on the release liner is then joined to the backing material and wound into rolls for storage.
6. Appropriate size and shape "systems" are die-cut from the roll material and then pouched.

The order of steps, the amount of the ingredients, and the amount and time of agitation or mixing may be importance process variables which will depend on the specific polymers, drug, cosolvents, and enhancers used in the formulation. These factors can be adjusted by those skilled in the art, while keeping in mind the object of providing a uniform product. It is believed that a number of other methods, including changing some of the order of steps, can be carried out and will give desirable results. In addition to having various shapes, the dosage units produces may come in various sizes. A surface area in the range of 1 to 200 square centimeters is contemplated, and the presently preferred sizes are: 5, 10, 15, 20, 30, 30 and 60 are centimeters.

Said PVP preferably has a molecular weight of about 2,000 to 1,100,000, more preferably 5,000 to 100,000, and most preferably 7,000 to 54,000.

Preferred embodiments comprise a soluble PVP with a rubber-based pressure-sensitive adhesive and a polyacrylate polymer. Particularly preferred blends include blends of a polyacrylate, a polysiloxane and a soluble PVP.

Soluble PVP has been found to be highly effective in preventing crystallization of drugs, in adhesive-type transdermal drug delivery systems according to the invention. In particular, soluble PVP has proved useful in maintaining a norethindrone acetate (NETA) system and an NETA/estradiol system substantially crystal-free. Other specific drugs for which soluble PVP is particularly usefully employed according to the invention include albuterol, estradiol, haloperidol and alprazolam.

The amount and type of soluble PVP required in the foregoing preferred embodiment will depend on the quantity and type of drug present in the adhesive, as well as the type of adhesive, but can be readily determined through routine experimentation. Typically, the PVP is present in an amount from about 1% to about 20% by weight, preferably from about 5% to about 15% by weight. However, the amount of PVP can be higher than 20% for example, up to 40%, depending on the particular drug used and on the desired properties of the blend.

For example, when the drug is norethindrone acetate (NETA), an optimum concentration of about 10% by weight PVP has been found to inhibit NETA crystal formation without adversely affecting NETA flux from a multiple polymer adhesive system (polyacrylate/polysiloxane). When the drug is estradiol, the inclusion of 5–10% of soluble PVP in the formulation not only increases the estradiol flux, but increases the total amount of estradiol through the skin. When the drug is albuterol, an optimum concentration has been found to be about 5% by weight.

Large amounts of soluble PVP can cause a decrease in the flux of drug. For example, when the PVP is present in amounts exceeding about 20% by weight, NETA flux begins to decrease.

The PVP employed according to the invention is dissolved together with one or more of the additional polymeric materials of the inventive blend.

The type and quantity of soluble PVP also can have significant effects on the adhesive properties of the finished product. In adhesives with higher shear properties, it is advantageous to include a lower molecular weight soluble PVP, whereas in low shear adhesives, the higher molecular weight soluble PVP's are preferred.

EXAMPLES

The following specific examples are included as illustrative of pressure-sensitive adhesive compositions and transdermal drug delivery systems, and methods of making same, within the contemplation of the invention. These examples are in no way intended to be limiting of the scope of the invention.

The following commercially available adhesives were used in the blends comprising the multiple polymer adhesive system of the examples:

"Duro-Tak 80-1194, 80-1196, 80-1054, 80-1074, 80-1058, 80-2434, 80-1070, 80-6172, and 80-1197" are trademarks of National Starch and Chemical Corporation, Bridgewater, N.J. for acrylic adhesives (polyacrylates) in organic solutions. "BIO-PSA X7-3027, X7-4919, X7-2685, X7-3122, X7-4603, X7-4301, X7-4301, X7-4303 and X7-4503" are trademarks of Dow Corning Corporation, Medical Products, Midland, Mich. for silicone adhesives (polysiloxanes) in organic solutions. BIO-PSA-3027 is particularly suitable for use in formulations containing amine-functional drugs, such as albuterol and pilocarpine, in the following examples.

"Gelva-Multipolymer Solution (GMS) 737, 788, and 2480" are trademarks of Monsanto Company, St. Louis, Mo., for an acrylic adhesive in organic solution. "Vistanex LM-LS-LC" is a trademark of Exxon Chemical Company, Houston, Tex., for a polyisobutylene polymer with a Flory molecular weight of 42,600 to 46,100.

"Elvax 40-W" is a trademark of Du Pont Company, Wilmington, Del., for a polyethylene/vinyl acetate copolymer (40% vinyl acetate content).

Kraton D 1101, Kraton D 1107 and Kraton G 1657 are trademarks of the Shell Chemical Company, Houston, Tex., for styrene-butadiene-styrene (S-B-S), styrene-isoprene-styrene (S-I-S) and styrene-ethylene/butylene-styrene (S-EB-S), respectively, block copolymer rubbers Nitroglycerin is available as a solution in a solvent such as ethanol, toluene, and propylene glycol from ICI Americas, Inc., Willmington, Del.

The aforementioned polymeric adhesives are supplied, or prepared, as solutions wherein the percent solids by weight are as follows:

| Ingredient | Percent Solids |
|---|---|
| BIO-PSA X7-3027 | 50 |
| BIO-PSA X7-3122 | 65 |
| BIO-PSA X7 4301 | 60 |
| BIO-PSA X7-4303 | 60 |
| BIO-PSA X7-4503 | 60 |
| BIO-PSA X7-4603 | 60 |
| BIO-PSA X7-4919 | 50 |
| BIO-PSA X7-2685 | 50 |
| Duro-Tak 80-1194 | 45 |
| Duro-Tak 80-1196 | 45 |
| Duro-Tak 80-1197 | 45 |
| Elvax 40-W | 30 |
| GMS 737 | 32 |
| Kraton D 1101 | 30 |
| Kraton D 1107 | 30 |
| Kraton G 1657 | |
| Vistanex LM-MS-LC | 30 |

"360 Medical Fluid" is a trademark of Dow Corning Corporation for a polydimethylsiloxane fluid. In certain embodiments of the invention, 360 Medical Fluid is added as a tackifier to improve the adhesive characteristics of the end product.

"Kollidon" is a trademark of BASF AG, Ludwigshafen, Germany, for a polyvinylpyrrolidone (PVP) polymer.

Preferred are "Kollidon 17PF," "Kollidon 25," and "Kollidon 30."

Example 1

A nitroglycerin-polymer mixture was prepared by combining 22.0 parts of nitroglycerin, 1.0 part of dipropylene glycol, 1.3 parts of lecithin, 0.8 parts of propylene glycol, 2.5 parts of 360 Medial Fluid (1000 cs), 1.0 part of bentonite, 63.6 parts of polyacrylate (Duro-Tak 80-1194), and 85.6 parts of polysiloxane (BIO-PSA X7-4919), and mixed well in an appropriate container. Nitroglycerin is available as a solution in solvents such as ethanol, toluene, and propylene glycol from ICI Americas Inc., Wilmington, Del. In this instance, the nitroglycerin was added as a solution in toluene mixed together with the polyacrylate. The resulting composition had the ingredient concentrations on a "dry" basis, that is, after removal of volatile process solvents, shown below.

| COMPONENT | PERCENT BY WEIGHT |
|---|---|
| Polysiloxane (Dow Corning Silicone Adhesive BIO-PSA X7-4919) | 42.8 |
| Polyacrylate (National Starch Acrylic Adhesive, Duro-Tak 80-1194) | 28.6 |
| Polydimethylsiloxane fluid (Dow Corning 360 Medical Fluid) | 2.5 |
| Lecithin | 1.3 |
| Propylene glycol | 0.8 |
| Dipropylene glycol | 1.0 |
| Bentonite | 1.0 |
| Nitroglycerin | 22.0 |
| | 100.0 |

Figure 2:
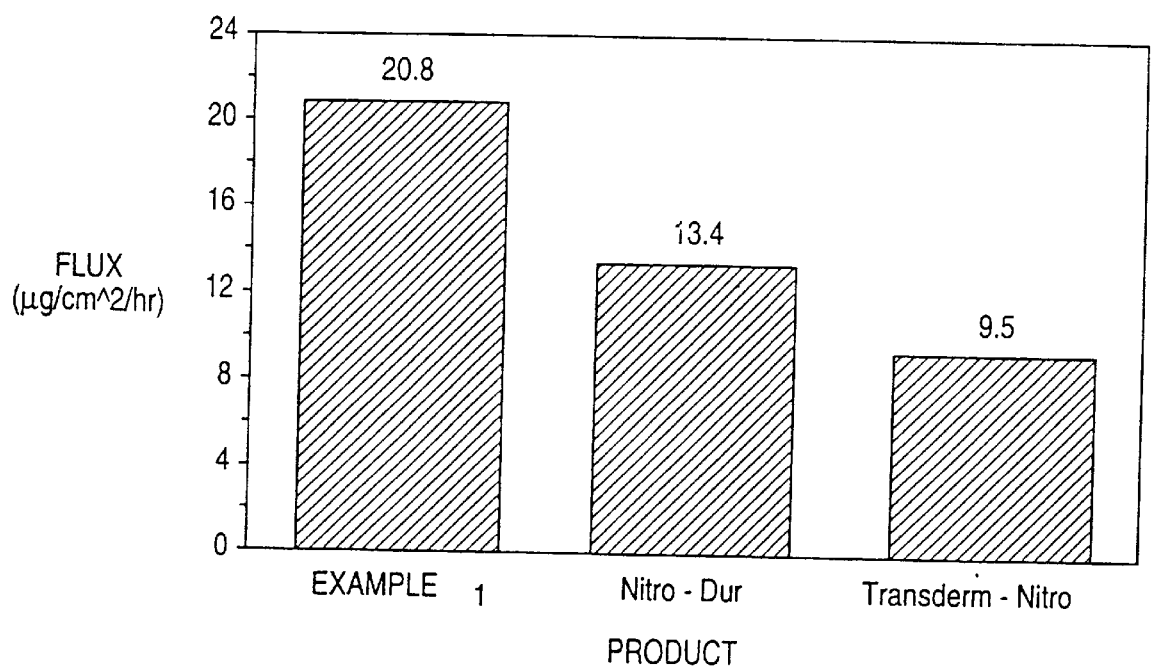
FIG. 2 is a graphic representation of the steady-state nitroglycerin flux rates through cadaver skin in vitro from a transdermal drug delivery composition of the present invention (formulation of Example 1) and two commercially-available nitroglycerin-containing transdermal delivery devices: Transderm-Nitro® (a trademark of Ciba-Geigy Corporation, Summit, N.J.), and Nitro-Dur® (a trademark of Key Pharmaceuticals, Inc., Kenilworth, N.J.)

Nitroglycerin flux results through cadaver skin in vitro from the formulation of Example 1, Transderm-Nitro® (a trademark of Ciba-Geigy Corporation, Summit, N.J.), and Nitro-Dur® (a trademark of Key Pharmaceuticals, Inc., Kenilworth, N.J.) are summarized in FIG. 2. As shown in FIG. 2, nitroglycerin flux from the dermal composition of Example 1 (20.8 $\mu g/cm^2 hr$) was approximately twice that from Transderm-Nitros (9.5 $\mu g/cm^2 hr$) and about 1.5 times that from Nitro-Dur® (13.4 $\mu g/cm^2 hr$).

Examples 2–5

In the following examples (2–5), the method of Example 1 was used with the appropriate amounts of starting materials to yield compositions having the following ingredient concentrations set forth in tabular form in TABLE III. Example 2 is presented for comparative purposes and its formulation is not within the scope of the present invention. Example 3 and 5 are adhesive compositions comprising blends of polyacrylate and a second polymer selected to illustrate the principles of the invention. All other components, such as excipients or fillers, remain constant in composition and amount from Examples 2 to 5.

TABLE III

| Ingredient (sp, $[J/CM^3]^{1/2}$) | Ex.2 | Ex.3 | Ex.4 | Ex.5 |
|---|---|---|---|---|
| Polyacrylate (21) | 73.2 | 33.1 | 33.1 | 33.1 |
| Ethylene/vinyl acetate | — | 40.1 | — | — |

TABLE III-continued

| Ingredient (sp, [J/CM³]½) | Ex.2 | Ex.3 | Ex.4 | Ex.5 |
|---|---|---|---|---|
| (21) | | | | |
| Polyisobutylene (17) | — | — | 40.1 | — |
| Polysiloxane (15) | — | — | — | 40.1 |
| Nitroglycerine (27) | 20.8 | 20.8 | 20.8 | 20.8 |
| Oleic acid | 2.0 | 2.0 | 2.0 | 2.0 |
| Propylene glycol | 0.8 | 0.8 | 0.8 | 0.8 |
| Lecithin | 1.2 | 1.2 | 1.2 | 1.2 |
| Dipropylene glycol | 1.0 | 1.0 | 1.0 | 1.0 |
| Bentonite | 1.0 | 1.0 | 1.0 | 1.0 |

Figure 3:
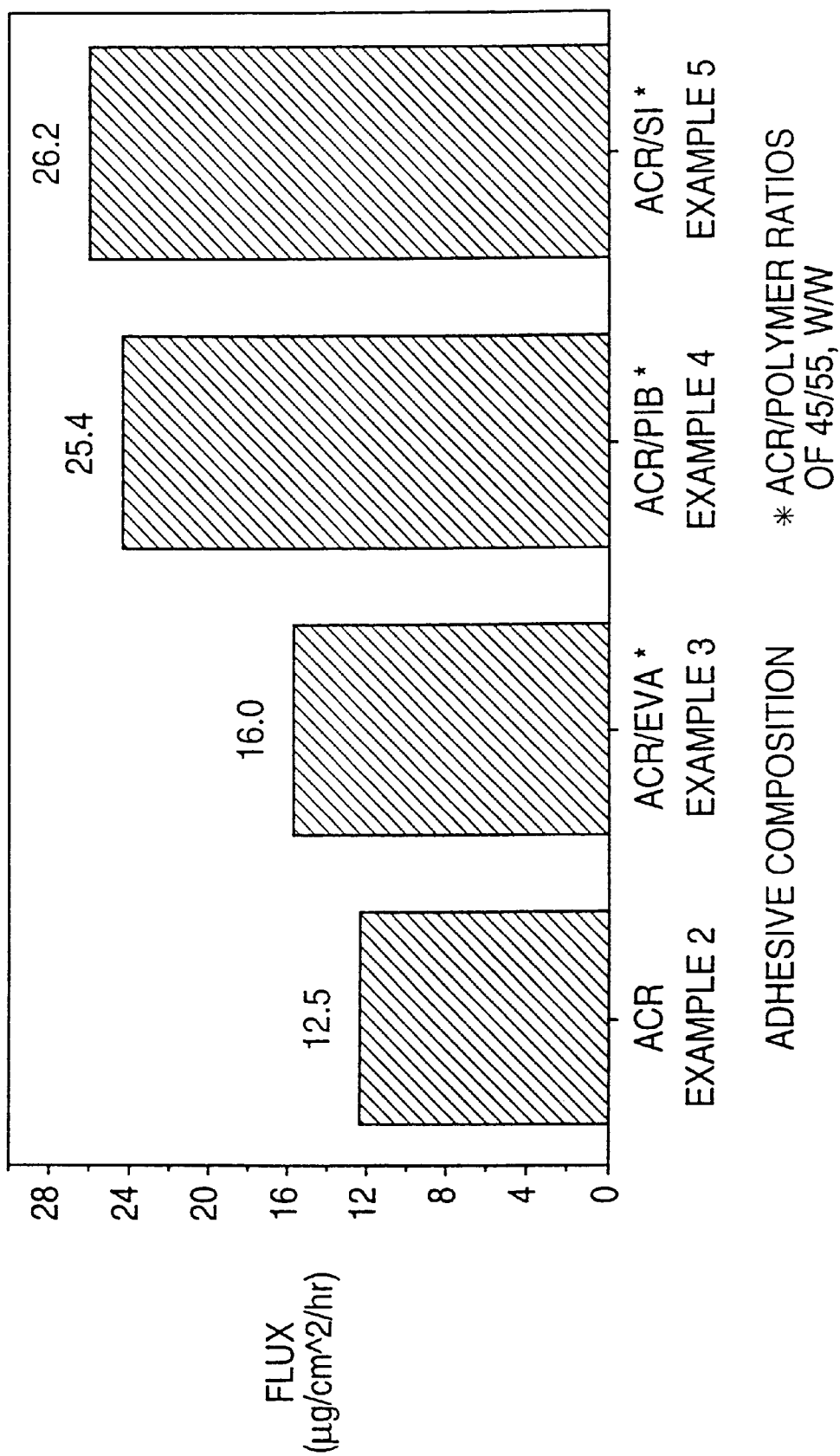
FIG. 3 is a graphical representation which summarizes in vitro nitroglycerin flux results through cadaver skin for the polymeric systems of Examples 2–5. The composition of Example 2 (polyacrylate-only adhesive) is compared to the multiple polymer compositions of Examples 3, 4, and 5, in which the polyacrylate is blended with an ethylene vinyl acetate, a polyisobutylene, and a polysiloxane, respectively.

FIG. 3 graphically summarizes the in vitro nitroglycerin flux results through cadaver epidermis from the dermal compositions of Examples 2 to 5. As seen in FIG. 3, addition of either polyisobutylene (Example 4) or polysiloxane (Example 5)—both with SPs lower than polyacrylate—resulted in doubling of the nitroglycerin flux as compared to an all polyacrylate system (Example 2). However, addition of ethylene/vinyl acetate (Example 3)—with an SP value similar to the polyacrylate—resulted in little effect on nitroglycerin flux as compared to the system of Example 2. Thus, the formulation of Example 3 is not within the scope of the present invention.

Example 6

A series of nitroglycerin-containing compositions (I–VI) were prepared in which the polyacrylate (Duro-Tak 80-1194) to polysiloxane (X7-3122) ratio was varied from 100.0:0.0 (all polyacrylate) to 0.0:100.0 (all siloxane) by weight. Nitroglycerin concentration was held at 20% for all compositions. The ingredient concentrations of these compositions are shown below in TABLE IV.

TABLE IV

| Ingredient | I | II | III | IV | V | VI |
|---|---|---|---|---|---|---|
| Polysiloxane | — | 14.4 | 28.8 | 43.2 | 57.6 | 72.6 |
| Silicone Fluid | — | 1.6 | 3.2 | 4.8 | 6.4 | 8.0 |
| Polyacrylate | 80.0 | 64.0 | 48.0 | 32.8 | 16.0 | — |
| Nitroglycerin | 20.0 | 20.0 | 20.0 | 20.0 | 20.0 | 20.0 |

Figure 4:
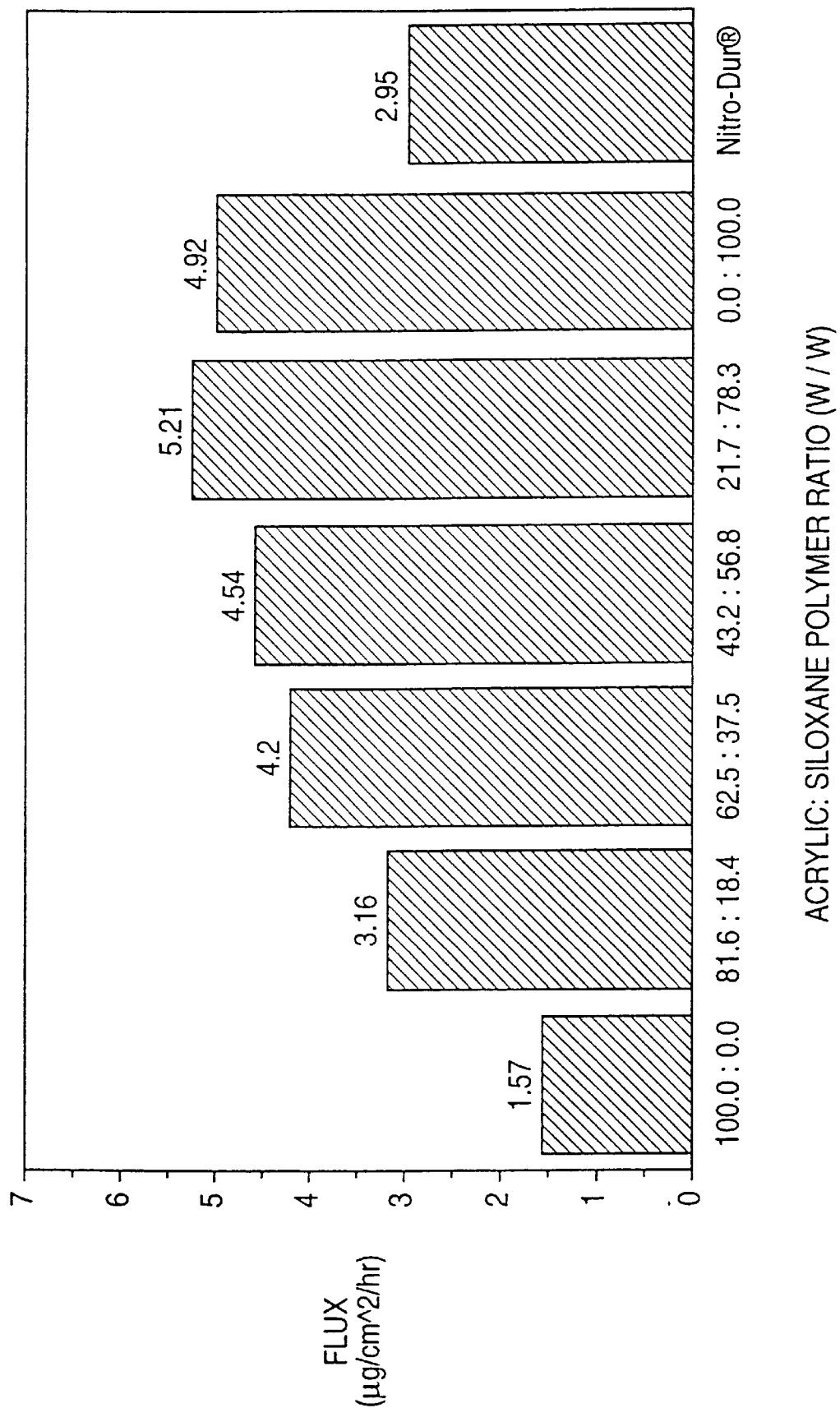
FIG. 4 is a graphical representation of the steady-state nitroglycerin flux through cadaver skin in vitro from a multiple polymer transdermal adhesive system of Example 6 comprising various weight ratios of polyacrylate and polysiloxane.

In vitro skin flux was determined for these compositions and the results are summarized in Table V and graphically depicted in FIG. 4.

TABLE V

| | Polyacrylate % | Polysiloxane % | GTN Flux (μg/cm²/hr) | Tlag (hr) |
|---|---|---|---|---|
| I | 100.0 | 0 | 1.6 | 0.0 |
| II | 81.6 | 18.4 | 3.2 | 1.5 |
| III | 62.5 | 37.5 | 4.2 | 2.0 |
| IV | 43.2 | 56.8 | 4.5 | 2.3 |
| V | 21.7 | 78.3 | 5.2 | 2.3 |
| VI | 0 | 100 | 4.9 | 2.4 |
| Nitro-Dur ® | — | — | 3.0 | 2.5 |

As shown, nitroglycerin (GTN) flux increased as the concentration of polysiloxane in the multiple polymer adhesive matrix increased up to a maximum, at around 80% polysiloxane, after which no more increase in flux was seen. It appears that beyond a certain concentration of siloxane polymer, the nitroglycerin activity ceases to increase (unit activity is reached), and the flux no longer increases. The attainment of saturation concentration (unit activity) is further verified by the fact that Composition VI had nitroglycerin exudate; that is, the surface of the adhesive was "wet" with excess nitroglycerin. Of course, Composition VI, which is all polysiloxane, is not within the contemplation of the invention.

The composition of the blend of polymers is preferably chosen so that the flux rate of drug from the blend is at a maximum. Studies similar to those reported herein may be employed to assist in selecting the appropriate components of the blend and the weight ratios thereof. In alternative embodiments, it may be desirable to select a composition in which the flux rate will be retarded.

Examples 7–9

An estradiol-polymer mixture (Example 7) was prepared by combining 2.0 parts of 17β-estradiol, 2.0 parts of propylene glycol, 3.0 parts of lecithin, 5.0 parts of oleic acid, 5.0 parts of dipropylene glycol, 93.3 parts of polyacrylate (Duro-Tak 80-1196), and 63.1 parts of polysiloxane (BIO-PSA X7-3122), and mixing well in an appropriate container. The resulting composition had the ingredient concentrations on a "dry" basis, that is, after removal of volatile process solvents, given below in TABLE VI.

Examples 8 and 9 were made in accordance with the method of Example 7. The compositions of Examples 8 and 9 have the same drug and additional components, such as the co-solvents, as Example 7, but are not within the scope of this invention inasmuch as the resulting adhesive matrices are single polymer systems. Examples 8 and 9 are given for comparative purposes only.

TABLE VI

| Ingredient | 7 | 8 | 9 |
|---|---|---|---|
| Polyacrylate | 42.0 | 83.0 | — |
| Polysiloxane | 41.0 | — | 83.0 |
| Estradiol | 2.0 | 2.0 | 2.0 |
| Oleic acid | 5.0 | 5.0 | 5.0 |
| Propylene glycol | 2.0 | 2.0 | 2.0 |
| Lecithin | 3.0 | 3.0 | 3.0 |
| Dipropylene glycol | 5.0 | 5.0 | 5.0 |

Figure 5:
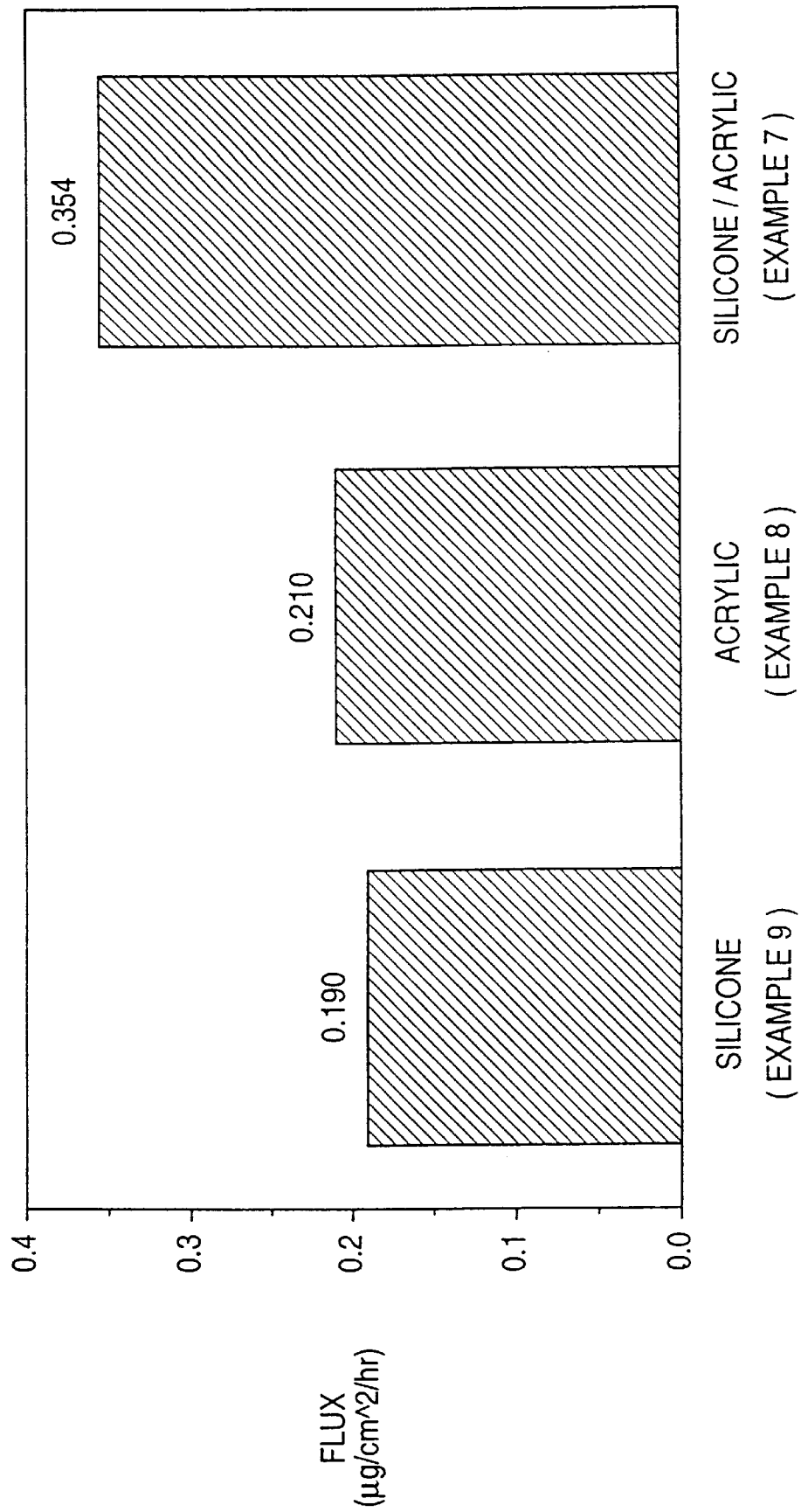
FIG. 5 is a graphical representation of steady-state estradiol flux through cadaver skin in vitro from the drug delivery systems of the prior art, specifically single polymeric adhesives of silicone and acrylic, as compared to a multiple polymer transdermal adhesive system (polyacrylate/polysiloxane) of the present invention.

Estradiol flux in vitro from the systems of Examples 7, 8, and 9 is shown in FIG. 5. As seen in FIG. 5, delivery from the system of this invention utilizing the multiple polymer adhesive (polyacrylate/polysiloxane) of Example 7 was substantially greater than delivery from the prior art systems comprising single polymer adhesives (Examples 8 and 9).

Examples 10–13

In the following examples (10–13), the method of Example 7 was used with the appropriate amounts of starting materials to yield compositions having the ingredient concentrations set forth in TABLE VII.

TABLE VII

| Ingredient | 10 | 11 | 12 | 13 |
|---|---|---|---|---|
| Polysiloxane | 18.0 | 33.5 | 39.5 | 58.0 |
| Polyacrylate | 65.0 | 39.5 | 33.5 | 15.0 |
| Estradiol | 2.0 | 2.0 | 2.0 | 2.0 |
| Oleic acid | 5.0 | 5.0 | 5.0 | 5.0 |
| Propylene glycol | 2.0 | 2.0 | 2.0 | 2.0 |
| Lecithin | 3.0 | 3.0 | 3.0 | 3.0 |

TABLE VII-continued

| Inqredient | 10 | 11 | 12 | 13 |
|---|---|---|---|---|
| Silicone fluid | 5.0 | 15.0 | 15.0 | 15.0 |

Figure 6:
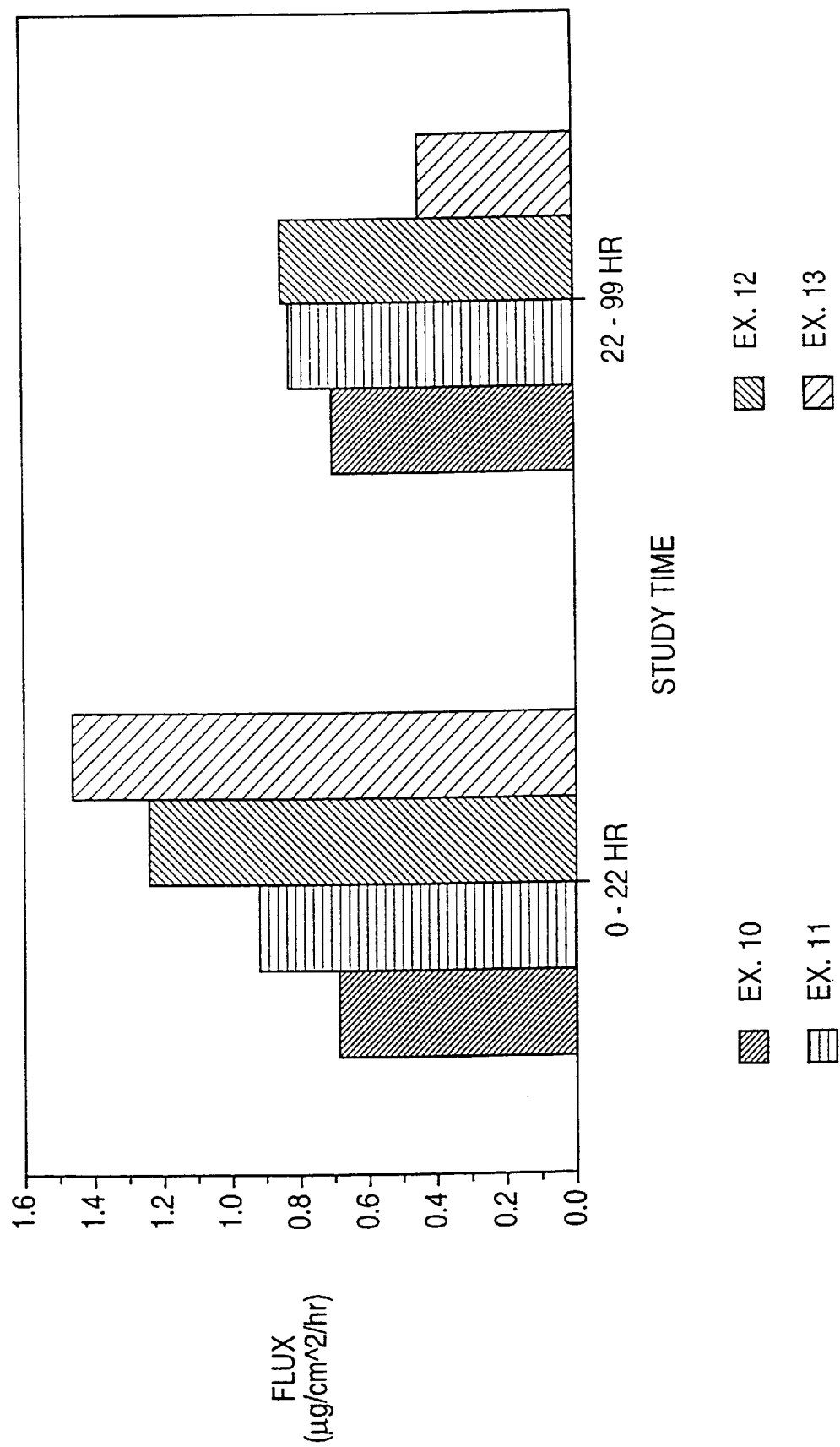
FIG. 6 is a graphical representation of average estradiol flux through cadaver skin in vitro from 0 to 22 hours and from 22 to 99 hours for a multiple polymer transdermal adhesive system comprising various weight ratios of polyacrylate and polysiloxane.

FIG. 6 shows estradiol flux results for the compositions of Examples 10–13; average flux was calculated for each composition from 0 to 22 hours and from 22 to 99 hours from the start of the study. As seen in FIG. 6, estradiol flux progressively increased with increased silicone polymer content during the first 22 hours of delivery, but was affected to a much lesser degree during the remainder of the study (22 to 99 hours). Thus, significant adjustment of the estradiol delivery rate during the initial phase of delivery was accomplished, with minor effects on the later delivery phase, by modulating the polysiloxane to polyacrylate polymer ratio. FIG. 6 also illustrates that the delivery characteristics over time can be adjusted by the appropriate choice of polymers and respective weight ratios. For example, the formulation of Example 10 delivers drug at approximately the same rate over time whereas the formulation of Example 13 delivers more quickly in the early phase than the latter.

Examples 14–16

A norethindrone acetate-polymer mixture was prepared by combining 0.6 parts of norethindrone acetate, 1.0 parts of butylene glycol, and 40.9 parts of polyacrylate (Duro-Tak 80-1194), and mixing well in an appropriate container. The resulting composition had the ingredient concentrations on a "dry" basis, that is, after removal of volatile process solvents, given below in TABLE VIII. The same method was employed to make Examples 15 and 16.

TABLE VIII

| Ingredient | 14 | 15 | 16 |
|---|---|---|---|
| Polyacrylate | 92.0 | — | 46.0 |
| Polysiloxane | — | 92.0 | 46.0 |
| Norethindrone acetate | 3.0 | 3.0 | 3.0 |
| Butylene glycol | 5.0 | 5.0 | 5.0 |

Figure 7:
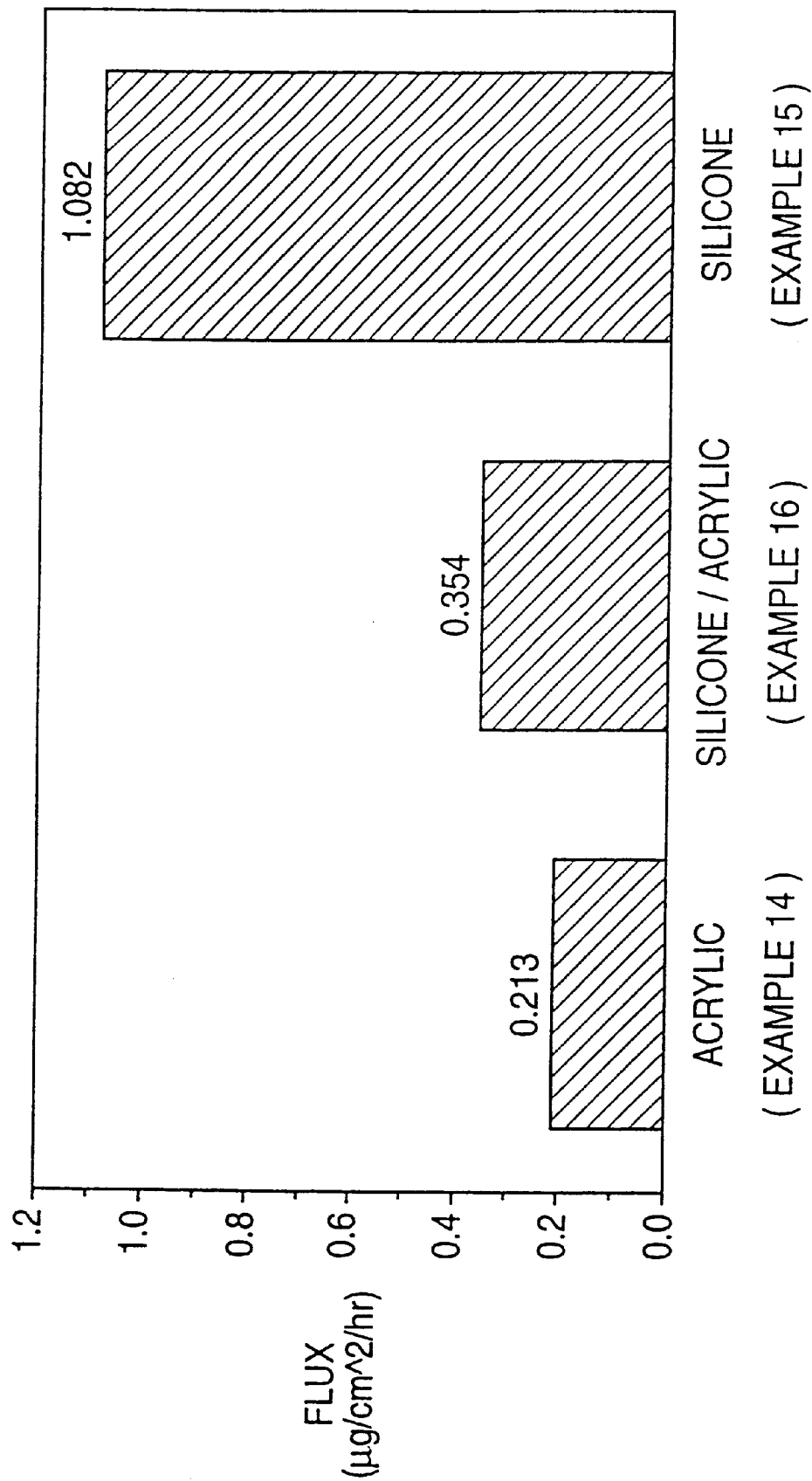
FIG. 7 is a graphical representation of steady-state norethindrone acetate flux through cadaver skin in vitro from the drug delivery systems of the prior art, specifically single polymeric adhesives of silicone and acrylic, as compared to a multiple polymer transdermal adhesive system (polyacrylate/polysiloxane) of the present invention.

Norethindrone acetate flux in vitro from the systems of Examples 14, 15, and 16 is shown in FIG. 7. As seen in FIG. 7, norethindrone acetate delivery from the polyacrylate/polysiloxane systems of this invention (Example 16) was intermediate to delivery from the single polymer systems not of this invention (Example 14 and 15). Thus, blending the polyacrylate and polysiloxane results in modulation of the norethindrone acetate flux.

Examples 17–20

As estradiol/norethindrone acetate combination-polymer mixture was prepared by combining 0.6 parts of 17β-estradiol, 0.6 parts of norethindrone acetate, 0.6 parts of butylene glycol, 0.6 parts of oleic acid, 1.5 parts of lecithin, 4.5 parts of silicone fluid (polydimethylsiloxane fluid, Dow Corning 360 Medical Fluid, 100 cs), and 43.2 parts of polysiloxane (BIO-PSA X7-4919), and mixing well in an appropriate container. The method of Example 7 was used with the appropriate amounts of starting materials to yield the compositions of Example 18, 19 and 20. The polyacrylate used in Examples 18–20 was National Starch Acrylic Adhesive, Duro-Tak 80-1197. The resulting compositions had the ingredient concentrations on a "dry" basis, that is, after removal of volatile process solvents, given below in TABLE IX.

TABLE IX

| Ingredient | 17 | 18 | 19 | 20 |
|---|---|---|---|---|
| Polysiloxane | 72.0 | 8.0 | 60.0 | 47.0 |
| Polyacrylate | — | 5.0 | 15.0 | 30.0 |
| Estradiol | 2.0 | 2.0 | 2.0 | 2.0 |
| Norethindrone acetate | 2.0 | 2.0 | 2.0 | 2.0 |
| Oleic Acid | 2.0 | 2.0 | 2.0 | 2.0 |
| Butylene glycol | 2.0 | 2.0 | 2.0 | 2.0 |
| Lecithin | 5.0 | 5.0 | 5.0 | 5.0 |
| Silicone fluid | 15.0 | 14.0 | 12.0 | 10.0 |

Figure 8:
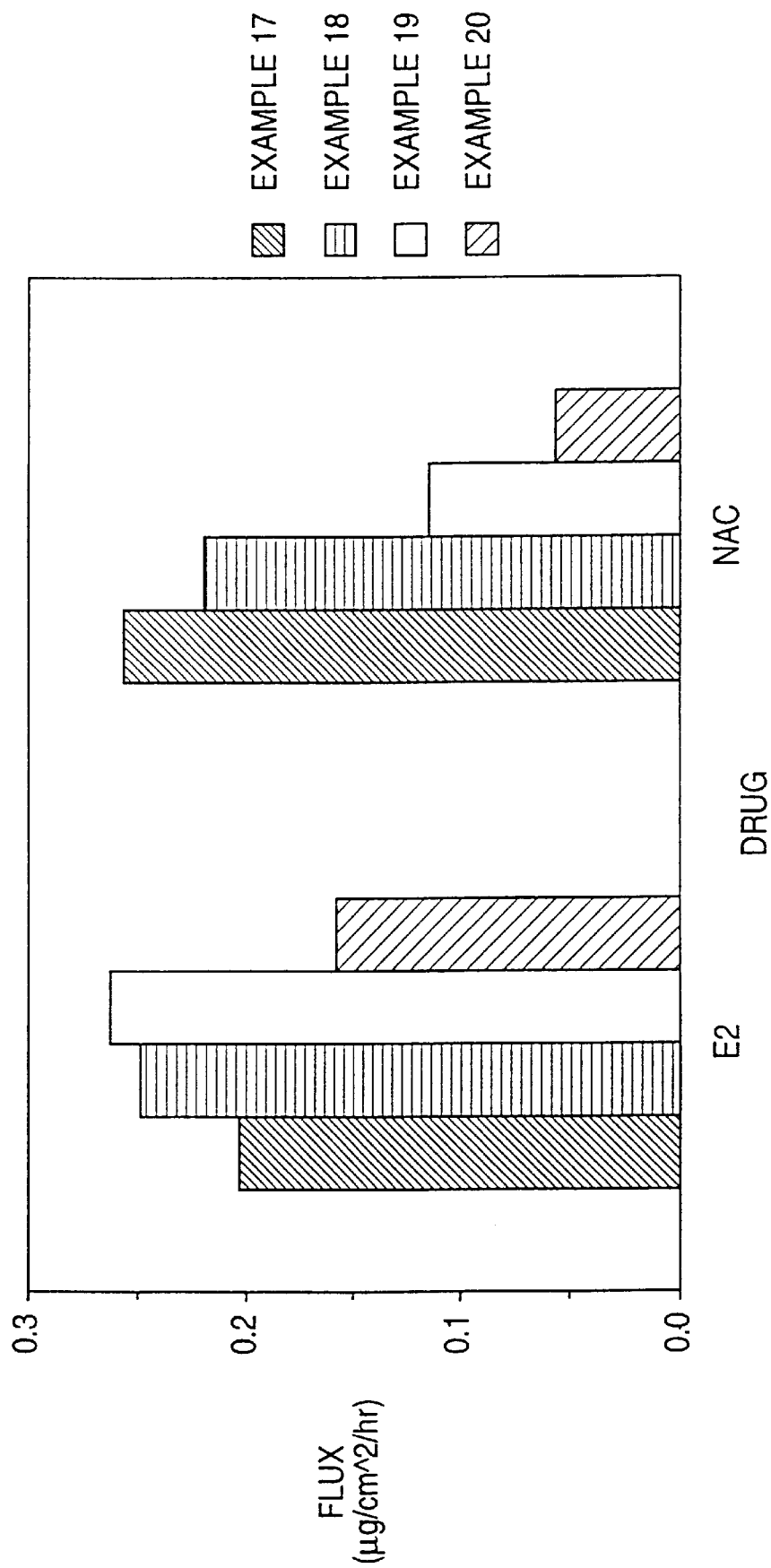
FIG. 8 is a graphical representation of average estradiol and norethindrone acetate flux through cadaver skin in vitro for a multiple polymer transdermal adhesive system comprising both drugs and various weight ratios of polyacrylate and polysiloxane.
Figure 9:
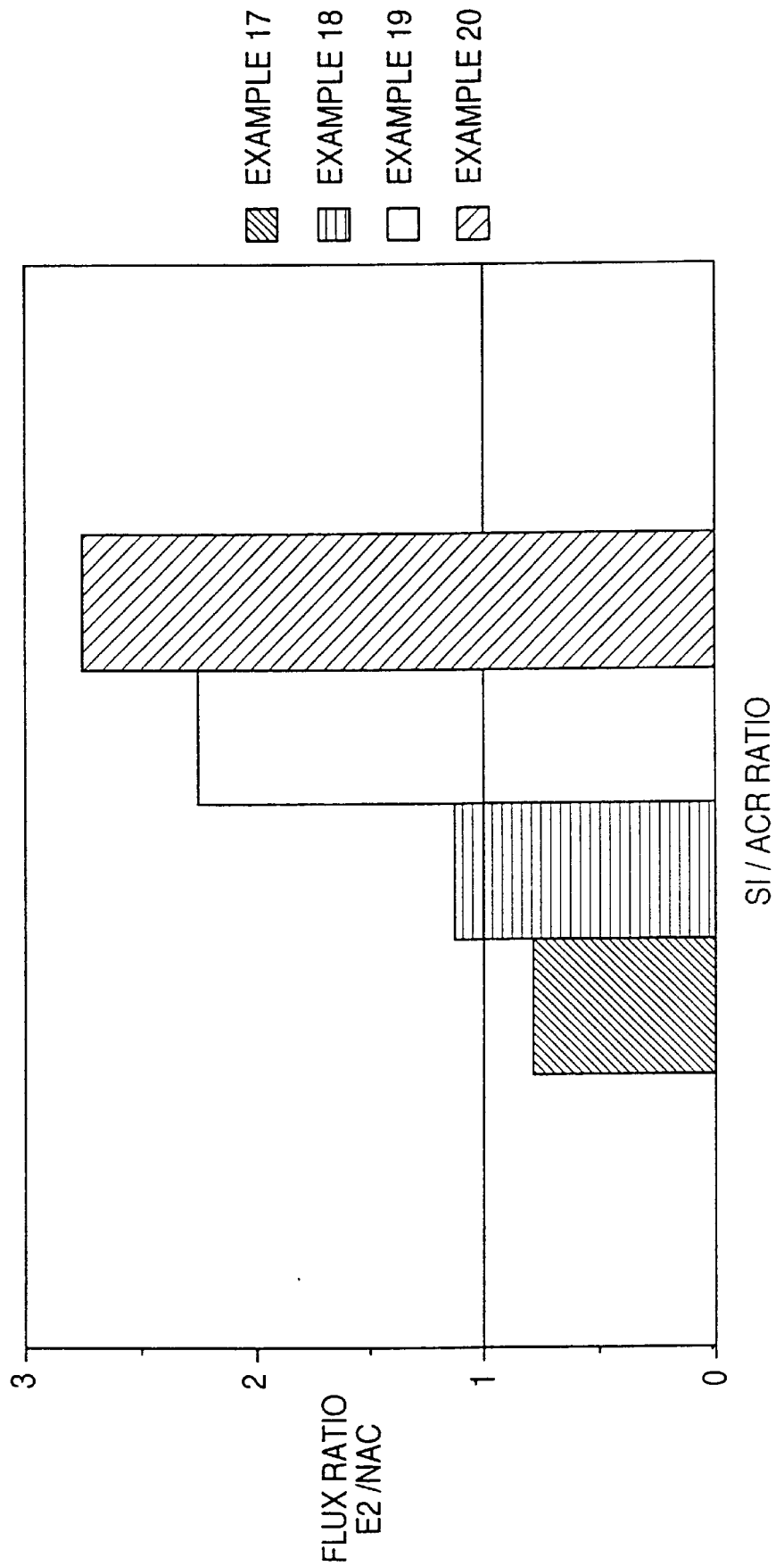
FIG. 9 is a graphical representation showing the ratio of average estradiol to norethindrone acetate flux (estradiol flux divided by norethindrone acetate flux) through cadaver skin in vitro for a multiple polymer transdermal adhesive system comprising various weight ratios of polyacrylate and polysiloxane.

Flux results for the compositions of Examples 17–20 are shown in FIG. 8. As shown in FIG. 8, the flux of both estradiol (E2) and norethindrone acetate (NAc) varied as the polysiloxane to polyacrylate polymer ratio was adjusted; estradiol flux gradually increased and then decreased with a maximum at about 15% acrylate, and the norethindrone acetate flux continuously decreased with increasing acrylate content as would be expected from the data of FIG. 7. A further effect of varying the polysiloxane/polyacrylate polymer ratio is exhibited by a plot of estradiol flux relative to norethindrone acetate flux (estradiol flux divided by norethindrone acetate flux) as shown in FIG. 9. By adjusting the silicone to acrylate polymer ratio, it was possible to modulate the relative delivery of two drugs (estradiol and norethindrone acetate) from the systems of this invention.

Examples 21–23

A pilocarpine-polymer mixture was prepared by combining 5.0 parts of pilocarpine base, 1.2 parts of lecithin, 0.8 parts of propylene glycol, 2.0 parts of oleic acid, 2.5 parts of silicone fluid (polydimethylsiloxane, Dow Corning 360 Medical Fluid, 100 cs), and 77.0 parts of polysiloxane (BIO-PSA X7-3027), and mixing well in an appropriate container. Example 22 incorporated pilocarpine into a polyacrylate comprising National Starch Acrylic Adhesive, Duro-Tak 80-1196. Example 23 employed a blend of polysiloxane and polyacrylate in accordance with the principles of the invention. The resulting compositions had the ingredient concentrations on a "dry" basis, that is, after removal of volatile process solvents, given below in TABLE X.

TABLE X

| Ingredient | 21 | 22 | 23 |
|---|---|---|---|
| Polyacrylate | — | 82.0 | 41.0 |
| Polysiloxane | 77.0 | — | 41.0 |
| Silicone fluid | 5.0 | — | — |
| Pilocarpine | 10.0 | 10.0 | 10.0 |
| Oleic acid | 4.0 | 4.0 | 4.0 |
| Propylene glycol | 1.6 | 1.6 | 1.6 |
| Lecithin fluid | 2.4 | 2.4 | 2.4 |

Figure 10:
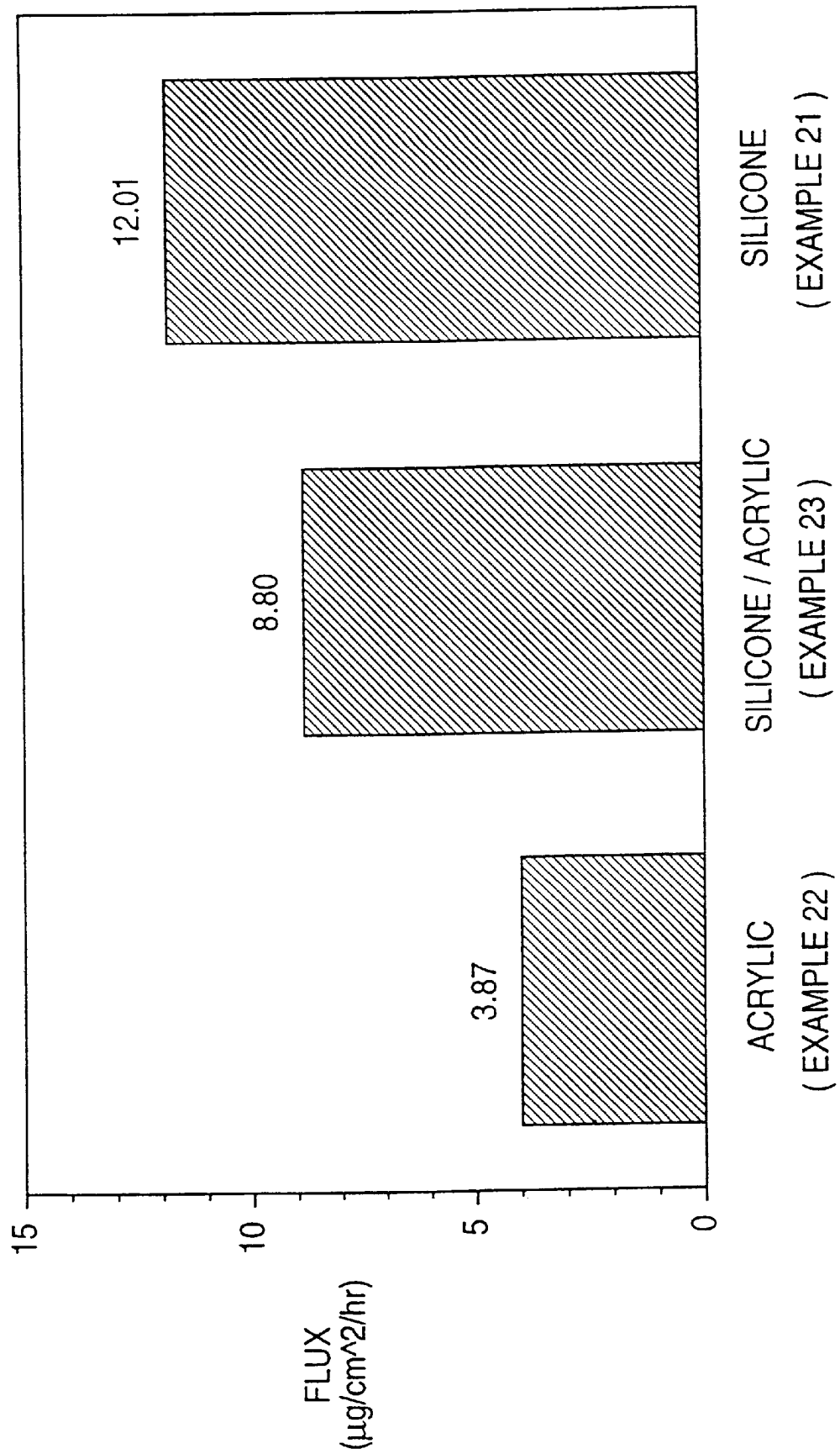
FIG. 10 is a graphical representation of steady-state flux of pilocarpine through cadaver skin in vitro from the drug delivery systems of the prior art, specifically single polymeric adhesives of silicone and acrylic, as compared to a multiple polymer transdermal adhesive system (polyacrylate/polysiloxane) of the present invention.

Pilocarpine flux in vitro from the systems of Examples 21, 22, and 23 is shown in FIG. 10. As seen in FIG. 10, the delivery rate from the system of this invention utilizing the multiple polymer adhesive (polyacrylate/polysiloxane) of Example 23, was intermediate of the delivery rates from single polymer compositions (Examples 21 and 22) which are not of this invention. In this embodiment of the invention, the combination of polyacrylate and polysiloxane polymers adjusted the delivery of rate of pilocarpine within the ranges established by single polymer compositions.

Examples 24–27

An albuterol-polymer mixture was prepared by combining 10.2 parts of albuterol base, 1.5 parts of lecithin, 1.0 part of propylene glycol, 4.1 parts of oleic acid, 2.6 parts of dipropylene glycol, 1.5 parts of butylene glycol, 1.5 parts of vitamin E acetate (tocoperyl acetate), 25.5 parts of polyacrylate (Duro-Tak 80-1196), 11.9 parts of polysiloxane A (BIO-PSA X7-3122), 20.1 parts of polysiloxane B (BIO-PSA X7-3027), and 20.1 parts of isopropyl alcohol, and mixing well in an appropriate container. The resulting composition had the ingredient concentrations on a "dry" basis, that is, after removal of volatile process solvents, given below in Table XI.

The method of Example 24 was used with the appropriate amounts of starting materials to yield the compositions of Examples 25, 26, and 27.

TABLE XI

| Ingredient | 24 | 25 | 26 | 27 |
|---|---|---|---|---|
| Polysiloxane A | 14.0 | 13.8 | 14.0 | 14.0 |
| Polysiloxane B | 19.6 | 19.2 | 28.0 | 19.6 |
| Polyacrylate | 22.4 | 22.0 | 20.0 | 22.4 |
| Albuterol | 20.0 | 20.0 | 20.0 | 20.0 |
| Oleic acid | 8.0 | 8.0 | 8.0 | 8.0 |
| Propylene glycol | 2.0 | 2.0 | 2.0 | 2.0 |
| Dipropylene glycol | 5.0 | 5.0 | 5.0 | 5.0 |
| Butylene glycol | 3.0 | 3.0 | — | 3.0 |
| Vitamin E acetate | 3.0 | 3.0 | — | — |
| Vitamin E | — | 1.0 | — | — |
| Vitamin E linoleate | — | — | — | 3.0 |
| Lecithin | 3.0 | 3.0 | 3.0 | 3.0 |

Figure 11:
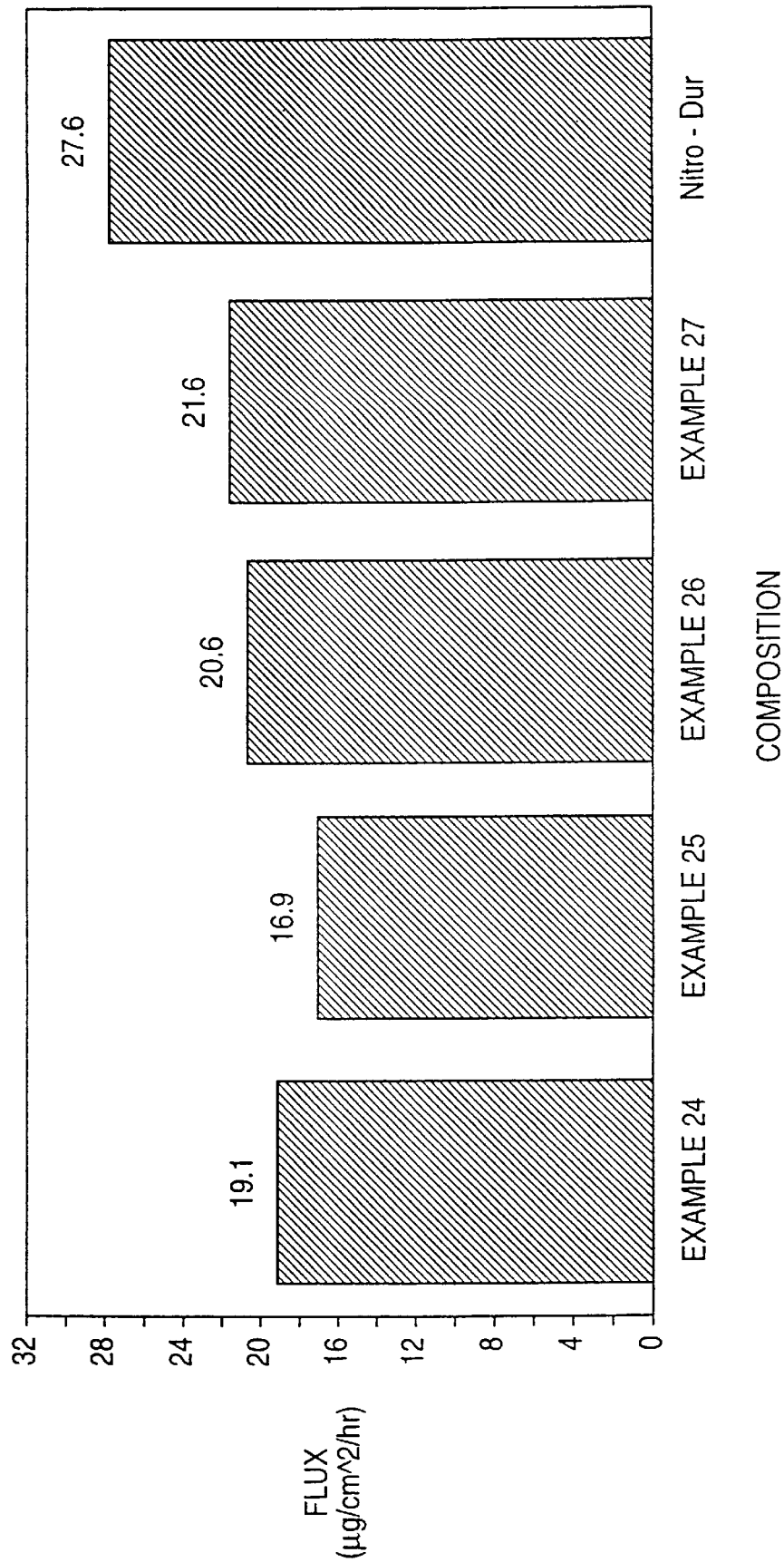
FIG. 11 is a graphical representation of steady-state albuterol and nitroglycerin flux through cadaver skin in vitro from multiple polymer transdermal adhesive systems (polyacrylate/polysiloxane) of the present invention (Examples 24–27), and Nitro-Dur®, respectively.

Albuterol flux results through human cadaver skin in vitro from the formulations of Examples 24, 25, 26, and 27, are summarized in FIG. 11; nitroglycerin flux from Nitro-Dur® through the same skin specimen is shown as a control. Flux values for the albuterol compositions of Example 24 to 27 ranged from about 17 $\mu g/cm^2/hr$ to about 22 $\mu g/cm^2/hr$. The nitroglycerin flux value of about 28 $\mu g/cm^2/hr$ was slightly higher than the literature delivery rate for this product (20 $\mu g/cm^2/hr$, based on Nitro-Dur® product label of 0.1 mg/hr from a 5 $cm^2$ system). In order to adjust for the apparent higher permeability of the skin specimen, albuterol flux results can be multiplied by an adjustment factor of 0.714 (20/28); this would result in flux values of about 12 $\mu g/cm^2/hr$ to about 16 $\mu g/cm^2/hr$.

Therapeutic albuterol plasma concentrations are in the range of about 4 to 8 ng/mL, and are produced by delivery rates of about 115 to 230 $\mu g/hr$. The flux rates (12 to 16 $\mu g/cm^2/hr$) obtained from the compositions of this invention therefore would produce the necessary albuterol plasma levels (4 to 8 ng/mL) for the treatment of asthma from system sizes of about 10 to 20 $cm^2$.

Examples 28–29

Estradiol-polymer mixtures were prepared in accordance with the method of Example 7. Example 28 is illustrative of a multiple polymer adhesive system where polyacrylate is blended with polyisobutylene (Vistanex LM-LS-LC). The resulting compositions had the ingredient concentrations on a "dry" basis, that is, after removal of volatile process solvents, given below in TABLE XII.

TABLE XII

| Ingredient | 28 | 29 |
|---|---|---|
| Polyacrylate | 45.0 | 45.0 |
| Polyisobutylene | 45.0 | — |
| Polysiloxane | — | 45.0 |
| Estradiol | 2.0 | 2.0 |
| Oleic acid | 5.0 | 5.0 |
| Lecithin | 3.0 | 3.0 |

Figure 12:
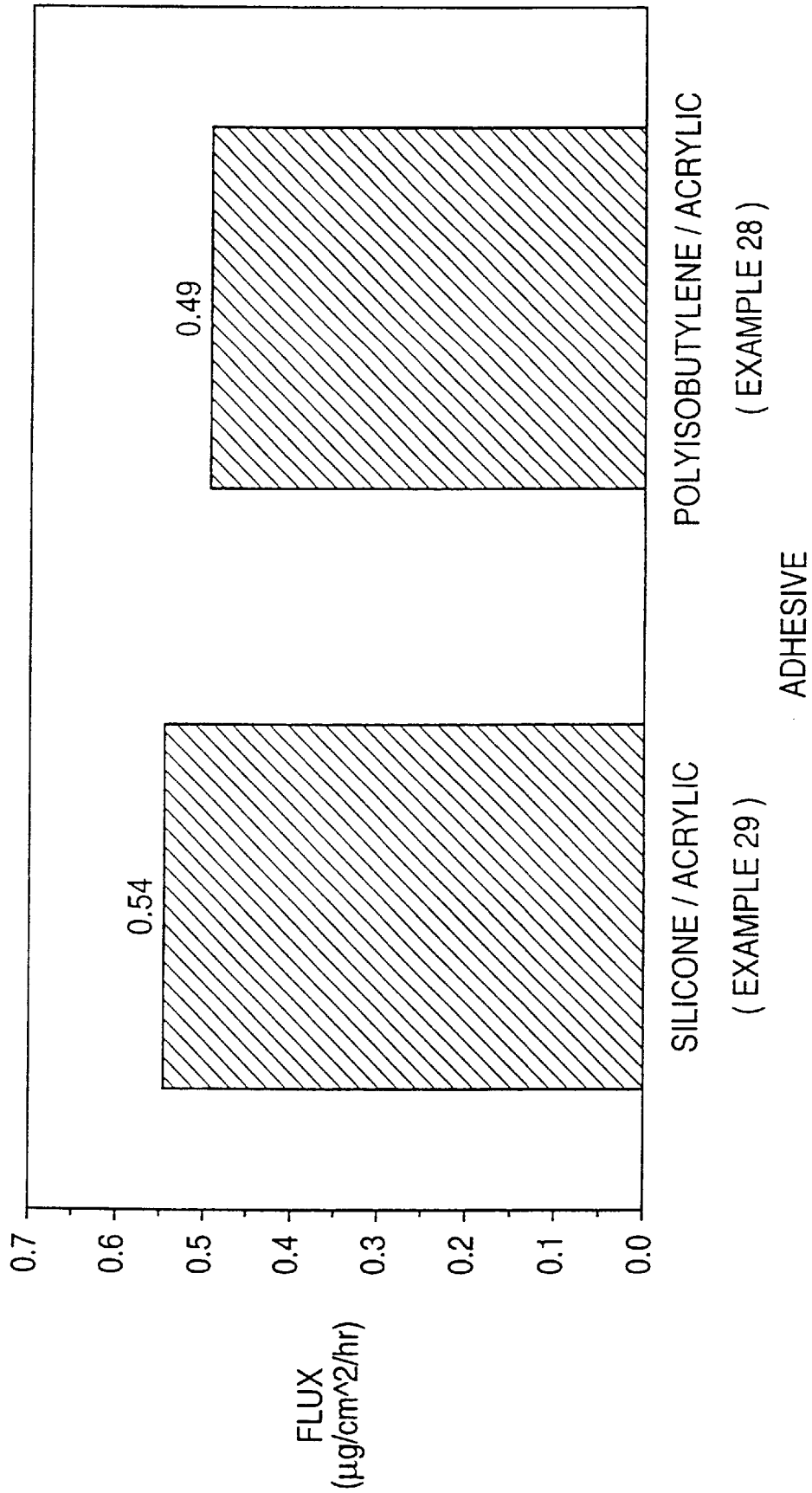
FIG. 12 is a graphical representation of steady-state estradiol flux through cadaver skin in vitro from two different multiple polymer transdermal adhesive systems polyacrylate/polysiloxane and polyacrylate/polybutylene.

Estradiol flux in vitro from the systems of Examples 28 and 29 are shown in FIG. 12. As seen in FIG. 12, delivery from the multiple polymer adhesive system of Example 28 is comparable to delivery from Example 29.

Example 30

In addition to flux measurements, the apparent diffusion coefficient, D, was calculated from release data for nitroglycerin from matrices of Compositions I to VI (Example 6) into an infinite sink. The method of D. R. Paul, *Controlled Release Polymeric Formulations. ACS Symposium Series No. 33*, Chapter 1 (1976) was used wherein the initial concentration of nitroglycerin in the matrix, $C_0$, was determined (assuming a density of 1.0) and the relationship of the amount released, $M_t$, by a matrix of area, A, and the diffusion coefficient is defined by:

$$M_t/A = 2C_0(Dt/\pi)^{1/2}$$

Plotting, $M_t/A$ against $t^{1/2}$, results in a graph having a slope, m, defined by:

$$m = 2C_0(D/\pi)^{1/2}$$

The value of m can be ascertained by linear regression to get the slope of the best fit line. The diffusion coefficient is calculated as:

$$D = \pi(m/2C_0)^2$$

The results of these calculations for Compositions I to VI are shown below in Table XII.

TABLE XIII

| Composition | $C_0(mg/cm^3)$ | $m(mg/cm^2h^{1/2})$ | D $(cm^2/sec)$ | D($\times 10^9$) |
|---|---|---|---|---|
| I | 241.0 | 0.8728 | $2.861 \times 10^9$ | 2.86 |
| II | 233.3 | 0.9483 | $3.605 \times 10^8$ | 36.05 |
| III | 231.3 | 1.0834 | $4.786 \times 10^8$ | 47.86 |
| IV | 219.7 | 1.2502 | $7.065 \times 10^8$ | 70.65 |
| V | 217.0 | 1.5920 | $1.174 \times 10^7$ | 117.4 |
| VI | 215.0 | 2.4551 | $2.845 \times 10^7$ | 284.5 |
| Nitro-Dur | 380.0 | 1.4680 | $3.256 \times 10^8$ | 32.56 |

Figure 13:
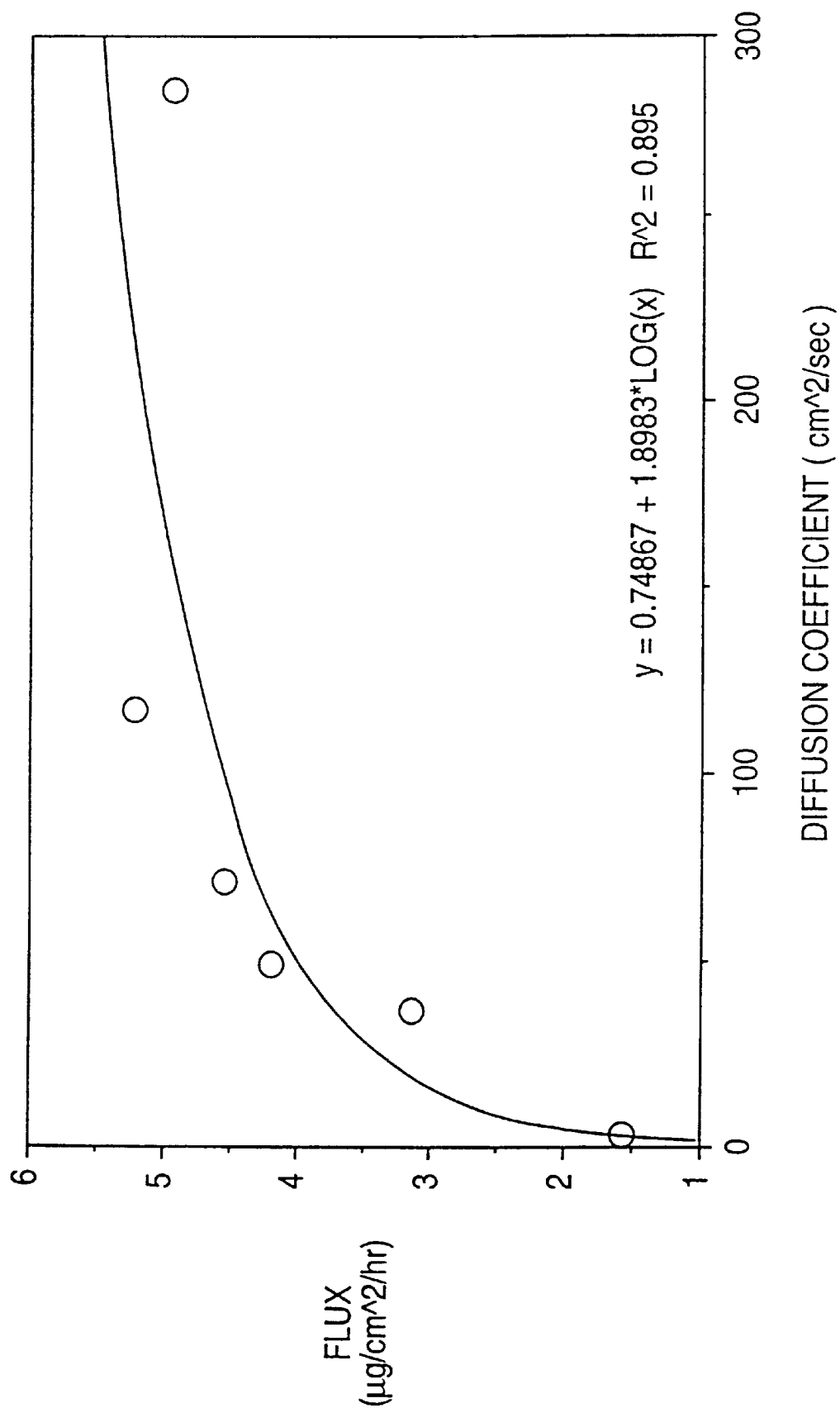
FIGS. 13 and 14 show the relationship of flux rate (J) plotted against apparent diffusion coefficient (D) and net solubility parameter (SP), respectively, for Compositions I–VI of Example 6. The net solubility parameter, $SP_{net}$, was calculated using a weighted average of the solubility parameters of the individual polymers comprising the matrix.
Figure 14:
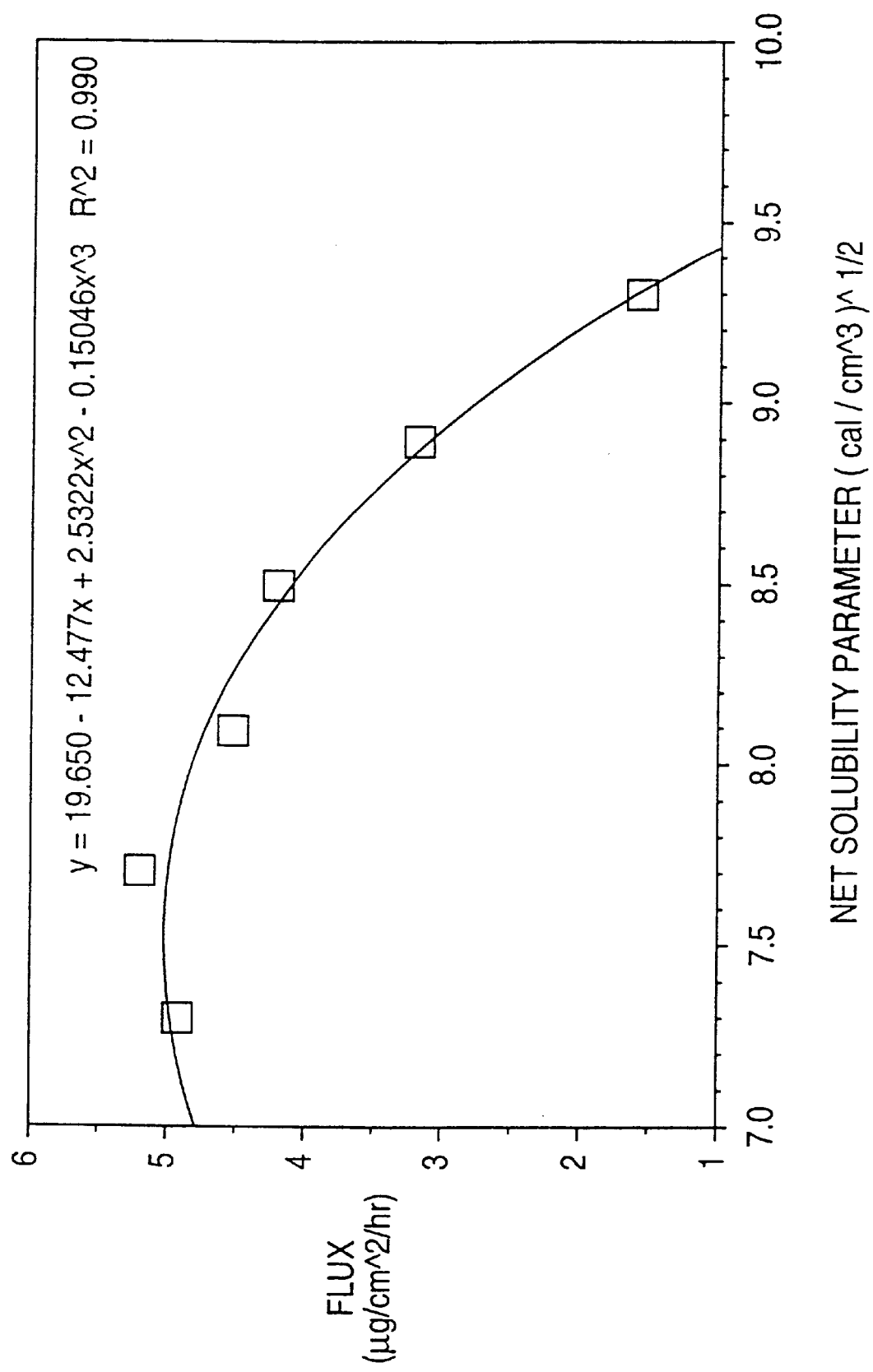

FIGS. 13 and 14 show the relationship of flux rate (J) plotted against apparent diffusion coefficient (D) and net solubility parameter (SP), respectively, for Compositions I–VI. The net solubility parameter, $SP_{net}$, was calculated using a weighted average of the solubility parameters of the individual polymers comprising the matrix:

$$SP_{net} = \phi_{ps}SP_{ps} + \phi_{pa}SP_{pa},$$

where $\phi_{ps}$ the weight percentage of polysiloxane and $SP_{ps}$ is the solubility parameter of polysiloxane. The subscript "pa" refers to the polyacrylate. FIG. 15 is a plot of diffusion coefficient versus net solubility parameter.

Tables XIV-A and XIV-B list additional preferred embodiments, which are prepared according to the procedure of Example 7 in the same manner as the preceding preferred embodiments. Table XIV-A lists the polymers and drugs utilized in each embodiment, while Table XIV-B lists additives so utilized.

| COMPONENT | PERCENT BY WEIGHT |
|---|---|
| Polysiloxane Adhesive (BIO-PSA X7-4503) | 40.0 |
| Polyacrylate Adhesive (Monsanto GMS 737) | 40.0 |
| Oleic Acid | 8.0 |

TABLE XIV-A

| Ingredient (SP, [J/cm³]^(1/2)) | Ex. 31 | Ex. 32 | Ex. 33 | Ex. 34 | Ex. 35 | Ex. 36 | Ex. 37 | Ex. 38 | Ex. 39 | Ex. 40 | Ex. 41 | Ex. 42 |
|---|---|---|---|---|---|---|---|---|---|---|---|---|
| Polyacrylate (21) | 33.1 | 33.1 | 42.0 | 42.0 | 15.0 | 15.0 | | | | | | |
| Polyethylene (16.6) | 40.1 | | | | | | | | | | | |
| Polyisoprene (16.6) | | 40.1 | | | | | | | | | | |
| Polybutadiene (15) | | | 41.0 | | | | | | | | | |
| Polyethylene/butylene (15) | | | | 41.0 | | | | | | | | |
| Polytetrafluoroethylene (12.7) | | | | | 60.0 | | | | | | | |
| Polybutadiene/styrene (17.4) | | | | | | 60.0 | | | | | | |
| Polysiloxane (15) | | | | | | | 46.0 | 46.0 | 41.0 | 41.0 | 42.0 | 42.0 |
| Polystyrene (18.6) | | | | | | | 46.0 | | | | | |
| Polyvinyl chloride (19.4) | | | | | | | | 46.0 | | | | |
| Polyvinylidene chloride (24.9) | | | | | | | | | 41.0 | | | |
| Polychloroprene (19.2) | | | | | | | | | | 41.0 | | |
| Polyacrylonitrile (26.0) | | | | | | | | | | | 20.0 | |
| Butadiene/acrylonitrile (18.9) | | | | | | | | | | | | 20.0 |
| Nitroglycerine (27) | 20.8 | 20.8 | | | | | | | | | | |
| 17β-estradiol (24.5) | | | 2.0 | 2.0 | 2.0 | 2.0 | | | | | | |
| Norethindrone acetate (21.3) | | | | | 2.0 | 2.0 | 3.0 | 3.0 | | | | |
| Pilocaprine (22.9) | | | | | | | | | 10.0 | 10.0 | | |
| Albuterol (26.7) | | | | | | | | | | | 20.0 | 20.0 |

TABLE XIV-B

| | Ex. 31 | Ex. 32 | Ex. 33 | Ex. 34 | Ex. 35 | Ex. 36 | Ex. 37 | Ex. 38 | Ex. 39 | Ex. 40 | Ex. 41 | Ex. 42 |
|---|---|---|---|---|---|---|---|---|---|---|---|---|
| Oleic acid | 2.0 | 2.0 | 5.0 | 5.0 | 2.0 | 2.0 | | | 4.0 | 4.0 | 8.0 | 8.0 |
| Propylene glycol | 0.8 | 0.8 | 2.0 | 2.0 | | | | | 1.6 | 1.6 | 2.0 | 2.0 |
| Dipropylene glycol | 1.0 | 1.0 | 5.0 | 5.0 | | | | | | | 5.0 | 5.0 |
| Butylene glycol | | | | | 2.0 | 2.0 | 5.0 | 5.0 | | | | |
| Bentonite | 1.0 | 1.0 | | | | | | | | | | |
| Lecithin | 1.2 | 1.2 | 3.0 | 3.0 | 5.0 | 5.0 | | | 2.4 | 2.4 | 3.0 | 3.0 |
| Silicone fluid | | | | | 12.0 | 12.0 | | | | | | |

Example 43

An estradiol-polymer mixture was prepared by combining 1.0 part of estradiol, 6.0 parts of dipropylene glycol, 8.0 parts of oleic acid, 35.0 parts of toluene, 5.0 parts of polyvinylpyrrolidone (Kollidon 30), and 129.03 parts of polyacrylate adhesive (GMS737) in an appropriate container, and mixing well until the mixture was completely homogeneous. Then 66.67 parts of silicone adhesive (X7-4503) were added, and the blend was thoroughly mixed. The resulting composition has the ingredient concentrations on a "dry" basis, that is, after removal of volatile process solvents, given below.

-continued

| COMPONENT | PERCENT BY WEIGHT |
|---|---|
| Dipropylene Glycol | 6.0 |
| Polyvinylpyrrolidone (Kollidon 30) | 5.0 |
| Estradiol | 1.0 |
| | 100.0 |

In the following examples the method of Example 43 was used with the appropriate amounts of starting materials to yield compositions having the following ingredient concentrations.

Example 44

| COMPONENT | PERCENT BY WEIGHT |
| --- | --- |
| Polysiloxane Adhesive (BIO-PSA X7-4503) | 39.0 |
| Polyacrylate Adhesive (Monsanto GMS 737) | 40.0 |
| Oleic Acid | 8.0 |
| Dipropylene Glycol | 6.0 |
| Polyvinylpyrrolidone (Kollidon 30) | 5.0 |
| Estradiol | 2.0 |
| | 100.0 |

Example 45

| COMPONENT | PERCENT BY WEIGHT |
| --- | --- |
| Polysiloxane Adhesive (BIO-PSA X7-4503) | 48.0 |
| Polyacrylate Adhesive (Monsanto GMS 737) | 30.0 |
| Oleic Acid | 6.0 |
| Dipropylene Glycol | 4.0 |
| Polyvinylpyrrolidone (Kollidon 30) | 10.0 |
| Estradiol | 2.0 |
| | 100.0 |

Estradiol permeation through human epidermis in vitro from systems of Examples 44 and 45 are shown in FIG. 16. This graph illustrates how the formulas of this invention delivered significantly greater estradiol than Estraderm™, the commercially available estradiol product.

Example 46

An estradiol/norethindrone acetate-polymer mixture was prepared by combining 0.04 parts of estradiol, 2.48 parts of norethindrone acetate, 3.31 parts of dipropylene glycol, 4.96 parts of oleic acid, 49.62 parts of toluene, 8.27 parts of polyvinylpyrrolidone (Kollidon 30), 0.83 parts of butylated hydroxyanlsole, and 53.36 parts of polyacrylate adhesive (GMS 737) in an appropriate container, and mixing well until the mixture was completely homogeneous. Then 77.12 parts of polysiloxane adhesive (X74503) were added, and the blend was thoroughly mixed. The resulting composition has the ingredient concentrations on a "dry" basis, that is, after removal of volatile process solvents, given below.

| COMPONENT | PERCENT BY WEIGHT |
| --- | --- |
| Polysiloxane Adhesive (BIO-PSA X7-4503) | 55.95 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 10.00 |
| Butylated Hydroxyanisole | 1.00 |
| Norethindrone Acetate | 3.00 |
| Estradiol | 0.05 |
| | 100.0 |

In the following examples the method of Example 46 was used with the appropriate amounts of starting materials to yield compositions having the following ingredient concentrations.

Example 47

| COMPONENT | PERCENT BY WEIGHT |
| --- | --- |
| Polysiloxane Adhesive (BIO-PSA X7-4503) | 55.90 |
| Polyacrylate Adhesive (Monsanto GMS 737) | 20.0 |
| Oleic Acid | 6.00 |
| Dipropylene Glycol | 4.00 |
| Polyvinylpyrrolidone (Kollidon 30) | 10.00 |
| Butylated Hydroxyanisole | 1.00 |
| Norethindrone Acetate | 3.00 |
| Estradiol | 0.10 |
| | 100.0 |

Example 48

| COMPONENT | PERCENT BY WEIGHT |
| --- | --- |
| Polysiloxane Adhesive (BIO-PSA X7-4503) | 55.80 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 10.00 |
| Butylated Hydroxyanisole | 1.00 |
| Norethindrone Acetate | 3.00 |
| Estradiol | 0.20 |
| | 100.0 |

Example 49

| COMPONENT | PERCENT BY WEIGHT |
| --- | --- |
| Polysiloxane Adhesive (BIO-PSA X7-4503) | 55.60 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 10.00 |

-continued

| COMPONENT | PERCENT BY WEIGHT |
|---|---|
| Butylated Hydroxyanisole | 1.00 |
| Norethindrone Acetate | 3.00 |
| Estradiol | 0.40 |
| | 100.0 |

Example 50

| COMPONENT | PERCENT BY WEIGHT |
|---|---|
| Polysiloxane Adhesive (BIO-PSA X7-4503) | 55.60 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 10.00 |
| Butylated Hydroxyanisole | 1.00 |
| Norethindrone Acetate | 3.00 |
| Estradiol | 0.50 |
| | 100.0 |

Example 51

| COMPONENT | PERCENT BY WEIGHT |
|---|---|
| Polysiloxane Adhesive (BIO-PSA X7-4503) | 55.40 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 10.00 |
| Butylated Hydroxyanisole | 1.00 |
| Norethindrone Acetate | 3.00 |
| Estradiol | 0.60 |
| | 100.0 |

Example 52

| COMPONENT | PERCENT BY WEIGHT |
|---|---|
| Polysiloxane Adhesive (BIO-PSA X7-4503) | 55.20 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 10.00 |
| Butylated Hydroxyanisole | 1.00 |
| Norethindrone Acetate | 3.00 |
| Estradiol | 0.80 |
| | 100.0 |

Example 53

| COMPONENT | PERCENT BY WEIGHT |
|---|---|
| Polysiloxane Adhesive (BIO-PSA X7-4503) | 55.00 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 10.00 |
| Butylated Hydroxyanisole | 1.00 |
| Norethindrone Acetate | 3.00 |
| Estradiol | 1.00 |
| | 100.0 |

Estradiol flux through human epidermis in vitro from systems of Examples 46 through 53 (with 0.05% to 1.0% estradiol) are presented in FIG. 17. This graph shows how a wide range in estradiol flux was achieved by the formulas of this invention by varying the estradiol concentration. Norethindrone acetate flux was not affected by estradiol concentration, and remained constant at about 0.8 $\mu g/$/hr; see FIG. 18.

Example 54

An estradiol/norethindrone acetate-polymer mixture was prepared by combining 0.20 parts of estradiol, 3.00 parts of norethindrone acetate, 4.00 parts of dipropylene glycol, 6.00 parts of oleic acid, 60.00 parts of toluene, 0.00 parts of polyvinylpyrrolidone (Kollidon 30), 1.00 parts of butylated hydroxyanisole, and 64.52 parts of polyacrylate adhesive (GMS 737) in an appropriate container, and mixing well until the mixture was completely homogeneous. Then 93.00 parts of polysiloxane adhesive (X7-4503) were added, and the blend was thoroughly mixed. The resulting composition has the ingredient concentrations on a "dry" basis, that is, after removal of volatile process solvents in ovens, given below.

| COMPONENT | PERCENT BY WEIGHT |
|---|---|
| Polysiloxane Adhesive (BIO-PSA X7-4503) | 65.80 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 0.00 |
| Butylated Hydroxyanisole | 1.00 |
| Norethindrone Acetate | 3.00 |
| Estradiol | 0.20 |
| | 100.0 |

In the following examples the method of Example 54 was used with the appropriate amounts of starting materials to yield compositions having the following ingredient concentrations.

Example 55

| COMPONENT | PERCENT BY WEIGHT |
| --- | --- |
| Polysiloxane Adhesive (BIO-PSA X7-4503) | 63.30 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 2.50 |
| Butylated Hydroxyanisole | 1.00 |
| Norethindrone Acetate | 3.00 |
| Estradiol | 0.20 |
| | 100.0 |

Example 56

| COMPONENT | PERCENT BY WEIGHT |
| --- | --- |
| Polysiloxane Adhesive (BIO-PSA X7-4503) | 60.80 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 5.00 |
| Butylated Hydroxyanisole | 1.00 |
| Norethindrone Acetate | 3.00 |
| Estradiol | 0.20 |
| | 100.0 |

Example 57

| COMPONENT | PERCENT BY WEIGHT |
| --- | --- |
| Polysiloxane Adhesive (BIO-PSA X7-4503) | 55.80 |
| Polyacrylate Adhesive (Monsanto GMS 737) | 20.00 |
| Oleic Acid | 6.00 |
| Dipropylene Glycol | 4.00 |
| Polyvinylpyrrolidone (Kollidon 30) | 10.00 |
| Butylated Hydroxyanisole | 1.00 |
| Norethindrone Acetate | 3.00 |
| Estradiol | 0.20 |
| | 100.0 |

FIG. 19 shows how systems with varying levels of polyvinylpyrrolidone (0 to 10%) had essentially the same drug (estradiol and norethindrone acetate) flux; Examples 54–57. However, polyvinylpyrrolidone was found to have an effect on drug recrystallization for these systems. That is, the incidence of crystal formation was reduced as the polyvinylpyrrolidone concentration was increased; see Table XV.

TABLE XV

Effects of polyvinylpyrrolidone on crystal formation.

| Formula | % polyvinyl-pyrrolidone | # of crystals in patch* |
| --- | --- | --- |
| Example 54 | 0.0 | 60 ± 4 |
| Example 55 | 2.5 | 56 ± 8 |
| Example 56 | 5.0 | 20 ± 4 |
| Example 57 | 10.0 | 0 |

*number of visible crystals in a 14.4 cm$^2$ patch; average and sd of five patches each.

Example 58

A nitroglycerin-polymer mixture is prepared by combining 20.0 parts of nitroglycerin, 2.00 parts of dipropylene glycol, 2.00 parts of lecithin, and 83.33 parts of ethylene/vinyl acetate polymer (Elvax 40W) in an appropriate container, and mixing well until the mixture is completely homogeneous. Nitroglycerin is available as a solution in solvents such as ethanol, toluene, and propylene glycol from ICI Americas Inc., Wilmington, Del. In this instance, the nitroglycerin is added as a solution in toluene mixed together with the ethylene/vinyl acetate polymer. Then 85.00 parts of polysiloxane adhesive (X7-4503) are added, and the blend is thoroughly mixed. The resulting composition has the ingredient concentrations on a "dry" basis, that is, after removal of volatile process solvents, given below.

| COMPONENT | PERCENT BY WEIGHT |
| --- | --- |
| Polysiloxane Adhesive (BIO-PSA X7-4503) | 51.00 |
| Ethylene/Vinyl Acetate Polymer (Elvax 40W) | 25.00 |
| Dipropylene Glycol | 2.00 |
| Lecithin | 2.00 |
| Nitroglycerin | 20.00 |
| | 100.00 |

In the following examples the method of Example 58 is used with the appropriate amounts of starting materials to yield compositions having the following ingredient concentrations. In this instance, the nitroglycerin is added as a solution in toluene mixed together with polyisobutylene (Vistanex LM-LS-LC).

Example 59

| COMPONENT | PERCENT BY WEIGHT |
| --- | --- |
| Polysiloxane Adhesive (BIO-PSA X7-4503) | 56.00 |
| Polyisobutylene (Vistanex LM-LS-LC) | 20.00 |
| Dipropylene Glycol | 2.00 |
| Lecithin | 2.00 |
| Nitroglycerin | 20.00 |
| | 100.00 |

In the following example, the nitroglycerin is added as a solution in toluene mixed together with styrene-isoprene-styrene (Kraton D 1107) polymer.

Example 60

| COMPONENT | PERCENT BY WEIGHT |
|---|---|
| Polysiloxane Adhesive (BIO-PSA X7-4503) | 46.00 |
| Styrene-isoprene-styrene polymer (Kraton D1107) | 30.00 |
| Dipropylene Glycol | 2.00 |
| Lecithin | 2.00 |
| Nitroglycerin | 20.00 |
| | 100.00 |

Example 61

An isosorbide dinitrate-polymer mixture is prepared by combining 20.0 parts of isosorbide dinitrate, 4.00 parts of dipropylene glycol, 4.00 parts of oleic acid, and 66.67 parts of ethylene/vinyl acetate polymer (Elvax 40W) in an appropriate container, and mixing well until the mixture is completely homogeneous. In this example, the isosorbide dinitrate is added as a solution in toluene mixed together with the ethylene/vinyl acetate polymer. Then 86.67 parts of polysiloxane adhesive (BIO-PSA X7-4503) are added, and the blend is thoroughly mixed. The resulting composition has the ingredient concentrations on a "dry" basis, that is, after removal of volatile process solvents in ovens, given below.

| COMPONENT | PERCENT BY WEIGHT |
|---|---|
| Polysiloxane Adhesive (BIO-PSA X7-4503) | 52.00 |
| Ethylene/Vinyl Acetate Polymer (Elvax 40W) | 20.00 |
| Dipropylene Glycol | 4.00 |
| Oleic Acid | 4.00 |
| Isosorbide Dinitrate | 20.00 |
| | 100.00 |

In the following examples the method of Example 61 is used with the appropriate amounts of starting materials to yield compositions having the following ingredient concentrations. In this instance, the isosorbide dinitrate is added as a solution in toluene mixed together with styrene-butadiene-styrene polymer (Kraton D1101).

Example 62

| COMPONENT | PERCENT BY WEIGHT |
|---|---|
| Polysiloxane Adhesive (BIO-PSA X7-4503) | 47.00 |
| Styrene-butadiene-styrene (Kraton D1101) | 25.00 |
| Dipropylene Glycol | 4.00 |
| Oleic Acid | 4.00 |
| Isosorbide Dinitrate | 20.00 |
| | 100.00 |

In the following example, the isosorbide dinitrate is added as a solution in toluene mixed together with polyacrylate adhesive (Duro-Tak 80-1196).

Example 63

| COMPONENT | PERCENT BY WEIGHT |
|---|---|
| Polysiloxane Adhesive (BIO-PSA X7-4503) | 32.00 |
| Polyacrylate Adhesive (Duro-Tak 80-1196) | 30.00 |
| Polyvinylpyrrolidone (Kollidon 30) | 10.00 |
| Dipropylene Gylcol | 4.00 |
| Oleic Acid | 4.00 |
| Isosorbide Dinitrate | 20.00 |
| | 100.00 |

Example 64

A norethindrone acetate-polymer mixture is prepared by combining 3.00 parts of norethindrone acetate, 4.00 parts of dipropylene glycol, 6.00 parts of oleic acid, 60.00 parts of toluene, 10.00 parts of polyvinylpyrrolidone (Kollidon 30), 1.00 parts of butylated hydroxyanisole, and 64.52 parts of polyacrylate adhesive (GMS 737) in an appropriate container, and mixing well until the mixture is completely homogeneous. Then 95.00 parts of polysiloxane adhesive (BIO-PSA X7-4603) are added, and the blend is thoroughly mixed. The resulting composition has the ingredient concentrations on a "dry" basis, that is, after removal of volatile process solvents, given below.

| COMPONENT | PERCENT BY WEIGHT |
|---|---|
| Polysiloxane Adhesive (BIO-PSA X7-4603) | 57.00 |
| Polyacrylate Adhesive (GMS 737) | 20.00 |
| Dipropylene Glycol | 4.00 |
| Oleic Acid | 6.00 |
| Polyvinylpyrrolidone (Kollidon 30) | 10.00 |
| Norethindrone Acetate | 3.00 |
| | 100.00 |

In the following examples the method of Example 64 is used with the appropriate amounts of starting materials to yield compositions having the following ingredient concentrations.

Example 65

| COMPONENT | PERCENT BY WEIGHT |
|---|---|
| Polysiloxane Adhesive (BIO-PSA X7-4603) | 54.00 |
| Ethylene/Vinyl Acetate Polymer (Elvax 40W) | 25.00 |
| Dipropylene Glycol | 4.00 |
| Oleic Acid | 4.00 |
| Polyvinylpyrrolidone (Kollidon 30) | 10.00 |
| Norethindrone Acetate | 3.00 |
| | 100.00 |

Example 66

An albuterol-polymer mixture is prepared by combining 30.00 parts of albuterol base, 5.00 parts of butylene glycol, 8.00 parts of oleic acid, 3.00 parts of tocopherol acetate (Vitamin E acetate), and 66.67 parts of ethylene/vinyl acetate polymer (Elvax 40W) in an appropriate container, and mixing well until the mixture is thoroughly mixed. Then 56.67 parts of polysiloxane adhesive (BIO-PSA X7-4301) are added, and the blend is thoroughly mixed. The resulting composition has the ingredient concentrations on a "dry" basis, that is, after removal of volatile process solvents, given below.

| COMPONENT | PERCENT BY WEIGHT |
|---|---|
| Polysiloxane Adhesive (BIO-PSA X7-4301) | 34.00 |
| Ethylene/Vinyl Acetate Polymer (Elvax 40W) | 20.00 |
| Butylene Glycol | 5.00 |
| Oleic Acid | 8.00 |
| Tocopherol Acetate (Vitamin E Acetate) | 3.00 |
| Albuterol | 30.00 |
|  | 100.00 |

In the following examples the method of Example 66 is used with the appropriate amounts of starting materials to yield compositions having the following ingredient concentrations.

Example 67

| COMPONENT | PERCENT BY WEIGHT |
|---|---|
| Polysiloxane Adhesive (BIO-PSA X7-4301) | 46.00 |
| Polyisobutylene (Vistanex LM-MS-LC) | 20.00 |
| Dipropylene Glycol | 5.00 |
| Oleic Acid | 6.00 |
| Tocopherol Acetate (Vitamin E Acetate) | 3.00 |
| Albuterol | 20.00 |
|  | 100.00 |

Example 68

| COMPONENT | PERCENT BY WEIGHT |
|---|---|
| Polysiloxane Adhesive (BIO-PSA X7-4301) | 54.00 |
| Styrene-ethylene/butylene-styrene polymer (Kraton G1657) | 20.00 |
| Lecithin | 3.00 |
| Oleic Acid | 5.00 |
| Tocopherol Acetate (Vitamin E Acetate) | 3.00 |
| Pilocarpine | 15.00 |
|  | 100.00 |

Example 69

| COMPONENT | PERCENT BY WEIGHT |
|---|---|
| Polysiloxane Adhesive (BIO-PSA X7-4303) | 39.00 |
| Ethylene/Vinyl Acetate Polymer (Elvax 40W) | 25.00 |
| Butylene Glycol | 5.00 |
| Oleic Acid | 8.00 |
| Tocopherol Acetate (Vitamin E Acetate) | 3.00 |
| Philocarpine | 20.00 |
|  | 100.00 |

Example 70

| COMPONENT | PERCENT BY WEIGHT |
|---|---|
| Polysiloxane Adhesive (BIO-PSA X7-4301) | 53.00 |
| Polyisobutylene (Vistanex LM-MS-LC) | 20.00 |
| Oleic Acid | 5.00 |
| Tocopherol Linoleate (Vitamin E Linoleate) | 2.00 |
| Alprazolam | 20.00 |
|  | 100.00 |

Example 71

| COMPONENT | PERCENT BY WEIGHT |
|---|---|
| Polysiloxane Adhesive (BIO-PSA X7-4303) | 37.00 |
| Styrene Butadiene Rubber (Vistanex LM-MS-LC) | 20.00 |
| Dipropylene Glycol | 2.00 |
| Oleic Acid | 8.00 |
| Tocopherol Acetate (Vitamin E Acetate) | 3.00 |
| Alprazolam | 30.00 |
|  | 100.00 |

Example 72

| COMPONENT | PERCENT BY WEIGHT |
|---|---|
| Polysiloxane Adhesive (BIO-PSA X7-4301) | 56.00 |
| Styrene-isoprene-styrene Polymer (Kraton D1107) | 15.00 |
| Propylene Gylcol | 5.00 |
| Linoleic Acid | 8.00 |
| Lecithin (Vitamin E Acetate) | 6.00 |
| Haloperidol | 10.00 |
|  | 100.00 |

Example 73

| COMPONENT | PERCENT BY WEIGHT |
|---|---|
| Polysiloxane Adhesive (BIO-PSA X7-4301) | 61.00 |
| Ethylene/Vinyl Acetate Polymer (Elvax 40W) | 10.00 |
| Oleic Acid | 6.00 |
| Tocopherol Acetate (Vitamin E Acetate) | 3.00 |
| Haloperidol | 20.00 |
| | 100.00 |

Example 74

| COMPONENT | PERCENT BY WEIGHT |
|---|---|
| Polysiloxane Adhesive (BIO-PSA X7-4301) | 44.00 |
| Butyl Rubber | 25.00 |
| Butylene Glycol | 5.00 |
| Linoleic Acid | 8.00 |
| Tocopherol Acetate (Vitamin E Acetate) | 3.00 |
| Haloperidol | 15.00 |
| | 100.00 |

Example 75

| COMPONENT | PERCENT BY WEIGHT |
|---|---|
| Polysiloxane Adhesive (BIO-PSA X7-4301) | 60.00 |
| Polybutene | 15.00 |
| Oleic Acid | 5.00 |
| Lecithin | 5.00 |
| Alprazolam | 15.00 |
| | 100.00 |

Example 76

| COMPONENT | PERCENT BY WEIGHT |
|---|---|
| Polysiloxane Adhesive (BIO-PSA X7-4301) | 62.00 |
| Polyisobutylene (Vistanex LM-MS-LC) | 20.00 |
| Dipropylene Glycol | 4.00 |
| Oleic Acid | 4.00 |
| Polyviriylpyrrolidone (Kollidon 17PF) | 5.00 |
| Lecithin (Vitamin E Acetate) | 3.00 |
| Estradiol | 2.00 |
| | 100.00 |

Example 77

| COMPONENT | PERCENT BY WEIGHT |
|---|---|
| Polyacrylate Adhesive (GMS 737) | 55.00 |
| Polyisobutylene | 20.00 |
| Dipropylene Glycol | 5.00 |
| Oleic Acid | 8.00 |
| Polyvinylpyrrolidone (Kollidon 30) | 10.00 |
| Haloperidol | 2.00 |
| | 100.00 |

Example 78

| COMPONENT | PERCENT BY WEIGHT |
|---|---|
| Polysiloxane Adhesive (BIO-PSA X7-4301) | 51.00 |
| Polysobutylene (Vistanex LM-MS-LC) | 20.00 |
| Propylene Glycol | 5.00 |
| Oleic Acid | 6.00 |
| Lecithin | 3.00 |
| Lidocaine | 15.00 |
| | 100.00 |

Example 79

| COMPONENT | PERCENT BY WEIGHT |
|---|---|
| Polysiloxane Adhesive (BIO-PSA X7-4301) | 53.00 |
| Ethylene/Vinyl Acetate Polymer (Elvax 40W) | 15.00 |
| Dipropylene Glycol | 5.00 |
| Linoleic Acid | 4.00 |
| Tocopherol Acetate (Vitamin E Acetate) | 3.00 |
| Lidocaine | 20.00 |
| | 100.00 |

Example 80

| COMPONENT | PERCENT BY WEIGHT |
|---|---|
| Polysiloxane Adhesive (BIO-PSA X7-4301) | 72.00 |
| Ethylene/Vinyl Acetate Polymer (Elvax 40W) | 20.00 |
| Tocopherol Acetate (Vitamin E Acetate) | 3.00 |
| Nicotine | 5.00 |
| | 100.00 |

Example 81

| COMPONENT | PERCENT BY WEIGHT |
|---|---|
| Polysiloxane Adhesive (BIO-PSA X7-4303) | 65.00 |
| Polysobutylene (Vistanex LM-MS-LC) | 20.00 |
| Tocopherol Acetate (Vitamin E Acetate) | 5.00 |
| Nicotine | 10.00 |
| | 100.00 |

Example 82

| COMPONENT | PERCENT BY WEIGHT |
|---|---|
| Polysiloxane Adhesive (BIO-PSA X7-4301) | 52.00 |
| Polyacrylate Adhesive (Duro-Tak 80-1196) | 20.00 |
| Polyvinylpyrrolidone (Kollidon 30) | 10.00 |
| Dipropylene Glycol | 5.00 |
| Oleic Acid (Vitamin E Acetate) | 8.00 |
| Fentanyl | 5.00 |
| | 100.00 |

Example 83

| COMPONENT | PERCENT BY WEIGHT |
|---|---|
| Polysiloxane Adhesive (BIO-PSA X7-4303) | 63.00 |
| Ethylene/Vinyl Acetate Polymer (Elvax 40W) | 15.00 |
| Butylene Glycol | 5.00 |
| Oleic Acid | 8.00 |
| Tocopherol Acetate (Vitamin E Acetate) | 3.00 |
| Fentanyl | 6.00 |
| | 100.00 |

Example 84

| COMPONENT | PERCENT BY WEIGHT |
|---|---|
| Polysiloxane Adhesive (BIO-PSA X7-4301) | 65.00 |
| Ethylene/Vinyl Acetate Polymer (Elvax 40W) | 20.00 |

-continued

| COMPONENT | PERCENT BY WEIGHT |
|---|---|
| Polyethylene Glycol 400 | 5.00 |
| Tocopherol Acetate (Vitainin E Acetate) | 5.00 |
| Papaverine | 5.00 |
| | 100.00 |

Example 85

| COMPONENT | PERCENT BY WEIGHT |
|---|---|
| Polysiloxane Adhesive (BIO-PSA X7-4601) | 81.00 |
| Polyvinylpyrrolidone (Kollidon 30) | 10.00 |
| Dipropylene Glycol | 3.00 |
| Oleic Acid | 5.00 |
| Estradiol | 20.00 |
| | 100.00 |

Example 86

| COMPONENT | PERCENT BY WEIGHT |
|---|---|
| Polyisobutylene (Vistanex LM-MS-LC) | 81.00 |
| Polyvinylpyrrolidone (Kollidon 17PF) | 10.00 |
| Dipropylene Glycol | 2.00 |
| Oleic Acid | 6.00 |
| Estradiol | 1.00 |
| | 100.00 |

Example 87

| COMPONENT | PERCENT BY WEIGHT |
|---|---|
| Polysiloxane Adhesive (BIO-PSA X7-4503) | 80.00 |
| Polyvinylpyrrolidone (Kollidon 17PF) | 10.00 |
| Dipropylene Glycol | 3.00 |
| Oleic Acid | 5.00 |
| Norethindrone Acetate | 2.00 |
| | 100.00 |

Example 88

| COMPONENT | PERCENT BY WEIGHT |
|---|---|
| Polyacrylate Adhesive (GMS 737) | 77.00 |
| Polyvinylpyrrolidone (Kollidon 30) | 10.00 |
| Dipropylene Glycol | 4.00 |

-continued

| COMPONENT | PERCENT BY WEIGHT |
|---|---|
| Oleic Acid | 6.00 |
| Norethindrone Acetate | 3.00 |
| | 100.00 |

Example 89

| COMPONENT | PERCENT BY WEIGHT |
|---|---|
| Polyacrylate Adhesive (GMS 737) | 77.00 |
| Polyvinylpyrrolidone (Kollidon 30) | 10.00 |
| Dipropylene Glycol | 4.00 |
| Oleic Acid | 6.00 |
| Norethindrone Acetate | 3.00 |
| Estradiol | 0.20 |
| | 100.00 |

Example 90

| COMPONENT | PERCENT BY WEIGHT |
|---|---|
| Duro-Tak (Monsanto 80-1196) | 69.00 |
| Polyvinylpyrrolidone (Kollidon 30) | 10.00 |
| Butylene Glycol | 5.00 |
| Oleic Acid | 8.00 |
| Tocopherol Acetate (Vitamin E Acetate) | 3.00 |
| Fentanyl | 5.00 |
| | 100.00 |

Example 91

| COMPONENT | PERCENT BY WEIGHT |
|---|---|
| Polysiloxane Adhesive (BIO-PSA X7-4503) | 58.0 |
| Polyacrylate Adhesive (Monsanto GMS 737) | 30.0 |
| Oleic Acid | 6.0 |
| Dipropylene Glycol | 4.0 |
| Polyvinylpyrrolidone (Kollidon 17PF) | 0.0 |
| Estradiol | 2.0 |
| | 100.00 |

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A pressure-sensitive adhesive composition suitable for use in a transdermal drug delivery system, which composition comprises a blend of:
    (a) a rubber adhesive, wherein the rubber adhesive is present in an amount from 5% to 97% by weight of the total composition;
    (b) a polyacrylate in an amount from 1% to 85% by weight of the total composition, wherein the ratio of the polyacrylate to the rubber adhesive is from 2:98 to 96:4;
    (c) a therapeutically effective amount a mixture of two or more drugs for transdermal drug delivery, wherein the drug is present in an amount weight 0.1% to 50% by weight of the total composition, and wherein said two or more drugs include an androgenic steroid and an estrogen; and
    (d) a soluble polyvinylpyrrolidone, wherein the soluble polyvinylpyrrolidone is present in an amount of 1% to 20% by weight of the total composition,
wherein the ratio of the drug to the soluble polyvinylpyrrolidone is from 1:10 to 10:1, and
wherein the amount of soluble polyvinylpyrrolidone is sufficient to solubilize all of the drug which is present in an amount that would exceed its solubility in a composition that contains a rubber adhesive and a polyacrylate, but lacks soluble polyvinylpyrrolidone.

2. A pressure-sensitive adhesive composition suitable for use in a transdermal drug delivery system, which composition comprises a blend of:
    (a) a synthetic elastomeric polymer;
    (b) a soluble polyvinylpyrrolidone;
    (c) a therapeutically effective amount of a drug or a mixture of two or more drugs for transdermal drug delivery, wherein said two or more drugs include an androgenic steroid and an estrogen; and
    (d) optionally one or more additives selected from the group consisting of enhancers, fillers, plasticizers, tackifying agents, and co-solvents.

3. A pressure-sensitive adhesive composition suitable for use in a transdermal drug delivery system, which composition comprises a blend of
    (a) a rubber;
    (b) a soluble polyvinylpyrrolidone;
    (c) a therapeutically effective amount of a drug or a mixture of two or more drugs for transdermal drug delivery, wherein said two or more drugs include an androgenic steroid and an estrogen; and
    (d) optionally one or more additives selected from the group consisting of enhancers, fillers, plasticizers, tackifying agents, and co-solvents.

4. A pressure-sensitive adhesive composition suitable for use in a transdermal drug delivery system, which composition comprises a blend of:
    (a) a rubber adhesive, wherein the rubber adhesive is present in an amount from 5% to 97% by weight of the total composition;
    (b) a polyacrylate in an amount from 1% to 85% by weight of the total composition, wherein the ratio of the polyacrylate to the rubber adhesive is from 2:98 to 96:4;
    (c) a therapeutically effective amount a drug for transdermal drug delivery, wherein the drug is present in an amount of 0.1% to 50% by weight of the total composition, and wherein said drug is selected from the group consisting of terbinafine, sumatriptan, physostigmine, loratadine, simvastatin, pravstatin, methimazole, alendranate, etidronate, ropinirole, pramipexole, fenoldopam, and nimesulide; and (d) a soluble polyvinylpyrrolidone, wherein the soluble polyvinylpyrrolidone is present in an amount of 1% to 20% by weight of the total composition, wherein the ratio of the drug to the soluble polyvinylpyrrolidone is from 1:10 to 10:1, and wherein the amount of soluble polyvinylpyrrolidone is sufficient to solubilize all of the drug which is present in an amount that would exceed its solubility in a composition that contains a rubber adhesive and a polyacrylate, but lacks soluble polyvinylpyrrolidone.

* * * * *